US010639277B1

(12) United States Patent
Geng et al.

(10) Patent No.: US 10,639,277 B1
(45) Date of Patent: May 5, 2020

(54) MULTI-FUNCTIONAL ECHOGENIC IMMUNOLIPOSOMES FOR DIRECTED STEM CELL DELIVERY TO ATHEROMA

(71) Applicant: BOARD OF REGENTS OF THE UNIVERSITY OF TEXAS SYSTEM, Austin, TX (US)

(72) Inventors: Yong-Jian Geng, Pearland, TX (US); David D. McPherson, Houston, TX (US); Melvin E. Klegerman, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 97 days.

(21) Appl. No.: 15/887,316

(22) Filed: Feb. 2, 2018

Related U.S. Application Data

(63) Continuation of application No. 12/749,219, filed on Mar. 29, 2010, now abandoned.

(60) Provisional application No. 61/164,238, filed on Mar. 27, 2009.

(51) Int. Cl.
| | |
|---|---|
| *A01K 67/027* | (2006.01) |
| *A61K 35/407* | (2015.01) |
| *C12N 15/85* | (2006.01) |
| *C12N 15/877* | (2010.01) |
| *C12N 15/90* | (2006.01) |
| *C12N 9/02* | (2006.01) |
| *C12N 9/10* | (2006.01) |
| *C12N 9/22* | (2006.01) |
| *C12N 9/40* | (2006.01) |
| *A61K 9/127* | (2006.01) |
| *G01N 33/50* | (2006.01) |

(52) U.S. Cl.
CPC ....... *A61K 9/1271* (2013.01); *G01N 33/5047* (2013.01)

(58) Field of Classification Search
None
See application file for complete search history.

(56) References Cited

PUBLICATIONS

Bartley, et al., "Stem Cell Therapy for Cerebral Palsy", Expert Opinion in Biological Therapy, 3(4): 541-49 (2003).
Geng, et al., "Transplantation of Bone Marrow Stem Cells Complexed With Immunoliposomes Targeted to CD34 and ICAM-1 Reduces Atherosclerosis in Apolipoprotein-e Null Mice", Circulation, 112: A19643 (2010).
Herbst, et al., "Delivery of Stem Cells to Porcine Arterial Wall with Echogenic Liposomes Conjugated to Antibodies against CD34 and Intercellular Adhesions Molecule-1" Molecular Pharmacology, 7(1): online pp. 1-18, p. 8, 3$^{rd}$ full paragraph) (2010).
Hitchcok, et al., "Ultrasound-Mediated Delivery of Targeted Echogenic Liposomes in an Ex Vivo Mouse Aorta" Journal of Controlled Release, 144: 288-95 (2010).
Kopechek, et al., "Acoustic Characterization of Echogenic Liposomes: Frequency-Dependent Attenuation and Backscatter", Journal of Acoustic Society of America, 130: 3472-3481 (2011).
Madonna, R., et al., "Targeting Atheroma in Apolipoprotein-E-Deficient Mice with Stem Cells Labeled with Anti-CD34/ICAM-1 Immunoliposomes", ATVB Abstracts e309; P672 (2010).
U.S. Appl. No. 12/749,219, "Multi-Functional Echogenic Immunoliposomes for Directed Stem Cell Delivery to Atheroma", Appellant Appeal Brief dated Jul. 23, 2015.
U.S. Appl. No. 12/749,219, "Multi-Functional Echogenic Immunoliposomes for Directed Stem Cell Delivery to Atheroma", Office Action—Examiner's Answer dated Dec. 31, 2015.
U.S. Appl. No. 12/749,219, "Multi-Functional Echogenic Immunoliposomes for Directed Stem Cell Delivery to Atheroma", Office Action—Transcript of Oral Hearing held Oct. 10, 2017, office action dated Nov. 7, 2017.
U.S. Appl. No. 12/749,219, "Multi-Functional Echogenic Immunoliposomes for Directed Stem Cell Delivery to Atheroma", Office Action—Decision on Appeal dated Dec. 4, 2017.
U.S. Appl. No. 12/749,219, "Multi-Functional Echogenic Immunoliposomes for Directed Stem Cell Delivery to Atheroma", Geng, McPherson, Klegerman Declaration (dated May 2013).
U.S. Appl. No. 12/749,219, "Multi-Functional Echogenic Immunoliposomes for Directed Stem Cell Delivery to Atheroma", Greer Declaration (dated May 10, 2013).

*Primary Examiner* — Robert M Kelly
(74) *Attorney, Agent, or Firm* — Parker Highlander PLLC

(57) ABSTRACT

Disclosed are multifunctional-echogenic immunoliposome (MF-ELIP) constructs and compositions, and their methods of use to deliver attached stem cells to a target tissue such as atheroma, to enhance one or more of survival, growth, migration, activity and differentiation of the targeted stem cells, for treating, deterring or preventing mammalian atheroma and coronary artery disease.

7 Claims, 28 Drawing Sheets

MULTI-FUNCTIONAL ECHOGENIC IMMUNOLIPOSOMES FOR DIRECTED STEM CELL DELIVERY TO ATHEROMA

CROSS-REFERENCE TO RELATED APPLICATION

This application is a continuation of U.S. application Ser. No. 12/749,219, filed Mar. 29, 2010, now abandoned, which claims benefit under 35 U.S.C. § 119(e) of U.S. Provisional Patent Application No. 61/164,238 filed Mar. 27, 2009, the entire disclosure of each of which is hereby incorporated herein by reference.

STATEMENT REGARDING FEDERALLY SPONSORED RESEARCH OR DEVELOPMENT

This invention was made with U.S. Government support under Grant Nos. R01 HL059586 and R01 HL074002 awarded by the National Institutes of Health/NHLBI, Grant No. R01 NS047603 awarded by the National Institutes of Health/NINDS, and under a DREAMS-DAMD 17-01-2-0047 and TS-W81XWH-04-02-0035 program awarded by the U.S. Department of Defense. The government has certain rights in the invention.

BACKGROUND

Technical Field

This disclosure generally relates to diagnosis and treatment of atherosclerosis and coronary artery disease, and more particularly to compositions and methods which selectively direct stem cells to arterial atheromas or a vascular tissue with altered surface antigens. More specifically, the disclosure relates to such compositions comprising multi-functional echogenic immunoliposomes, and to their methods of use, including immunoliposome-targeted delivery and imaging of stem cells.

Description of Related Art

Arteriosclerosis is a general term describing any hardening (and loss of elasticity) of medium or large arterial blood vessels characterized by the deposition of fatty substances, primarily cholesterol, cells (mostly macrophage), cell debris and subsequent fibrosis that results from a chronic inflammatory response at the site of the deposit in the artery, resulting in plaque deposition on the inner surface of the arterial wall and degenerative changes within it. Advanced atherosclerotic lesions are also referred to as atheroma. In the context of heart or artery matters, atheromata are commonly referred to as atheromatous plaques. It is an unhealthy condition, but is found in most humans and the process can eventually lead to plaque ruptures and stenosis (narrowing) of the artery and, therefore, an insufficient blood supply (ischemia) to the tissue or organ it supplies. Medical complications due to atherosclerosis can be slow to develop and progress but are cumulative.

Coronary heart disease (CHD) (or atherosclerotic coronary disease) is the leading cause of death worldwide and is the end result of the accumulation of plaques within the walls of the arteries that supply the myocardium (the muscle of the heart) with oxygen and nutrients. Advanced atherosclerotic plaques or atheroma are vulnerable and under stimulation of physical and chemical factors, they may suddenly rupture, which can cause the formation of a thrombus (clot). The plaque rupture-triggered thrombosis can rapidly slow or stop blood flow, leading to ischemia or infarction, i.e., a shortage of blood supply to the organs or tissues fed by the artery. Consequently, in a few minutes, the organ or tissue malfunctions and its structure destroyed. Such a catastrophic event is known as acute vascular syndrome. When it occurs in a coronary artery, it results in a myocardial infarction or heart attack. Since atherosclerosis is a body-wide process, similar events occur also in the arteries to the brain, intestines, kidneys, legs, etc. Another event experienced with CHD advanced disease is claudication from insufficient blood supply to the legs, typically due to a combination of both stenosis and aneurysmal segments narrowed with clots.

Ischemia is an absolute or relative shortage of the blood supply to a part of the body, when the blood supply is not sufficient to provide adequate oxygenation and the nutritional requirement of the tissue. Ischemia can also be described as an inadequate flow of blood to a part of the body, caused by constriction or blockage of the blood vessels supplying it. Ischemia can be temporary or sustained. For example myocardial ischemia is a temporary ischemia of the heart muscle and the cause of angina pectoris, whose symptoms result when the ischemic heart muscle does not function optimally or efficiently, but if the blood flow is improved myocardial ischemia can be reversed. Thus one must distinguish between myocardial ischemia and myocardial infarction. Ischemia can result from many things, including but not limited to tachycardia, atherosclerosis, hypotension, thromboembolism, sickle cell disease, external compression of a blood vessel or even g-forces. While many of these events result in transient ischemia, if complete ischemia is sustained it can result in cell and tissue necrosis and irreversible damage. The heart, kidneys, and brain are among the organs that are the most sensitive to inadequate blood supply and ischemia is a feature of heart diseases, transient ischemic attacks, cerebrovascular accidents (stroke), ruptured arteriovenous malformations, and peripheral artery occlusive disease.

Atherosclerosis causes vascular cell damage and apoptosis, leading to an increased vulnerability to plaque rupture and acute vascular syndromes. Currently, there are few clinically proven methods for stabilizing or reversing advanced, high risk atherosclerotic plaques (atheroma). During the development of atherosclerosis, there is an increase in expression of adhesion proteins or chemoattractive factor receptors on the endothelium covering atherosclerotic lesions of arteries, which can be recognized by mononuclear inflammatory cells or with specific antibodies.

In advanced, high risk atherosclerotic plaques or atheroma, there is a dramatic alteration in the contents of cellular components that characterize the inflammatory cell infiltration. In such infiltration there is vascular smooth muscle cell apoptosis and lipid-laden foam cell formation. Evidence from human and experimental studies has revealed the role of vascular stem cells in the maintenance of vascular wall integrity and regeneration during the development and advancement of atherosclerotic lesions. There is evidence that CD34+ stem cells can differentiate into endothelial cells and smooth muscle cells (Sata M, Saiura A, Kunisato A, Tojo A, Okada S, Tokuhisa T, Hirai H, Makuuchi M, Hirata Y, Nagai R, 2002. Hematopoietic stem cells differentiate into vascular cells that participate in the pathogenesis of atherosclerosis. Nat Med, 8:403-409). However, the stem cell-mediated vascular regeneration and repair is often hampered by increased stem cell death and malfunction caused by the exposure of the cells to pro-apoptotic factors such as cytokines and free radicals released by inflammatory cytokines and oxidized lipids from oxidized lipoproteins, as well as by aging. Vascular cells, in particular smooth muscle cells, play a central role in regulation of vascular function and morphology. The cap region of vulnerable atherosclerotic lesions is known to have fewer smooth muscle cells than that of stable plaques. Therefore, the delivery of sufficient numbers of stem cells into the plaque cap and maintenance of the cell biological function have been an important topic in the research of novel therapeutic approaches for atherosclerosis and its complications. Multipotent stem cells have been tested for their roles in regulation of the pathogenesis of atherosclerosis. Mesenchymal stem cells (MSC) are believed to be the major source for smooth muscle cell development and regeneration in adult tissues (Pontikoglou C, Delorme B, Charbord P, 2008. Human bone marrow native mesenchymal stem cells. *Regen Med,* 3:731-741).

However, CD34+ stem cells from the bone marrow of young mice have been shown to reduce atheroma in ApoE-null mice (Rauscher F M, Goldschmidt-Clermont P J, Davis B H, Wang T, Gregg D, Ramaswami P, Pippen A M, Annex B H, Dong C, Taylor D A 2003. Aging, progenitor cell exhaustion, and atherosclerosis. Circulation, 108:457-463).

It is known that CD34+ stem cells can differentiate into cells of the hematopoietic cell lineage and also to some degree endothelial cells, but these CD34+ hematopoietic cells do not appear to develop into inflammatory cells but rather vascular cells in the arterial wall. Accumulating literature suggests that loss of stem cells may lead to inflammation and atherogenesis (Goldschmidt-Clermont P J. 2003. Loss of bone marrow-derived vascular progenitor cells leads to inflammation and atherosclerosis. *Am Heart J,* 146:S5-12). However, little is known about the fates of stem cells which home and migrate into atherosclerotic lesions, and it is still debatable whether CD34$^+$ cells can actually differentiate into mature, functional VSMC.

It is known that atheroma is highly inflammatory and pro-apoptotic. Therefore, substantial numbers of vascular stem cells may die in these lesions through apoptotic or non-apoptotic death pathways, particularly because apoptosis has recently been shown to regulate the cellularity and morphogenesis in the arterial wall with atheroma. The apoptotic cascade in atherosclerotic lesions involves a complex interplay between micro environmental factors and endogenous genes, leading to activation of the proteolytic enzymes, caspases, which in turn cleave intracellular proteins and induce death. Two major pathways may participate in the regulation of vascular cell apoptosis: receptor-mediated activation of the caspase cascade, and; non-receptor-mediated mitochondrial dysfunction and caspase activation. The two pathways can occur independently or in combination during atherogenesis, and they can be activated by numerous pro-apoptotic factors, such as oxidized low density lipoproteins (oxLDL), oxysterols, and proinflammatory cytokines, or inhibited by anti-apoptotic factors (e.g., growth factors). Accelerated apoptosis of vascular cells in atheroma may reduce the strength and integrity of the arterial wall and provoke disruption of atherosclerotic plaques, a major cause of acute vascular syndromes and sudden death. There is continuing interest in developing new or better ways of treating and preventing atheroma and other pathological conditions that include altered vasculature.

SUMMARY

Constructs, compositions and methods are disclosed which provide or use multi-functional echogenic immunoliposomes (ELIP) to selectively target and deliver stem cells to atheroma to aid in imaging, repair and regeneration of the arterial wall damaged by atheroma, reduction of inflammation and apoptosis, and thereby stabilization of the vulnerable atheroma and/or promotion of its regression.

In accordance with certain embodiments, a multi-functional echogenic immunoliposome construct is provided that comprises: (a) an echogenic liposome; (b) at least a first and, second antibody attached to the liposome. The first antibody is capable of recognizing a first antigenic determinant on a stem cell, the second antibody is capable of recognizing a second antigenic determinant on an target tissue; (c) a stem cell bound to the first antibody and having at least a first antigenic determinant thereon. In some embodiments, when the construct receives a ultrasound stimulus the survival, activity or differentiation of the bound stem cell is enhanced. In some embodiments, the liposome further comprises a stem cell enhancing agent. In some embodiments, the liposome is formulated to release the agent upon receiving an ultrasound stimulus.

In accordance with certain embodiments, a multi-functional echogenic immunoliposome construct is provided that comprises: (a) an echogenic liposome, (b) at least a first, second and third antibody attached to the liposome. The first antibody is capable of recognizing a first antigenic determinant specifically expressed on a stem cell, the second antibody is capable of recognizing a second antigenic determinant specific to a target tissue, and the third antibody is capable of recognizing a third antigenic determinant on the target tissue, or is capable of recognizing a third antigenic determinant on the stem cell or is capable of recognizing a third antigenic determinant commonly expressed by both said stem cell and said target tissue. In some embodiments, the third antibody is specifically expressed on said stem cell or said target tissue.

In some embodiments, the construct further includes a stem cell bound to the first antibody and having at least a first antigenic determinant thereon. In some embodiments, when the construct receives an ultrasound stimulus the survival, activity or differentiation of the bound stem cell is enhanced. In some embodiments, the liposome further comprises a stem cell enhancing agent. In some embodiments, the liposome is formulated to release the agent upon receiving an ultrasound stimulus.

In accordance with certain embodiments, a multi-functional echogenic immunoliposome construct is provided that comprises: (a) an echogenic liposome; (b) at least a first, second and third antibody attached to the liposome. The first antibody is capable of recognizing a first antigenic determinant on a stem cell, the second antibody is capable of recognizing a second antigenic determinant on a target tissue, and the third antibody is capable of recognizing a third antigenic determinant on the target tissue, or is capable of recognizing a third antigenic determinant on the stem cell. In some embodiments, the construct further includes a stem cell bound to the first antibody and having at least a first antigenic determinant thereon. In some embodiments, when the construct receives an ultrasound stimulus the survival, activity or differentiation of the bound stem cell is enhanced. In some embodiments, the liposome further comprises a stem cell enhancing agent. In some embodiments, the liposome is formulated to release the agent upon receiving an ultrasound stimulus.

In accordance with certain embodiments, a method of treating a disease tissue in a patient suffering from a pathological condition is provided. The method comprises: (a) delivering to a disease tissue a construct comprising: (1) a stem cell having at least a first antigenic determinant; (2) an intrinsically echogenic liposome; and (3) at least a first and second antibody attached to the liposome, wherein the first antibody binds the first antigenic determinant on the stem cell, the second antibody is capable of binding a second antigenic determinant on the disease tissue, the stem cell being bound to the disease tissue through the construct by antibody-antigenic determinant recognition. In some embodiments, the method also includes (b) applying an ultrasound stimulus to the resulting tissue-attached construct. In some embodiments, the liposome is formulated to respond upon receiving the ultrasound stimulus. In some embodiments, the liposome further comprises a stem cell enhancing agent. In some embodiments, the liposome is formulated to release the stem cell enhancing agent upon receiving the ultrasound stimulus. In certain embodiments, the construct used in the method comprises a third antibody that is either capable of recognizing a third antigenic determinant on the target tissue or recognizes a third antigenic determinant on the stem cell. The third antibody is also attached to the liposome, the disease tissue expresses at least the second antigenic determinant, and the construct is attached to the disease tissue by antibody-antigenic determinant recognition between at least the second antibody-second antigenic determinant.

In accordance with certain embodiments, a method of treating a disease tissue in a patient suffering from a pathological condition is provided. The method comprises: (a) delivering to a disease tissue a construct comprising: (1) a stem cell having at least a first antigenic determinant; (2) an echogenic liposome; and (3) at least a first and second antibody attached to the liposome, wherein the first antibody binds the first antigenic determinant on the stem cell, the second antibody is capable of binding a second antigenic determinant on the disease tissue, the stem cell being bound to the disease tissue through the construct by antibody-antigenic determinant recognition. In some embodiments, the method also includes (b) applying an ultrasound stimulus to the resulting tissue-attached construct. In some embodiments, the liposome is formulated to respond upon receiving an ultrasound releasing stimulus that is different than an ultrasound imaging stimulus. In some embodiments, the liposome further comprises a stem cell enhancing agent. In some embodiments, the liposome is formulated to release the stem cell enhancing agent upon receiving the ultrasound stimulus. In certain embodiments, the construct used in the method comprises a third antibody that is either capable of recognizing a third antigenic determinant on the target tissue or recognizes a third antigenic determinant on the stem cell, or is capable of recognizing a third antigenic determinant that is shared by both said stem cell and said target tissue. The third antibody is also attached to the liposome, the disease tissue expresses at least the second antigenic determinant, and the construct is attached to the disease tissue by antibody-antigenic determinant recognition between at least the second antibody-second antigenic determinant.

In accordance with certain embodiments, a multi-functional echogenic immunoliposome construct is provided that comprises: (a) a liposome comprising a stem cell enhancing agent and at least one ultrasound reflecting material, wherein the liposome is formulated to release the agent upon receiving an ultrasound stimulus; and (b) at least a first, second and third antibody attached to the liposome. The first antibody is capable of recognizing a first antigenic determinant on the stem cell, the second antibody is capable of recognizing a second antigenic determinant on an target tissue, and the third antibody is capable of recognizing a third antigenic determinant on the target tissue, or is capable of recognizing a third antigenic determinant on the stem cell. In some embodiments, a construct disclosed herein further includes a stem cell having at least a first antigenic determinant thereon bound to the first antibody on the liposome. In some embodiments, the first antigenic determinant is specifically expressed in said stem cell.

In accordance with certain embodiments, a method of treating a disease tissue in a patient suffering from a pathological condition is provided. The method comprises: (a) delivering to a target tissue comprising the disease tissue a construct comprising: (1) a stem cell having at least a first antigenic determinant; (2) an echogenic liposome; and (3) at least a first and second antibody attached to the liposome, wherein the first antibody binds the first antigenic determinant on the stem cell, the second antibody is capable of binding a second antigenic determinant on the target tissue, and wherein the liposome is formulated to respond upon receiving an ultrasound stimulus, and the disease tissue expresses at least the second antigenic determinant, to bind the construct to the disease tissue by antibody-antigenic determinant recognition. In some embodiments, the liposome further comprises a stem cell enhancing agent. In some embodiments, the liposome is formulated to release the agent upon receiving the ultrasound stimulus. The method also includes (b) applying an ultrasound stimulus to the resulting tissue-attached construct to release the stem cell enhancing agent from the liposome. In certain embodiments, the construct used in the method comprises a third antibody that is either capable of recognizing a third antigenic determinant on the target tissue or recognizes a third antigenic determinant on the stem cell or is capable of recognizing a third antigenic determinant that is shared by both said stem cell and said target tissue. The third antibody is also attached to the liposome, the disease tissue expresses at least the second antigenic determinant, and the construct is attached to the disease tissue by antibody-antigenic determinant recognition between at least the second antibody-second antigenic determinant.

In certain embodiments, the construct used in the method comprises a third antibody that is either capable of recognizing a third antigenic determinant on the target tissue or recognizes a third antigenic determinant on the stem cell or is capable of recognizing a third antigenic determinant that is shared by both said stem cell and said target tissue. The third antibody is also attached to the liposome, the disease tissue expresses at least the second antigenic determinant, and the construct is attached to the disease tissue by antibody-antigenic determinant recognition between at least the second antibody-second antigenic determinant.

In accordance with certain other embodiments, a method of isolating stem cells that are useful in an above-described method is provided which includes: engaging a population of cells comprising stem cells from a mammalian embryonic or adult tissue with a plurality of multi-functional immunoliposome constructs. Each such construct comprises at least a first and second antibody attached to a liposome, wherein the first antibody is capable of recognizing a first antigenic determinant on the stem cell, the second antibody is capable of recognizing a second antigenic determinant on the stem cell, to obtain a mixture containing stem cell-bound immunoliposomes and unbound cells. This method further includes separating stem cell-bound immunoliposomes from the unbound cells (e.g., by sorting the mixture by gravity precipitation); and passing the resulting isolated stem cell-bound immunoliposomes thorough a flow cytometer, to obtain a defined population of stem cell-bound immunoliposomes. These and other embodiments, features and potential advantages will be apparent with reference to the following description and drawings.

DETAILED DESCRIPTION

Figure 1:
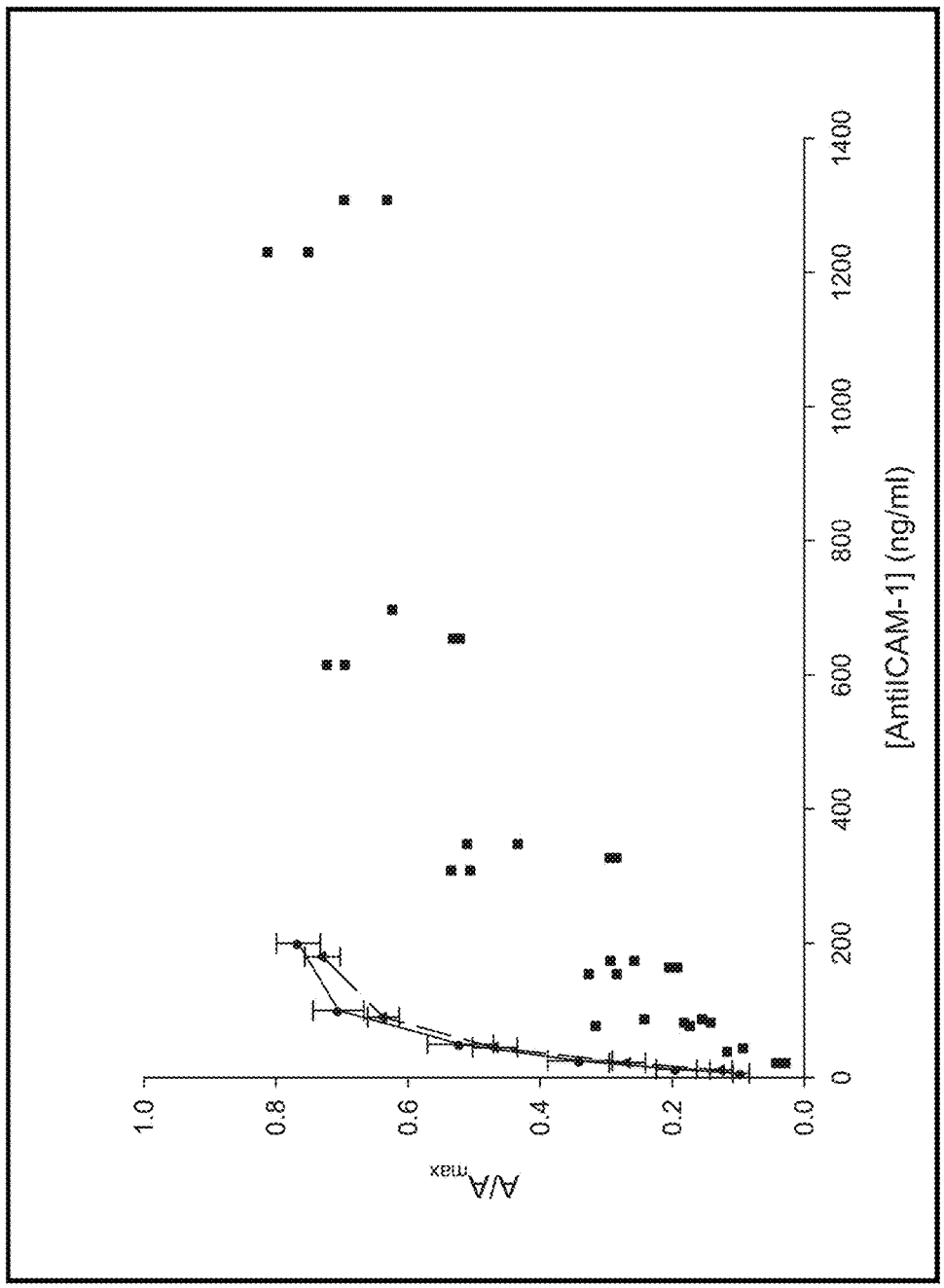
FIG. 1 shows the dose response curves obtained for three different lots of bifunctional-ELIP (squares) relative to the composite dose-response curve obtained with a control AICAMI-ELIP preparation (triangles) and an unconjugated antibody (Ab) standard (circles) as determined in a sandwich ICAM-1 ELISA

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or," unless specifically stated otherwise. Furthermore, the use of the term "including", as well as other forms, such as "includes" and "included," is not limiting. Also, terms such as "element" or "component" encompass both elements or components comprising one unit and elements or components that comprise more than one unit unless specifically stated otherwise.

As used herein, and unless otherwise indicated, the terms "treat," "treating," and "treatment" contemplate an action that occurs while a patient is suffering from atheroma that reduces the severity of one or more symptoms or effects of atheroma, or a related disease or disorder. As used herein, and unless otherwise indicated, the terms "prevent", "preventing", and "prevention" contemplate an action that occurs before a patient begins to suffer from atheroma, that prolongs the onset of, and/or inhibits or reduces the severity of, atheroma. As used herein, and unless otherwise indicated, the terms "manage," "managing," and "management" encompass preventing, delaying, or reducing the severity of a recurrence of atheroma in a patient who has already suffered from such a disease or condition. The terms encompass modulating the threshold, development, and/or duration of the atheroma or changing how a patient responds to the atheroma.

As used herein, and unless otherwise specified, a "therapeutically effective amount" of a compound is an amount sufficient to provide any therapeutic benefit in the treatment or management of atheroma or to delay or minimize one or more symptoms associated with atheroma. A therapeutically effective amount of a compound means an amount of the compound, alone or in combination with one or more other therapy and/or therapeutic agent, that provides any therapeutic benefit in the treatment or management of atheroma, or related diseases or disorders. The term "therapeutically effective amount" can encompass an amount that cures atheroma, improves or reduces atheroma, improves overall therapy, or enhances the therapeutic efficacy of another therapeutic agent.

As used herein, and unless otherwise specified, a "prophylactically effective amount" of a compound is an amount sufficient to prevent or delay the onset of atheroma, or one or more symptoms associated with atheroma or prevent or delay its recurrence. A prophylactically effective amount of a compound means an amount of the compound, alone or in combination with one or more other treatment and/or prophylactic agent that provides a prophylactic benefit in the prevention of atheroma. The term "prophylactically effective amount" can encompass an amount that prevents atheroma, improves overall prophylaxis, or enhances the prophylactic efficacy of another prophylactic agent.

The term "bifunctional echogenic immunoliposome" (BF-ELIP) refers to a liposome with two different antibodies attached to its surface. Each antibody is directed against a respective antigen or antigenic determinant, and, when attached to the liposome, is capable of recognizing (i.e., binding) the respective antigen or antigenic determinant. The liposome is echogenic in that it contains a gas, an ultrasound contrast reagent or other ingredient that renders the liposome echogenic or it may be intrinsically echogenic, for example, but not limited to, as the result of air trapped during vacuum release following freezing and lyophilization in the presence of mannitol during a freeze drying process.

The term "multi-functional echogenic immunoliposome" (MF-ELIP) refers to a liposome with two or more different antibodies attached to its surface. Each antibody is directed against a respective antigen or antigenic determinant, and, when attached to the liposome, is capable of recognizing (i.e., binding) the respective antigen or antigenic determinant. The liposome is echogenic, in that it contains a gas, an ultrasound contrast reagent or other ingredient that renders the liposome reflective of ultrasound waves ("echogenic"), or it may be intrinsically echogenic. As a non-limiting example, a liposome may be echogenic as the result of air trapped during vacuum release following freezing and lyophilization in the presence of mannitol during a freeze drying process.

The term "stem cell enhancing agent" refers to an agent that increases at least one of the following: survival, growth, migration, activity and differentiation of a stem cell.

Overview

Atherosclerosis is characterized by increased expression in endothelial cells of adhesion proteins such as intercellular adhesion molecule-1 (ICAM-1) and vascular cell adhesion molecule-1 (VCAM-1), both of which recruit monocytes and induce their migration through the endothelium and into the intima of the arterial wall to accumulate lipid. VCAM-1 expression declines as the atheroma progresses, while ICAM-1 expression persists. Endogenous stem cells adhere to the surface via the adhesion proteins before entering the arterial wall. The conjugation of anti-ICAM-1 antibodies to the surface of liposomes allows binding of liposomes to ICAM-1-expressing endothelial cells of atherosclerotic lesions, thereby specifically targeting cells involved in early plaque formation. In addition, selection of specific types of stem cells can be achieved through liposomal conjugation of antibodies against cell-type specific surface markers. MSCs are characterized by several cell-surface markers, including but not limited to CD29, CD34, CD44, and CD90. Double-conjugation of echogenic liposomes to both ICAM-1 and stem-cell-specific surface markers to produce bifunctional echogenic liposomes provides a mechanism to allow binding of stem cells to ICAM-1-expressing endothelial cells.

In certain embodiments the multi-functional-ELIP includes two different immunoreactions; one occurs between an antibody or antibodies attached to the liposome and an antigenic determinant(s) on stem cells and other one occurs between an antibody or antibodies attached to the liposome and an antigenic determinant on a target tissue. Each antibody is directed against a respective antigen or antigenic determinant, and, when attached to the liposome, is capable of recognizing (i.e., binding) the respective antigen or antigenic determinant. The liposome is echogenic in that it contains a gas, an ultrasound contrast reagent or other ingredient that renders the liposome echogenic or it may be intrinsically echogenic, for example, but not limited to, as the result of air trapped during vacuum release following freezing and lyophilization in the presence of mannitol during a freeze drying process. The liposome can also contain other bioactive substances (e.g., drug, DNA segment, protein, biotherapeutic, drug, lipid, or gas) that can modulate the function and morphology of stem cells or target tissue cells, including the biological activities of inhibition of inflammation and apoptosis.

The certain embodiments the multi-functional ELIP can includes a liposome with more than two different antibodies attached to its surface. Each antibody is directed against a respective antigen or antigenic determinant, and, when attached to the liposome, is capable of recognizing (i.e., binding) the respective antigen or antigenic determinant. The liposome is echogenic in that it contains a gas, an ultrasound contrast reagent or other ingredient that renders the liposome echogenic or it may be intrinsically echogenic, for example, but not limited to, as the result of air trapped during vacuum release following freezing and lyophilization in the presence of mannitol during a freeze drying process. The liposome can also contain other bioactive substances (e.g., drug, DNA segment, protein, biotherapeutic, drug, lipid, or gas) that can modulate the function and morphology of stem cells or target tissue cells, including the biological activities of inhibition of inflammation and apoptosis.

Certain embodiments comprise intrinsically echogenic liposomes (ELIP) as both an ultrasound contrast agent and an ultrasound-inducible controlled release delivery vehicle, targeted to various tissue markers by covalent attachment of ligands to the phosphatidylethanolamine head groups, enabling site-specific ultrasound highlighting or delivery of therapeutic agents, including drugs, genes, and bioactive gases. Ultrasound has the ability to enhance and provide controlled delivery of therapeutics at the target site. This methodology, known as sonoporation, can be augmented by small air or gas pockets within the delivery vehicle (ultrasound-induced cavitation).

In an exemplary embodiment, the ability of low level ultrasound to enhance the delivery of stem cells into the arterial wall using bifunctional antibody targeted-ELIP, is improved by producing multifunctional antibody targeted-ELIP that serve as an appropriate delivery vehicle, by binding both immobilized ICAM-1 and CD34⁻ human peripheral stem cells. With multifunctional embodiments the inclusion of one or more additional antibodies that recognizes the target atheroma (or tumor) or the stem cell, allows fine tuning of the targeting of multifunctional antibody targeted-ELIP and/or blocking of sites, such as CXCR4, that can cause diversion of the stem cells from their intended target(s).

Stem Cells Used for Vascular Tissue Repair in Atherosclerosis.

Vascular stem cells (VSC) are a group of undifferentiated cells responsible for neovascularization and angiogenesis during embryonic development or adult tissue repair and regeneration. VSC exist in both embryonic and adult tissues with certain biomarkers for endothelial and vascular (or mesenchymal) cell lineages and are responsible for the regeneration and repair of vascular tissue under a variety of physiological and pathophysiological conditions. (Anversa P, Kajstura J, Nadal-Ginard B, Leri A, 2003. Primitive cells and tissue regeneration. *Circ Res,* 92:579-582; Anversa P, Kajstura J, Leri A, 2004. Circulating progenitor cells: search for an identity. *Circulation,* 110:3158-3160). Vascular cells, in particular smooth muscle cells, play a central role in regulation of vascular function and morphology. VSC phenotypes can be characterized by flow cytometry with antibodies against specific markers for endothelial cells (e.g., Flk1, Tie2, CD31, VE-adherin) and smooth muscle cells (e.g., alpha-SM-actin, SM-tropmyosin, desmin and alpha-actinin). Healthy vascular stem cells are required to maintain the vascular tissue integrity and homeostasis. Accumulating literature suggests that loss of stem cells may lead to inflammation and atherogenesis. The cap region of vulnerable atherosclerotic lesions is known to have fewer smooth muscle cells than the cap region of stable plaques.

In certain embodiments, the transfer of external stem cells into atheroma is used to compensate for the stem cell loss that occurs in atheroma, and the transfer is facilitated by using a new stem cell delivery system is employed which uses echogenic liposome technology, as described in more detail below. In some embodiments, this includes coupling of ELIP loaded with apolipoprotein-J (ApoJ) and tetracycline (TCN) to facilitate SC survival, growth and differentiation into vascular smooth muscle cells (VSMC). It is proposed that targeted SC delivery with bifunctional or multi-functional ELIP promotes adhesion and migration of vascular stem cells into atherosclerotic arterial wall.

Atherosclerosis is a major cause of ischemic heart disease. Late-stage, vulnerable atheroma contains fewer vascular smooth muscle cells (VSMC) that tend to counteract inflammatory processes leading to plaque rupture and thrombosis. Vascular stem cells (VSC) have been shown to play an important role in stabilizing atheroma, but the inflammatory, oxidative environment of vulnerable atheroma has hampered the survival of therapeutically introduced VSC.

In some embodiments, echogenic liposomes (ELIP) as targeted vehicles for ultrasound-induced delivery of therapeutic agents are provided. Some embodiments of the new ELIP selectively deliver VSC to vulnerable atheroma, while providing controlled release of agents that enhance VSC endothelial penetration and amelioration of the inflammatory environment. In some embodiments, bifunctionally targeted ELIP are provided that will serve as an appropriate delivery vehicle by binding both immobilized ICAM-1 on the target tissue (atheroma) and CD34+ human peripheral stem cells.

Liposomes

Liposome technology is used for targeted delivery of stem cells. For example, in some embodiments, liposomes are loaded with a specific antibody, gene or drug that improves stem cell survival, growth, migration, activity or differentiation in atheroma. A liposome is a spherical vesicle composed of a bilayer membrane. In biological liposomes, the bilayer membranes are composed of a phospholipid and cholesterol bilayer. Liposomes can be composed of naturally-derived phospholipids with mixed lipid chains (like egg phosphatidylethanolamine), or of pure surfactant components like DOPE (dioleoylphosphatidylethanolamine). Liposomes contain a core of aqueous solution. Lipid spheres that contain no aqueous material are called micelles; however, reverse micelles can be made to encompass an aqueous environment. Liposomes can be used for drug delivery as they can encapsulate a region of aqueous solution inside a hydrophobic membrane. Dissolved hydrophilic solutes liposomes cannot readily pass through the lipids.

Hydrophobic chemicals can be dissolved into the membrane, and in this way liposome can carry both hydrophobic molecules and hydrophilic molecules. Liposomes can be used to deliver specific molecules to a site of action; the contents of the liposome are delivered within the target cell when the lipid bilayer of the liposome fuses with the bilayer of the cell membrane. Construction of liposomes in a solution facilitates loading of the liposome with the solution. Thus solutions containing DNA or a drug that normally would not diffuse through the cell membrane, can be delivered past the cell membrane when the lipid bilayer of the liposome fuses with the cell membrane. In some embodiments, liposome technology is used to target and deliver stem cells, to a specific target, by loading the liposomes with, for example, a specific antibody, gene or drug that improves stem cell survival, growth and differentiation in atheroma.

Use of ELIP to Facilitate Molecular Imaging and the Targeting of Drugs, Genes and Stem Cells to Atheroma Alone or in Combination.

Ecogenic immunoliposomes (ELIP) are used to target delivery of drugs and genes and for ultrasound detection and enhancement of vasoactive and pathologic molecular components of endothelium and atheroma. Certain ELIP are described in U.S. Pat. Nos. 5,612,057 and 5,858,399, as well as U.S. Patent Application Publication Nos. 2008/0175893 and 2008/0305156, for example. These ELIP are small (<1 μm) intrinsically echogenic ultrasound contrast agents, and can be used to evaluate molecular and cellular components of atheroma. Currently available ELIP are composed of four primary lipids: phosphatidylcholine (PC), phosphatidylethanolamine (PE), phosphatidylglycerol (PG), and cholesterol (CH) and are made using a lyophilization process. Once produced, ELIP is conjugated to specific antibodies that enable targeted ultrasound enhancement of molecular components of atheroma and other tissues. Detection of molecular components may allow staging of atheroma and lead to the development of targeted therapeutic interventions. The endothelial surface of atherosclerotic plaques, molecules shows increased expression of adhesion proteins, including vascular cell adhesion molecule-1 (VCAM-1) and intercellular adhesion molecule-1 (ICAM-1). In the early stages of plaque formation, monocytes are recruited to the injured EC by VCAM-1, an important marker of endothelial cell activation. VCAM-1 is expressed on the endothelium of mid-stage atheroma, and its expression declines as atheroma progresses. ICAM-1 has been shown to enhance recruitment of circulatory monocytes and is expressed on the surface of the endothelium in early-stage atheroma. Stem cells adhere to the surface via the adhesion proteins before they enter the arterial wall. The ELIP with dual antibodies to stem cell markers and adhesion proteins can be used to bridge VSC to atheroma. In addition, the echogenicity of ELIP allows targeted release of atheroma modulators (therapeutics) from ELIP following ultrasound application. When stem cells enter the atheroma, however, they may confront a very harsh microenvironment in which a large quantity of pro-inflammatory and pro-apoptotic factors are generated. Accelerated apoptosis occurs in atherosclerotic lesions, triggered by a variety of environmental insults and endogenous gene alterations. For instance, oxidized lipids and proinflammatory cytokines are all known to induce vascular cell apoptosis in atheroma. Therefore, stem cells in an atheroma are exposed to very harsh environment and prone to undergo higher levels of apoptosis. Accordingly, in at least some embodiments, a stem cell therapy method for treating atheroma includes maintenance of viability.

Multi-Functional-ELIP.

Multi-functional-ELIP which are coupled to stem cells have the added advantage that they facilitate molecular imaging as well as the targeting of drugs, genes and proteins that can increase the survival, activity or differentiation of stem cells that have been delivered to atheroma. For example, anti-apoptotic treatment with ApoJ can be used to increase the efficacy of stem cell treatment in cardiovascular disease (as described in U.S. Patent Application Publication No. 2006/0099194 (now U.S. Pat. No. 7,524,490). ApoJ also known as clusterin, is a sulfated, heterodimeric glycoprotein containing two 40 kDa chains joined by a unique five disulfide bond motif. Encoded on a 2-kb mRNA, ApoJ is transcribed from a single copy gene located on mouse chromosome 14 and human 8p21 in proximity to the lipoprotein lipase (LPL) gene and translated as a typical hydrophobic signal peptide with 21 amino acids in length. ApoJ has a unique structure with high-affinity to a wide array of biological ligands and contains both hydrophilic and hydrophobic domains, thereby referred to as a "biological detergent". ApoJ circulates mainly with the HDL fraction and is thus considered as a component of HDL. However, very recently, ApoJ has been also found in LDL. Increased expression of ApoJ has been demonstrated in both human and experimental animal atheromas. ApoJ has multiple biological activities similar to that of heat shock proteins and acts as a chaperone that mediates lipid transport as well as prevents protein denaturation. Reported functions of ApoJ include apoptosis regulation, complement factor inactivation, lipid recycling and transport, membrane protection, and maintenance of cell-cell or cell-substratum contacts. It can effectively bind to lipids and promote efflux of cholesterol and oxysterols from lipid-laden foam cells. ApoJ protein can also inhibit complement-mediated cell death and promote cell aggregation and adhesion. Recently, ApoJ has been determined to be an anti-apoptotic protein. ApoJ expression reportedly confers resistance to apoptotic cell death induced by heat shock and oxidative stress. High levels of ApoJ have been shown in tissues with apoptosis. However, careful analysis of the producing cells revealed that ApoJ expression is restricted to the vital cells adjacent to dead cells, suggesting that this molecule may act as a cell survival factor, which protects bystander cells. In addition, in ApoJ knockout mice, the hearts become vulnerable to autoimmune-associated inflammation, suggesting an anti-inflammatory role for ApoJ. ApoJ can also promote clustering of vascular smooth muscle cells, an event critical for smooth muscle differentiation of stem cells Use of Targeted MF/BF-ELIP in Combination with Ultrasound to Deliver ApoJ Gene Together with Stem Cells Directly to Atheroma Thereby Enhancing Stem Cell Survival, Activity and Differentiation into Smooth Muscle Cells, that Will Stabilize Atheroma.

In some embodiments, by inserting the ApoJ cDNA construct into an expression vector controlled by a tetracycline (TCN) regulatory element, selective expression of ApoJ in VSC can be achieved by treatment with ELIP loaded with TCN or its analogs. Unique multifunctional or bifunctional-ELIP were generated that link two or more distinct antibodies, one or more that binds to stem cell markers and the other one or more that binds to activated endothelial cell markers. These MF/BF-ELIP functions as a bridge that links stem cells to the activated endothelium that covers inflamed rupture-prone atheroma. The attachment and migration of MF/BF-ELIP coupled stem cells to endothelium was further enhanced by ultrasound treatment.

Two types of exemplary MF/BF-ELIP were produced: the first one was anti-CD34/ICAM-1 BF-ELIP for delivery of CD34+ endothelial cell progenitors (EPCs) to atheroma; and the second one was anti-CD146/ICAM-1 BF-ELIP for delivery of CD146+ mesenchymal stem cells (MSC) to atheroma. In vitro and ex vivo experiments were performed using these BF-ELIP/MSC or VSC treatment with or without ultrasound enhancement.

In these experiments, the technology of ultrasound bifunctional antibody targeted-ELIP-coupled stem cell delivery was combined with the strategy of ApoJ gene expression. ApoJ was selected as the target gene delivery for its ApoJ protective effects on stem cells and also can induce expression of chemokine receptors while increasing stem cells response to SDF-1, a key chemokine regulating VSC homing and migration. To demonstrate that ApoJ can promote differentiation of MSC into VSMC and thereby stabilize the arterial wall with atheroma.

In some embodiments, biosafety and efficacy of multifunctional (MF-ELIP) targeted delivery of MSC and VSC to inflammatory atherosclerotic lesions will be satisfactory for clinical applications. In vivo studies were conducted by delivering stem cells to ApoE-null, atheroma-prone mice to investigate in vivo effects of BF-ELIP-aided stem cell delivery. It is proposed that targeted delivery of stem cells may help heal the vascular lesions and increase integrity of the arterial wall. Toward that goal, a BF-ELIP-TCN delivery system will be used to activate the ApoJ transgene, while inhibiting osteogenesis and calcification of MSC in atheroma-prone ApoE mice.

MF/BF-ELIP-TCN Delivery System, and Use of this System to Activate the ApoJ Transgene, while Inhibiting Osteogenesis and Calcification of MSC in Atheroma-Prone ApoE Mice.

Osteogenesis and calcification frequently occur in advanced atherosclerotic lesions. The antibiotic tetracycline (TCN) has been shown to inhibit osteogenesis and calcification (Maniscalco and Taylor, 2004) and aneurysm formation (Thompson et al., 1998) in atheroma. Therefore, to potentially prevent osteogenesis of multipotent MSC and promote their differentiation into SMC, targeted delivery of MSC to inflammatory atherosclerotic lesions via MF/BF-ELIP along with TCN or its derivatives are used in some embodiments to inhibit osteogenesis and to facilitate the differentiation of MSC into VSMC.

Examples

It has been shown that vascular cell injury and death is a key factor that contributes to plaque instability and vulnerability to rupture. As the major cell types of the arterial tissue, smooth muscle cells and endothelial cells play a key role in maintaining contractility and integrity of the arterial wall vascular cell loss triggered by apoptosis may substantially weaken the vessel wall and increase the risk of plaque rupture, an event that causes acute vascular syndromes, including myocardial infarction. Therefore, it is important to increase the number of stem cells, promote their proliferation and repopulation within the vessel. In some embodiments, a system of treating atheroma is provided utilizing the MF/BF-ELIP-ultrasound system, a novel technology to target delivery of vascular stem cells to advanced, rupture-prone atherosclerotic lesions. Furthermore, in some embodiments, drugs, DNA compounds or other molecules are delivered to atheroma by loading them into the MF/BF-ELIP.

As an example, ApoJ, a protective protein which has anti-apoptotic, anti-inflammatory and antioxidant properties is a factor which not only protects stem cells but also promotes their migration in response to SDF-1, a major chemokine that regulates homing and traffic of stem cells.

1.1 Bridging of MSC or VSC to Endothelium Using BF-ELIP Increases the Efficacy of MSC Entry into Inflammatory Atherosclerotic Lesions.

MSC were isolated and cultured from bone marrow and adipose tissue. Flow cytometric analysis was used to identify and verify MSC populations. Bone marrow-derived cells were isolated, cultured, and analyzed for the presence of MSC-specific markers: through reaction with labeled antibodies directed at CD29, CD44, and CD90 and for the hematopoietic stem cell (HSC) marker CD45 and an endothelial marker, von Willebrand's factor (vWF). The MSC populations were positive for reactivity with antibodies directed at all three MSC markers, but no negative for reactivity with antibodies directed at the HSC or endothelial markers.

After labeling with antibody-coated ELIP, MSCs were tested for their capacity of adhesion and penetration through the endothelial cell monolayer under ultrasound enhancement. In vitro and ex vivo experiments were performed using cell migration assay kits and the aortic segment cultures. Similar work was performed for comparison in the capacity of vascular tissue regeneration between undifferentiated MSC and partially differentiated VSC.

The following findings establish that bridging of stem cells to endothelium using echogenic MF-ELIP conjugated with multifunctional antibodies increases the transmigration capacity and efficacy of stem cell entry into inflammatory atherosclerotic lesions.

ELIP Formulation and Preparation.

ELIP were prepared by the dehydration-lyophilization-rehydration method as described previously, see for example, among others, U.S. Pat. Nos. 5,612,057 and 5,858,399, as well as the published U.S. patent application nos. 20080175893 and 20080305156. The procedure for producing an echogenic lipid dispersion, as opposed to a normal liposome preparation, involves the addition of lyophilization in the presence of the sugar, mannitol. Thus, liposomes are normally made by adding buffer to a dry film of lipid in a flask and then dispersing the hydrated lipid. However to prepare echogenic liposomes, mannitol (to a few tenths molar) is added and the preparation is frozen and lyophilized.

The ELIP composition consisted of egg PC:DPPE:DPPG:CH in a 69:8:8:15 molar ratio (PC, phosphatidylcholine; DPPE, dipalmitoylphosphatidylethanolamine; DPPG, dipalmitoylphosphatidylglycerol; CH, cholesterol). For rhodamine (Rh) labeling, Rh-DPPE was added at a molar ratio of 0.02. All phospholipids were purchased from Avanti Polar Lipids (Alabaster, Ala.). The component lipids were dissolved in chloroform and the solvent was allowed to completely evaporate. The resulting lipid film was placed under vacuum for complete drying and then rehydrated with distilled, deionized water. This dispersion was sonicated until an approximate average vesicular diameter of 500 nm was obtained; 0.2 M D-mannitol was added to the liposome suspension and the sample was frozen at −70° C. The samples were lyophilized for 48 hours and resuspended with 0.2 micron-filtered and deionized water.

1.2 Evidence of the Activity of Antibody Targeted Echogenic Immunoliposomes as Demonstrated Using Bifunctional Echogenic Immunoliposomes.

To establish the activity of multi-functional antibody targeted ELIP, it was first established that two antibodies could be bound to ELIP and that they would have the desired activity. Bifunctional ELIP were prepared by conjugating ELIP to a monoclonal antibody (MAb) to human/mouse ICAM-1 and a rabbit polyclonal Ab to human/mouse CD34 (EPC antigen) or CD146 (pericyte antigen) (Santa Cruz Biotechnology, Santa Cruz, Calif.; with 80% nonspecific carrier IgG to provide an optimal initial IgG mass of 2 mg/29 mg ELIP lipid). IgG reacts with 3-(2-pyridyldithiolpropionic acid)-N-hydroxysuccinimide ester (SPDP) at a SPDP-protein molar ratio of 15:1 for 30 min at room temperature (RT). Protein was separated from unreacted SPDP by gel chromatography on a 50 ml Sephadex G-50 column equilibrated with 0.05 M citrate-phosphate buffer, pH 5.5. Protein fractions were identified (optical absorbance at 280 nm, A280), pooled and concentrated to ≤2 ml using Centricon YM-10 centrifugal filter units. The PDP-protein was reduced in 25 mM dithiothreitol (DTT) for 30 min at RT. The thiolated protein was isolated (G-50 column), equilibrated and eluted with pH 6.7 citrate-phosphate buffer. Protein-containing fractions were pooled and concentrated. The purified thiolated protein then reacts with reconstituted N-[4-(p-maleimidophenyl) butyrate (MPB-ELIP) (10 mg lipid/ml 0.1 M phosphate buffer, pH 6.62) under argon overnight at room temperature. Eight (8) lots of BF-ELIP targeted to CD34+ hematopoietic stem cells and 1 lot to CD146+ mesenchymal stem cells were prepared. Composite ICAM-1 targeting parameters for all these lots are summarized in Table 1.

TABLE 1

Composite ICAM-1 Targeting Parameters (Mean ± S.E. (n)) for BF-ELIP Lots

| Conj. Efficiency | | | | Specific | Specific | Functional |
|---|---|---|---|---|---|---|
| µg anti-ICAM-1/mg lipid | Ab mol./ELIP ($\times 10^{-3}$) | $K_D$ (nM Ab) | $K_{assoc}$ ($M^{-1} \times 10^{-8}$) | Avidity ($M^{-1}$/ ELIP $\times 10^{-12}$) | Targeting Efficiency (No./ELIP) | Avidity ($M^{-1}$/ ELIP $\times 10^{-10}$) |
| 2.44 ± 0.19 (9) | 1.56 ± 0.59 (8) | 1.44 ± 0.25 (9) | 8.33 ± 1.36 (9) | 1.31 ± 0.66 (8) | 53.2 ± 32.8 (8) | 6.15 ± 3.88 (8) |

ICAM-1 binding of the BF-ELIP was verified using a sandwich ICAM-1 ELISA (results shown in FIG. 1. The mean affinity was nearly as great as that exhibited by the unconjugated Ab and the mean specific avidity was greater than what we consider to be the threshold for optimal targeting. Ab-ELIP specific for human/mouse ICAM-1 and CD34 or CD146 were examined for its pharmacokinetics (Table 1). The conjugation efficiency (CE) of IgG was 22.2 pg/mg lipid ($5.52 \times 10^4$ molecules/LIP), while ELIP echogenicity was fully retained. The median spherical equivalent diameter of the BF-ELIP was found to be 817 nm. ICAM-1 binding of the BF-ELIP was verified by a sandwich ICAM-1 ELISA. Affinity for ICAM-1 was about 1.0 nM (KD).

Figure 32:
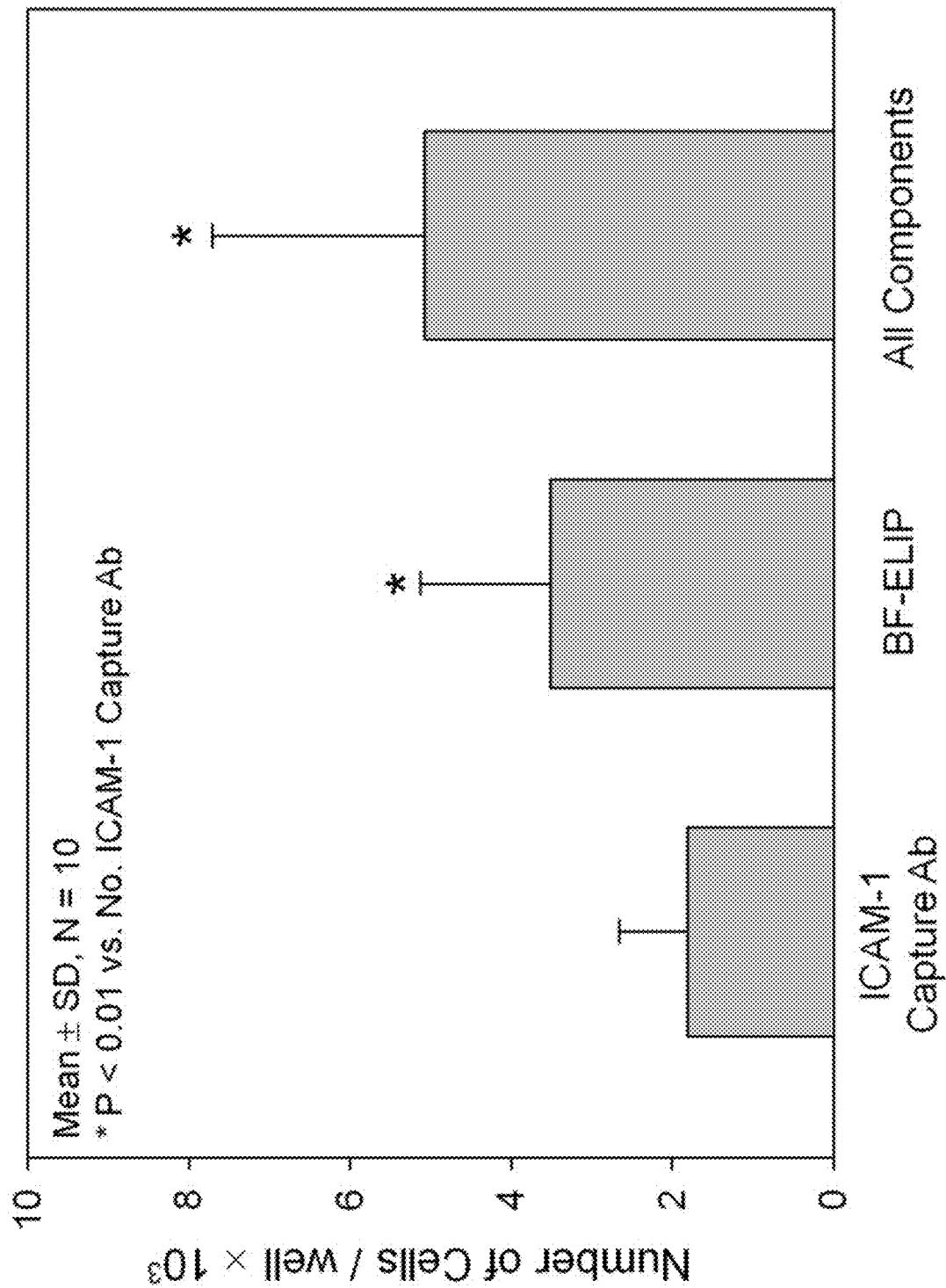
FIG. 32 shows BF-ELIP bridging of human ICAM-1 and CD34+ human monocytes, demonstrated by enumeration of adsorbed cells in a modified ELISA protocol. Bars=SD, n=10.

The first ELISA protocol demonstrated an ability of BF-ELIP to promote net binding of human monocytes to an ICAM-1 matrix. In the presence of BF-ELIP, more monocytes were recovered from the wells with the ICAM-1 matrix (FIG. 32), which mimics the surface of activated endothelial cells.

1.3 Bifunctional-ELIP Bind Selectively to CD34 Protein and to CD34+ Cells.

To establish that antibody targeted ELIP maintained their selectivity we sought to verify that BF-ELIP bind to CD34 Protein and to CD34+ cells. To do this CD34+ human umbilical vascular endothelial cells (HUVEC) were cultured in collagen-coated 96-well microplates. Human blood mononuclear cells were transfected with an adenovirus vector incorporating the green fluorescent protein (GFP) gene. Bifunctionality of the preparation was demonstrated by: 1) counting of cells adsorbed to BF-ELIP in the ICAM-1 ELISA protocol, and 2) successive incubation of adherent HUVEC with BF-ELIP, HMNC and a phycoerythrin (PE)-labeled anti-CD34 antibody (antiCD34-PE). Characteristic PE and GFP fluorescent emission intensities were measured.

Figure 2:
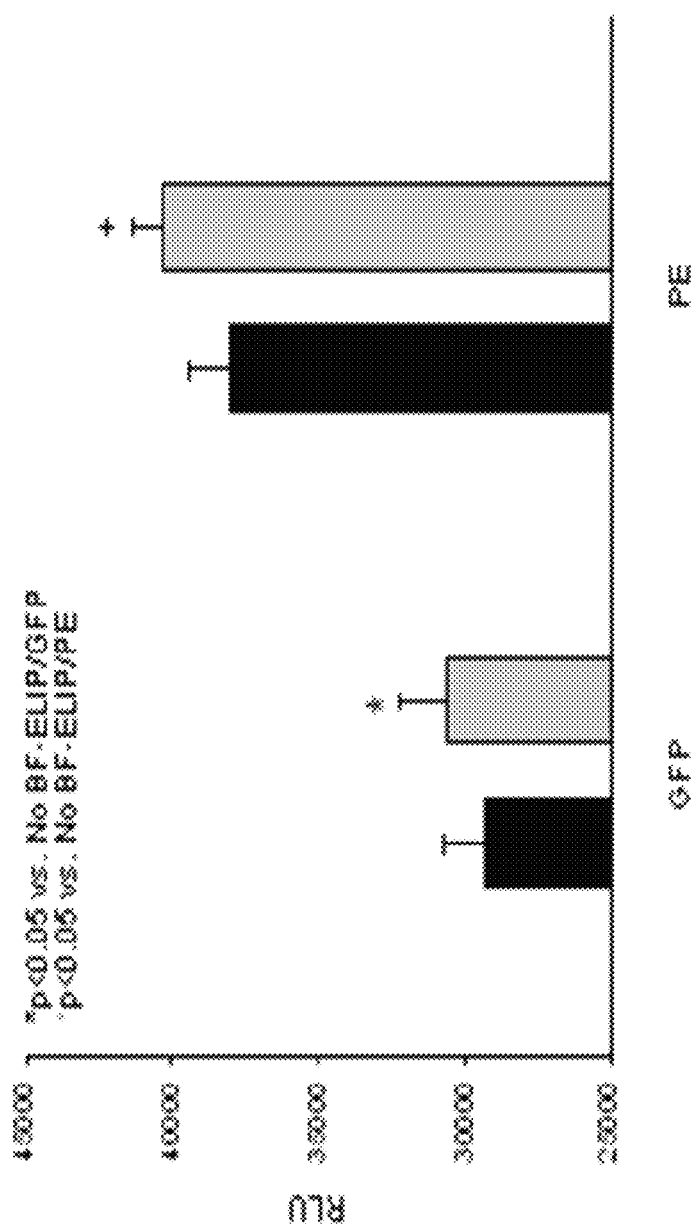
FIG. 2 shows that the presence of bifunctional antibody targeted-ELIP containing antibodies to ICAM-1 and phycoerythrin (PE)-labeled anti-CD34 antibody were able to significantly increase the bridging of GFP labeled cells. GFP (n=10); PE (n=3). Black bars=no BF-ELIP; Gray bars=BF-ELIP. Black/Gray p<0.05.

The ability of bifunctional antibody targeted-ELIP to promote net HMNC binding to an ICAM-1 matrix ($5.07 \times 10^3$ vs. $3.51 \times 10^3$ cells per well) was verified (results shown in FIG. 2).

The bifunctional antibody bearing ELIP were also determined to selectively bind and bridge HUVEC and HMNC and an ICAM-1 matrix, as demonstrated by the significant enhancement of both PE and GFP fluorescence in cells treated with labeled bifunctional antibody targeted-ELIP as compared to the control group which did not include bifunctional antibody targeted-ELIP ($p<0.05$; PE n=3; GFP n=10) (FIG. 2).

The binding of CD34 by bifunctional antibody targeted-ELIP was confirmed when it was determined that these antibody targeted ELIP, coated with anti-CD34 antibodies bound to human peripheral blood mononuclear cells that bear CD34+. Human PBMC were isolated by Ficoll-Paque density gradient centrifugation (Sigma) and incubated with the CD34 antibody targeted-ELIP and control IgG-ELIP. After incubation, cells were gently washed with PBS using low speed centrifugation, and then fixed in 4% paraformaldehyde. Cells were smeared on a glass slide and mounted in DAPI-containing media.

Figure 3:
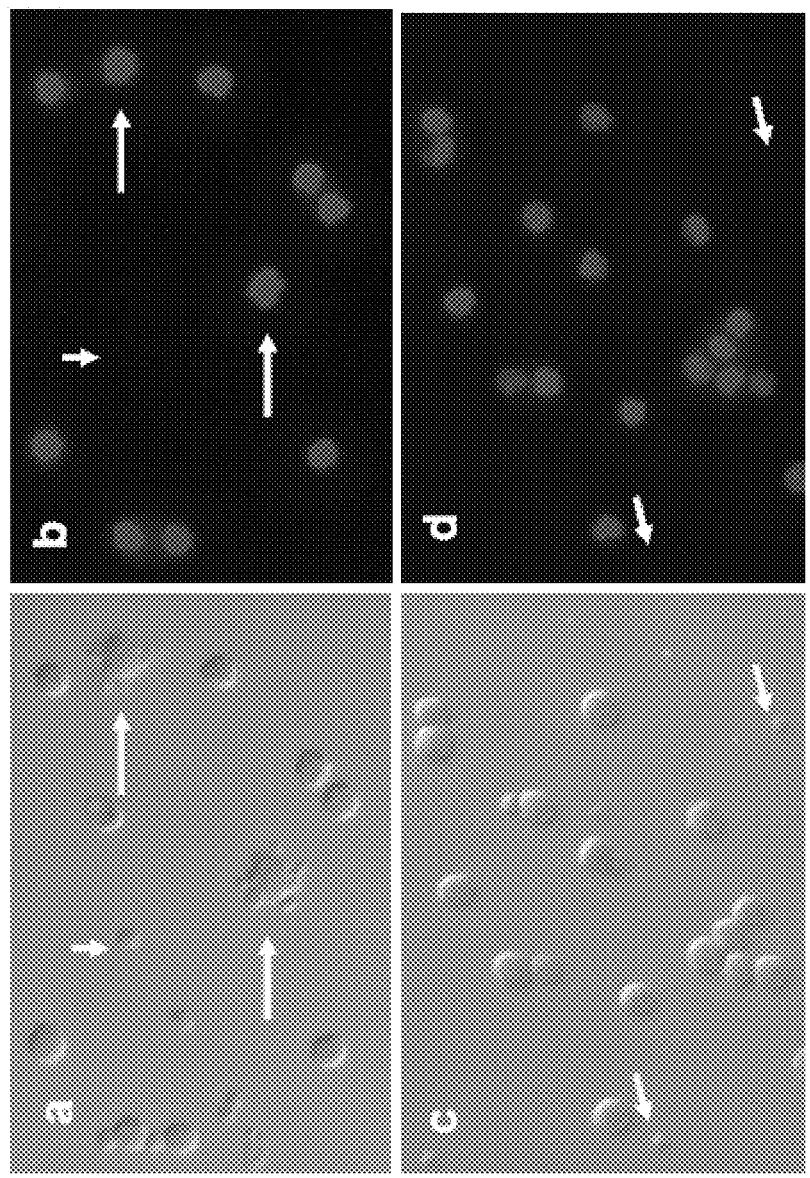
FIG. 3 shows fluorescent photomicrographs which evidence the attachment of human peripheral stem cells by bifunctional antibody target-ELIP coated with antibodies to CD34 and ICAM (a and b) or by a control ELIP coated with normal IgG (c and d). (a) and (c) are bright field images; (b) and (d), are DAPI nuclear fluorescence stained (bright cells). Longer arrows point out ELIP-attached to stem cells. Shorter arrows point to unbound ELIP.

Fluorescent microscopy was performed to analyze morphology and nuclear integrity. The presence of ELIP-attached CD34 cells with normal nuclei was clearly evident in the cells incubated with antibody targeted ELIP coated with anti-CD34 and ICAM antibodies. However, incubation with control non-specific IgG coupled ELIP did not couple the ELIP to the cells (shown in FIG. 3).

Figure 4:
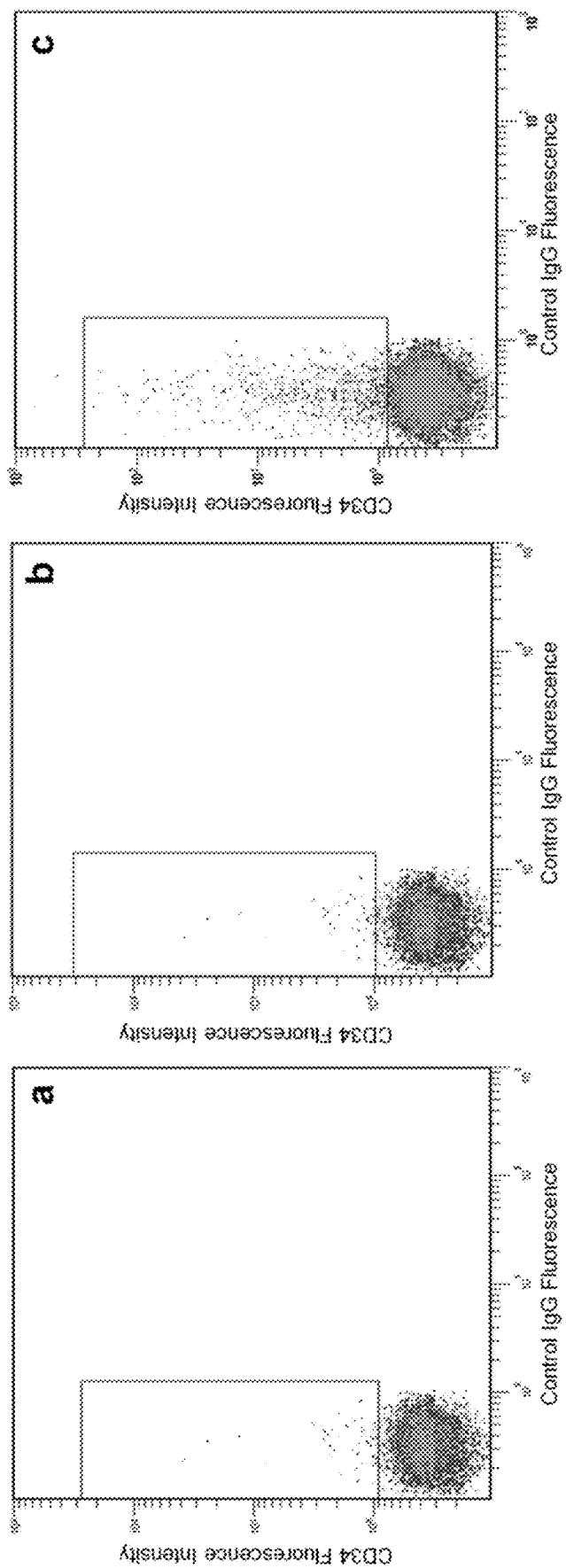
FIG. 4 shows scattergrams of flow cytometric analysis of human mononuclear cells incubated with the ELIP with or without antibody coating. (a) human mononuclear cells incubated with ELIP coupled with IgG-ELIP and visualized using PE-conjugated anti-mouse IgG; (b) human mononuclear cells incubated with ELIP coupled with anti-CD34/ICAM visualized using PE-conjugated anti-mouse IgG; (c) human mononuclear cells isolated from a donor's peripheral blood were incubated with ELIP coupled with anti-CD34/ICAM and visualized using PE-conjugated anti-mouse IgG, this scattergram indicates that 3-3.5% of the circulating mononuclear cells bear CD34.

Additional analysis, using flow cytometry, revealed that about 3-3.5% of mononuclear cells were positive in the human peripheral blood mononuclear cells (shown in FIG. 4). The antibody targeted-ELIP label appeared to be highly specific as there was almost no signal in the cells incubated with control ELIP or ELIP coated with non-immune IgG.

1.4 Ultrasound Enhancement of Transmigration by Stem Cells Coupled with Antibody Targeted-ELIP.

Figure 5:
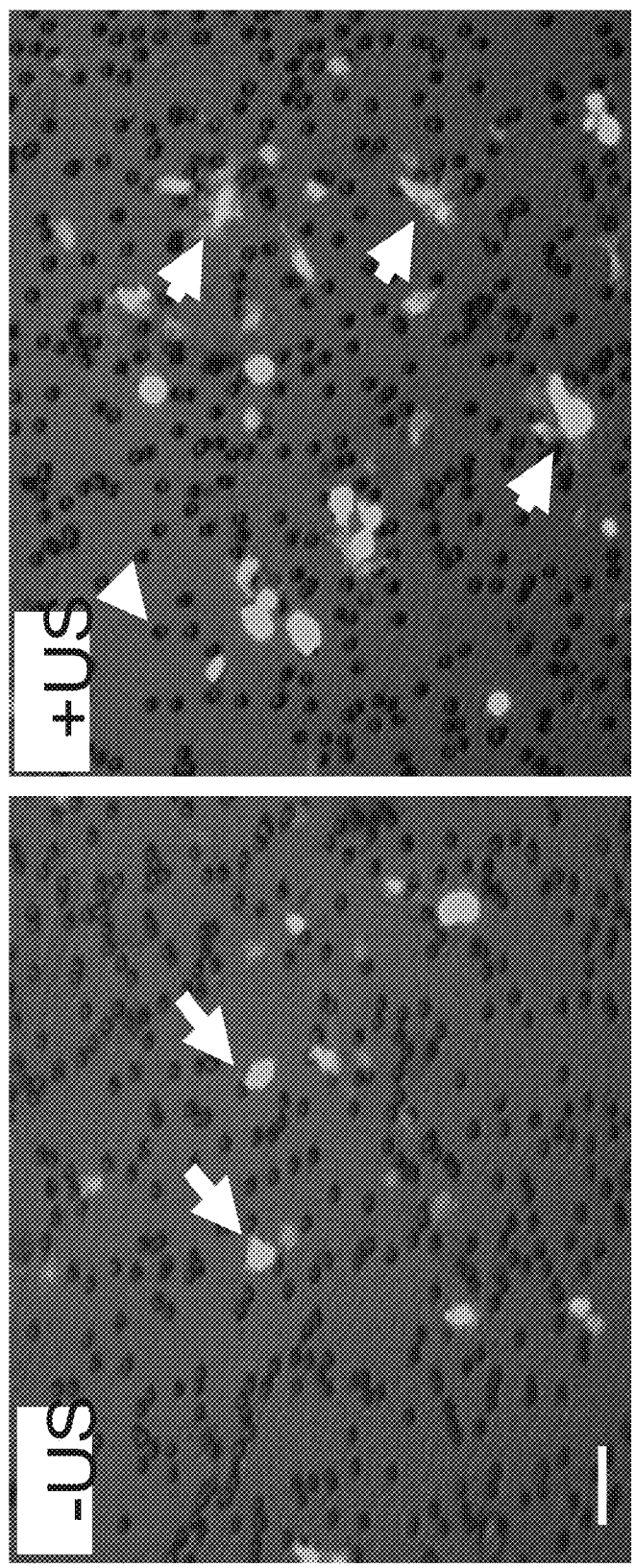
FIG. 5 shows the effect of ultrasound on the transmigration of bifunctional antibody targeted-ELIP-coupled human CD34+ cells through a human endothelial cell monolayer. The arrows point out migrating GFP expressing CD34+ cells which appear bright and the arrow head points to a pore of the insert membrane.

Having demonstrated that circulating VSC positive for expression of CD34 could adhere to activated endothelial cells that produce certain adhesion proteins such as ICAM-1 using the antibody targeted-ELIP loaded with both anti-ICAM and CD34 antibodies. We wanted to demonstrate that ultrasound could enhance the migration of bound stem cells when coupled to antibody targeted-ELIP. To do this an in vitro system in which antibody targeted-ELIP-labeled stem cells were exposed to endothelial cell monolayer pretreated with proinflammatory cytokines such as TNF-alpha and IL-1, two cytokines that are known to induce expression of the adhesion proteins. DAPI-labeled cells at $10^5$ cells/ml were added together with BF-ELIP to the activated EC, cultured for 30 min to allow attachment of stem cells to EC, and then ultrasonicated at 1 MHz (0.5 W/cm$^2$) continuous wave for 30 sec using a 1-MHz transducer (Sonic Concepts Inc., Bothell, Wash., USA). The ultrasound treatment (i.e., "ultrasound releasing stimulus") does not usually cause any damage to the cells, but it ruptures BF-ELIP and greatly enhances the stem cell interaction with EC. After incubation and washing in PBS three times, the cell attachments were clearly visible by inverted microscopy (shown in FIG. 5).

A prototype 1-MHz transducer (Sonic Concepts Inc., Bothell, Wash., USA) using a 1 cm-diameter single circular element made of 1-3 piezo composite material is under development. The −3 dB beam width will be 0.5 cm and the natural focus will be 1.6 cm. The transducer will be optimized for maximum electroacoustic power conversion efficiency. The transducer output will be calibrated in water with a PVDF hydrophone mounted on a computer-controlled three-axis positioner (Velmex, NF-90 series, Bloomfield, N.Y.) and the beam pattern will be carefully mapped.

For some ex vivo porcine carotid experiments using MF-ELIP as described herein, the transducer will be driven in pulsed mode with a duty cycle between 10% and 100% (CW) and the thresholds of stable cavitation and inertial cavitation will be determined. Stable cavitation will be correlated with the intensity and duration of applied ultrasound during 1-MHz ultrasonic irradiation of porcine carotid artery ex vivo in order to optimize ultrasound-mediated therapeutic delivery. Next, the duration of the stable cavitation nucleated by a single antibody targeted-ELIP bolus can be determined, such that an optimal timing scheme for serial bolus injections of antibody targeted-ELIP can be determined for maximizing the duration of stable cavitation, and thus potential drug or stem cell delivery enhancement, over a 1 to 30-minute treatment period. These optimal ultrasound parameters and the optimal antibody targeted-ELIP bolus injection timing scheme will be used for ex vivo and in vivo experiments proposed herein in other examples. Clinically, pulsed Doppler ultrasound will be applied to assure stable cavitation, while maintaining ELIP integrity or fragmenting the liposomes. A safe range of peak-to-peak rarefaction pressures will be determined (or have already been determined) for the various transducer frequencies to be employed.

Figure 22:
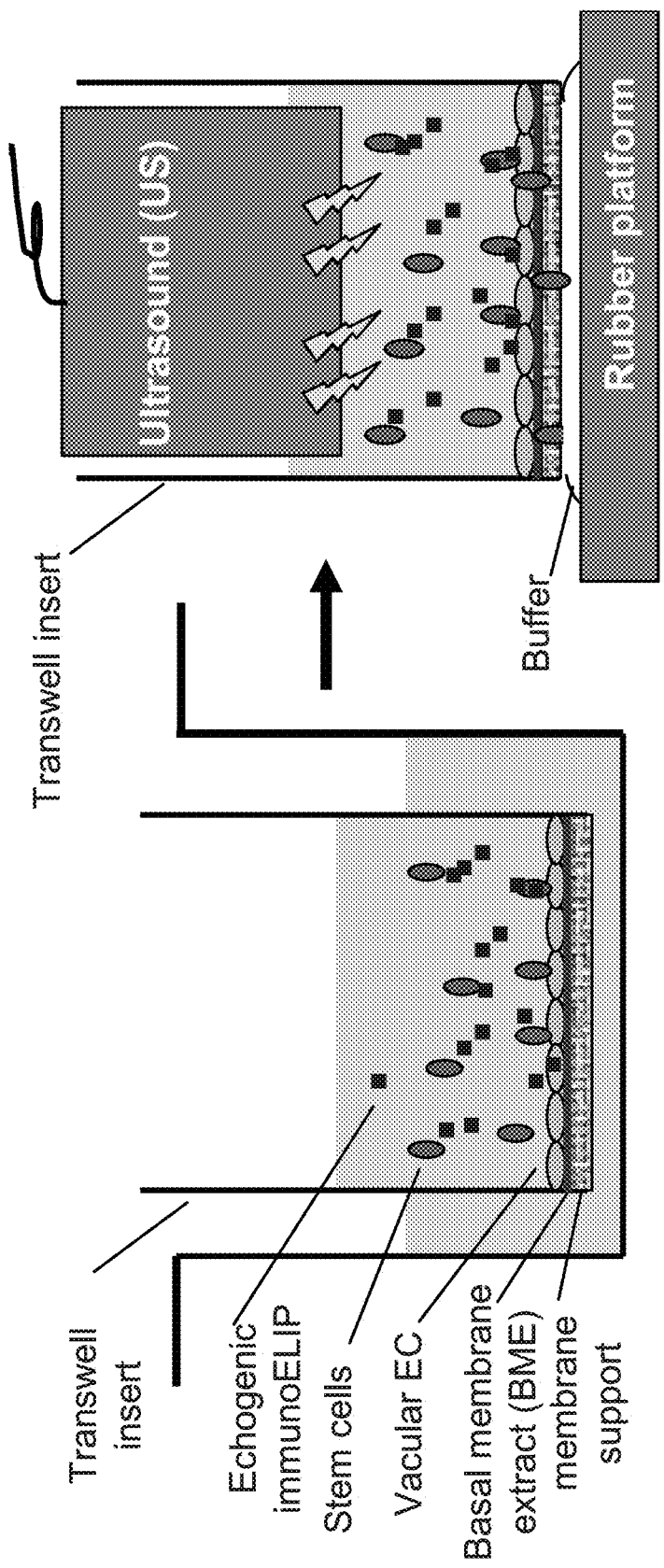
FIG. 22 is a graphic that illustrates the Transwell system that was used to demonstrate the effect of ultrasound on the adhesion and migration of bifunctional antibody targeted ELIP coupled human stem cells.
Figure 23:
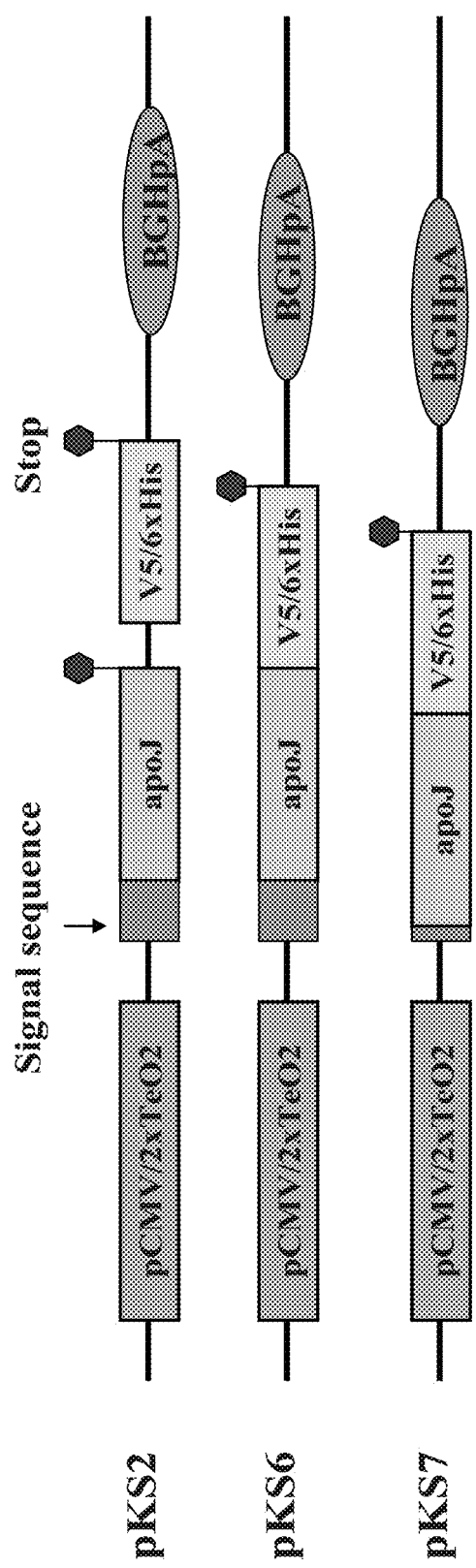
FIG. 23 contains plasmid construct maps of full-length and truncated apoJ. The plasmid pKS2 contains an intact apoJ gene controlled by a CMV (or cell type-specific promoter, e.g., SM22 and Scr for SMC and macrophages, respectively) promoter, which includes two copies of TCN operator responding to tetracycline. In pKS6, the apoJ (clusterin) gene was fused to the VS/6xHis sequence in frame by deleting its stop codon and the intervening 3'-UTR sequence. In pKS7, a sequence with 20 amino acid residues for cross-membrane signaling was deleted to make a dominant-negative form in the cytoplasm.

The impact of ultrasound on antibody targeted-ELIP coupled stem cell penetration and migration was also demonstrated by plating vascular EC onto a 24-well Transwell plate (Corning, Mass.) and incubating them for 24 h to 80-90% confluency. A graphic illustrating this setup is shown in FIG. 22. Bone marrow or fat tissue-derived stem cells (such as described at least in U.S. patent application Ser. No. 11/571,985, published as 20070280456) that had been transduced with GFP or labeled with the fluorochrome DAPI were added into the transwell insert (30,000 cells/ well) and were mixed with antibody targeted-ELIP loaded with antibodies to CD34 and ICAM or VCAM. The transwell insert with the underside of the filter were placed on top of a buffer drop above the rubber support. Following ultrasound treatment, the cell cultures were incubated at 37° C. overnight. After which time the upper and lower wells were washed in PBS, and the cells on the insert filter and bottom membrane were removed and counted under a fluorescent microscope (Olympus). It was determined that there was a 3 fold increase in the numbers of cells migrating through the endothelial cell monolayer when the cultures were treated with an ultrasound releasing stimulus as opposed to those cells that were not subjected to ultrasound (see FIG. 5).

1.5 Generation of Multifunctional Antibody Targeted Echogenic Immunoliposomes.

Multifunctional antibody targeted-ELIP that contain antibodies to both CD34 and ICAM-1, are also conjugated to a third antibody, anti-CXCR4. CXCR4 is the cell-surface receptor for SDF-1, a chemokine that may cause diversion of the stem cells away from atheroma and to endothelial sites that promote atheroma progression. Initial evaluation involves the use of flow cytometric analysis to determine if these multifunctional antibody targeted-ELIP successfully blockade the receptor on human coronary adipocyte stem cells and on human peripheral mononuclear cells.

Enhanced Penetration of Endothelium with Antibody Targeted-ELIP In Vitro and Ex Vivo.

MSC are isolated and cultured from bone marrow and adipose tissue. After labeling with antibody bearing-ELIP, MSC are tested for their capacity of adhesion and penetration through the endothelial cell monolayer under ultrasound enhancement. In vitro and ex vivo experiments are done using cell migration assay kits and the aortic segment cultures as described herein in other examples. Experiments are performed for comparison in the capacity of vascular tissue regeneration between undifferentiated MSC and partially differentiated VSC. Additionally the ability of ultrasound-ELIP treatment to increase the efficacy of stem cell adherent to EC, penetrating through the endothelium to enter the intimal tissue is determined. Porcine stem cells from bone marrow and adipose tissue are isolated, combined with antibody targeted-ELIP and then their capacity of adhesion and penetration through the endothelial cell monolayer under ultrasound enhancement is determined. In vitro and ex vivo tests are performed using a cell migration assay and the aortic segment cultures.

1.7 Preparation and Evaluation of Antibody Bound-ELIP for Targeted Stem Cell Delivery.

The preparation of ELIP is described previously, for conjugation, anionic ELIP are prepared as described above, substituting 1, 2-dipalmitoyl-sn-glycero-3-phosphoethanolamine-N-[4-(p-maleimidophenyl) butyrate] (MPB)-PE for PE. ELIP are lyophilized in the presence of 0.1M D-mannitol. Monoclonal anti-human/mouse ICAM-1 (0.2 mg)+0.2 mg rabbit anti-human/mouse CD34 (both from Santa Cruz Biotechnology, Inc.)+1.6 mg nonspecific mouse IgG are reacted with SPDP at a SPDP-protein molar ratio of 15:1 for 30 min at room temperature (RT). Protein is separated from unreacted SPDP by gel chromatography on a 50 ml Sephadex G-50 column equilibrated with 0.05M citrate-phosphate buffer, pH 5.5. Protein fractions are identified (optical absorbance at 280 nm, $A_{280}$), pooled and concentrated to ≤2 ml using Centricon YM-10 centrifugal filter units. The PDP-protein is reduced in 25 mM dithiothreitol C DTT) for 30 min at RT. The thiolated protein is isolated (G-50 column), equilibrated and eluted with pH 6.7 citrate-phosphate buffer. Protein-containing fractions are pooled and concentrated. The thiolated protein is reacted with reconstituted MPB-ELIP (10 mg lipid/ml 0.1M phosphate buffer, pH 6.62) under Argon overnight at RT. Anionic ELIP are separated from free protein and low molecular weight products by gel filtration on a 20-ml Sepharose CL-4B column that has been pre-saturated with unconjugated ELIP according to the method of Lasch et al. (Lasch J, Weissig V, Brandl M. Preparation of liposomes. 2003. In Torchilin, V. P., Weissig, V. eds. Liposomes, 2nd Ed. New York: Oxford University Press, pp 24-25) and eluted with 0.02M phosphate-buffered saline (PBS), pH 7.4. Liposome-containing fractions are identified by optical absorbance at 440 nm prior to elution of free IgG, established during calibration of the column. The pooled liposome fraction is lyophilized with 0.1M D-mannitol. Conjugation efficiency (CE; in pg antibody/mg lipid) of antibody-ELIP is determined by quantitative immunoblot assay (Klegerman M E, Hamilton A J, Huang S L, Tiukinhoy S D, Khan A A, MacDonald R C, McPherson D D. 2002. Quantitative immunoblot assay for assessment of liposomal antibody conjugation efficiency. Anal Biochem 300:46-52). relative to a composite curve of IgG-ELIP secondary standards. Antibody-ELIP size distribution and number are determined with a Coulter Multisizer 3 (Beckman Coulter, Fullerton, Calif.), fitted with a 20 μm aperture tube, which permits sizing down to 400 nm equivalent spherical diameter. Based on liposome number, CE is also expressed as number of antibody molecules per liposome. Relative echogenicity (apparent brightness) of the liposome formulations is objectively assessed using computer-assisted videodensitometry. All image processing and analyses are performed with Image Pro Plus Software (v. 1.0, Media Cybernetics, Silver Spring, Md.). Data are reported as mean gray scale values.

1.8 Determination of Antibody-ELIP (AB-ELIP) Targeting Efficiency.

A sandwich ELISA protocol is used to determine antibody-ELIP targeting efficiency for ELIP conjugated to monoclonal antibody that binds, by way of example but not limitation, ICAM-1, Tissue Factor, fibrin, VEGF, $\alpha_v\beta_3$, CXCR4, SDF-1, CD34 and CD146. While this specific example will refer to ICAM-1, those of skill in the art will readily see how such an assay could be developed for each determinant. Nunc MaxiSorp microtiter plates are coated with 5 μg/ml of a polyclonal anti-human ICAM-1 capture antibody (R&D Systems, Minneapolis, Minn.) in 0.05M sodium bicarbonate, pH 9.6, overnight at 4° C. All incubation volumes are 50 μl/well. One-third of wells are left uncoated for determination of nonspecific binding. After aspirating well contents, all wells are blocked with conjugate buffer (1% bovine serum albumin in 0.05M Tris buffer, pH 8.0, with 0.02% sodium azide) for 1 hour. From this point, all incubations are at 37° C. Each incubation is followed by aspiration of well contents and washes (3×) with PBS-T (0.02M phosphate-buffered saline, pH 7.4, with 0.05% Tween 20). All wells are then incubated with 200 ng/ml of recombinant soluble human ICAM-1 in 0.1% BSA/PBS-T diluent for 2 hours. For assay of intact antibody-ELIP, wells are washed with PBS after this incubation and the first wash after the antibody-ELIP incubation is also with PBS. Various dilutions of antibody-ELIP in PBS are incubated for 1 hour, followed by a 1-hour incubation with 1:1,000 goat anti-mouse IgG-alkaline phosphatase (Bio-Rad Laboratories, Hercules, Calif.) in conjugate buffer. The substrate incubation consists of 50 μl of substrate buffer (0.05M glycine buffer, pH 10.5, with 1.5 mM magnesium chloride)+50 μl p-nitrophenyl phosphate (Sigma Chem. Co.; 4 mg/ml) in substrate buffer per well for 15 minutes. The reaction is stopped with 50 μl 1M sodium hydroxide per well. The optical absorbance of each well at 405 nm ($A_{405}$) is measured with a Tecan Safire (Tecan Trading, Mänedorf, Switzerland) microplate reader. Net $A_{405}$ is determined by subtracting the absorbance of background wells from that of capture antibody coated wells. The dissociation constant ($K_D$) of MAb or MAb-ELIP binding to rshICAM-1 is derived as b of $y=ax/(b+x)$ from a hyperbolic fit of the ELISA data (y=Net $A_{405}$, x=[Ab]) performed with SigmaPlot software. Antibody concentration, [Ab], for Ab-ELIP is calculated from the CE. $K_D$ values are corrected for perturbation of equilibrium conditions during the anti-mouse IgG-AP incubation according to Underwood (Underwood, P. A. Problems and pitfalls with measurement of antibody affinity using solid phase binding in the ELISA. *J Immunol Methods* 164:119-130 (1993)) and Klegerman (Klegerman M E, Huang S, Parikh D, Martinez J, Demos S M, Onyuksel H A, McPherson D D. Lipid contribution to the affinity of antigen association with specific antibodies conjugated to liposomes. *Biochim Biophys Aca* 1768:1703-1716 (2007)). The targeting efficiency (TE) will also be determined as functional avidity, which is the product of CE, expressed as number of specific antibody molecules per liposome, and the association constant ($K_{assoc}$). An avidity $\geq 1\times 10^{12}$ M$^{-1}$ liposome$^{-1}$ is considered optimal. Another measure of TE is the dissociation constant ($K_D$) expressed as μg lipid/ml, where values<100 μg/ml are considered optimal.

1.9 Adult Stem Cell Isolation and Culture.

Mesenchymal stem cells (MSC): Two stem cell populations with distinct progenies are used, undifferentiated MSC and partially differentiated VSC housed within adult bone marrow (BM), where hematopoietic stem cells and MSC are enriched. MSC have been referred to in the literature by other names such as colony-forming fibroblastic cells, BM stromal stem cells, mesenchymal progenitor cells and BM stromal cells. MSC are considered to be a potential source for cell and gene therapy strategies. Effectiveness of MSC in tissue repair and regeneration has been widely documented, including the repair of cardiovascular tissue injury.

BM will be harvested from murine or porcine bones using a needle attached to a 10-25 ml syringe containing complete media into the spongy bone exposed by removal of the growth plate. After flushing the marrow plug out of the cut end of the bone with 1 ml of complete media BM cells are collected in a 10 or 50 ml tube on ice. In addition to BM, adipose tissue also contains abundant MSC. The BM or adipose tissue-derived cells are cultured in 95-mm culture dishes in 1 ml of DMEM medium (10% fetal bovine serum) at a density of 25×10$^6$ cells/ml at 37° C. with 5% CO2 in a humidified chamber without disturbing them. After 3 h, nonadherent cells that accumulate on the surface of the dish are removed by changing the medium and replacing with fresh complete medium. After an additional 8 h of culture, cell culture medium is changed with fresh complete medium. Thereafter, media replacement is repeated every 8 h for up to 72 h of initial culture. After washing the adherent cells (passage 0) with phosphate-buffered saline, and adding fresh medium every 3-4 d, the initial adherent spindle-shaped cells appear as individual cells on the third day in phase-contrast microscopy. The culture reaches 65-70% confluence within 2 weeks. At this stage, the cultures typically exhibit two characteristics: 1) plates may contain distinct colonies of fibroblastic cells that vary in size; 2) very small numbers of hematopoietic cells interspersed between or on the colonies. After 2 weeks from initiating the cultures, cells can be harvested by trypsinization by incubation in 0.5 ml of 0.25% trypsin/1 mM ethylenediaminetetraacetic acid for 2 min at room temperature followed by washes with PBS. The residual trypsin is neutralized by adding 1.5 ml of complete medium, and all recovered cells are then cultured in a 25-cm$^2$ flask. The media is exchanged with new culture medium every 3 days (replacing with 6 ml of medium each time). Typically, cell confluence is achieved in 7 days.

1.10 Isolation and Culture of VSMC Precursors.

Because MSC are considered multipotent, they can promote hematopoietic recovery and bone regeneration, in addition to vascular MSC differentiation, it is necessary to obtain partially differentiated VSC for some therapies or other uses. Adipose tissue contains EPC as well as the SMC precursor pericytes in addition to MSC. Therefore, partially differentiated VSC are prepared from adipose tissue, because there is more adipose tissue available in the porcine model, the stem cell isolation from porcine subcutaneous or abdominal adipose tissue is used. The adipose tissue is cut into small pieces and digested by 0.1% collagenase A I (Sigma-Aldrich) for 45 min in 37° C., and centrifuged at the speed of 1550 rpm for 10 min, then washed with 10% FBS in DMEM, and Dulbecco's phosphate buffered saline (PBS, Invitrogen, Grand Island, N.Y.) respectively. The cells are resuspended in red cell lysis buffer. After washing three times, cells are cultured in complete culture medium at the density of 2×105 cells/cm2, in a humidified, 37° C., 5% CO2 incubator. The medium is changed twice weekly. Cells are then be subcultured at 5000 cell/cm2 for at least 15 passages. Phenotype analysis of the cells is performed at each passage. For experiments utilizing CD146-targeted antibody bearing-ELIP, HMNC or SMC precursor populations are incubated for 1 hour at ambient temperature with streptavidin magnobeads (Pierce) pretreated with antibodies specific for CD34, CD45 and CD56 (Thermo Scientific; 100 μg ea./1.0 ml bead suspension). The supernatant suspension remaining after magnetic separation is then used as the source of the stem cell population. CD34-CD45-CD56- status and antibody targeted-ELIP binding are verified by using labeled antibodies and flow cytometry.

1.11 Isolation and Culture of Vascular Endothelial Cell Progenitors.

The method for isolation of vascular EPCs follow previous work by Kalka et al. 2000 (Kalka C, Masuda H, Takahashi T, Kalka-Moll W M, Silver M, Kearney M, Li T, Isner J M, Asahara T., Transplantation of ex vivo expanded endothelial progenitor cells for therapeutic neovascularization. *Proc Natl Acad Sci USA*, 97:3422-3427). The three EPC sources include BM, adipose tissue and peripheral blood. Non-adherent cell populations from the cultures of MSC from BM or adipose tissue or mononuclear cells isolated from peripheral blood by Ficoll gradient centrifugation are collected and cultured in medium containing VEGF. In brief, the cells are grown on fibronectin-coated (Sigma) culture dishes and maintained in EC basal medium-2 (EBM-2) (Clonetics) supplemented with 5% fetal bovine serum, human VEGF-A, human fibroblast growth factor-2, human epidermal growth factor, insulin-like growth factor-1, and ascorbic acid. After 4 days in culture, nonadherent cells are removed by washing, new media changed, and the culture maintained through day 7.

1.12 Purification and Biological Characterization of MSC and VSC.

Bone marrow or fat tissue-derived stem cells are characterized by fluorescence activated cell sorting (FACS) for specific surface antigens. Freshly isolated or cultured cells are stained for 30 minutes with fluorescein isothiocyanate- (FITC)- or phycoerythrin (PE)-conjugated antibodies to stem cell markers. The stem cell biomarkers to be tested include CD29 (Abcam Inc. Cambridge, Mass.), CD34, CD44 (BioLegend, San Diego, Calif.), CD45 (Antigenix America Inc., NY), CD90 (BD Pharmingen, San Diego, Calif.), CD133, CD146, Flk-1, Tie-2, $\alpha$-SM actin, c-kit, sca-1, or CD34 and rabbit anti-Octamer-binding transcription factor-4 (Oct4) (BioVision, CA). Non-specific fluorescence is excluded with normal mouse IgG-FITC and IgG-PE (Sigma-Aldrich). Indirect immunostaining is performed with PE-conjugated goat anti-rabbit IgG (Cedarlane Laboratories, Ltd, Burlington, ON, Canada) as a secondary antibody. Cells are analyzed using a flow cytometer (Becton Dickinson, San Jose, Calif.). An angiogenesis assay is performed using an Angiogenesis Assay Kit (Chemicon International, Temecula, Calif.). Following the manufacturer's instructions, cells are seeded onto a 96-well plate covered with matrix gel at the density from 7500-30000 cells/well in 150 μl endothelial cell culture media (M199/5000 U/ml heparin (Sigma-Aldrich)/endothelial cell culture supplement (Invitrogen, Carlsbad, Calif.)/2% FBS). Cells are put into the incubator for 12-18 h, then fixed using 4% paraformaldehyde, and the formed network is observed under the microscope. In some of assays, MSC and VSC are incubated with antibody targeted-ELIP or control IgG-ELIPs for assessing the binding specificity of antibody targeted-ELIP to a particular type of stem cells with individual antibodies.

1.13 Analysis of Multifunctional Antibody Targeted-ELIP Bridging SC to Activated EC Under Ultrasound Enhancement.

VSC are positive for expression of CD34, CD133 and Sca-1, and activated endothelial cells (EC) produce certain adhesion proteins such as ICAM-1, VCAM-1 and CD31, VEGF-receptors or $\alpha_v\beta_3$ integrin. MF-ELIP serves as a linker that bridges stem cells to the activated endothelium. The success of this system is determined by using an in vitro system in which multifunctional antibody targeted-ELIP-labeled stem cells are exposed to endothelial cell monolayer pretreated with proinflammatory cytokines such as TNFa and IL-1, two cytokines known to induce expression of the adhesion proteins. The DAPI-labeled cells at $10^5$ cells/ml will be added together with multifunctional antibody targeted-ELIP to the activated EC, cultured for 30 min to allow attachment of stem cells to EC, and then exposed to 1 MHz ultrasound (US). After incubation and washing in PBS three times, cell attachment is assessed by inverted microscopy and cell numbers are determined by image analysis and morphometry.

1.14 Analysis of SC Adhesion and Migration Through an Endothelial Monolayer in a Transwell In-Vitro Model with Antibody Targeted-Elip and Ultrasound Treatment.

To demonstrate the impact of multifunctional antibody targeted-ELIP and ultrasound on stem cell penetration and migration, vascular EC are plated onto a 24-well Transwell plate (Corning, Mass.) and incubated 24 h to 80-90% confluency. Bone marrow or fat tissue-derived stem cells transduced with GFP or labeled with the fluorochrome DAPI are added into the Transwell insert (30,000 cells/well) and mixed with antibody targeted-ELIP bearing with antibodies specific for CD34 and ICAM-1 or VCAM-1. The Transwell insert is placed on a buffer drop above the rho-C rubber acoustic absorber (Precision Acoustics Inc.), see FIG. 22, to avoid ultrasound reflections. The ultrasound transducer is inserted into the buffer and the cells are exposed to a fixed pressure amplitude, duty cycle and duration as determined previously. The cell cultures are incubated at 37° C. overnight. At the end of culture, upper and lower wells are washed in PBS, cells on the insert filter are removed and cells on the bottom membrane counted using a fluorescent microscope. Optimal ultra sonication parameters are first determined using HMNC (stem cells) alone. Six permutations involving 0.5, 1.0 and 2.0 W/cm$^2$ power settings and 10% and 500% duty cycle are tested. The setting affording maximal transwell migration of DAPI-stained HMNC is utilized for successive experiments.

1.15 Porcine Arterial Preparation and SC Labeling.

For ex vivo studies, freshly isolated aortas or femoral arteries from pigs are washed in cold PBS and segmented in temperature-controlled, oxygenated PBS, and the perfusate comprises a proteinous medium with a viscosity similar to that of blood. MSC or VSC freshly isolated from BM or adipose tissue or peripheral mononuclear cells are incubated with the fluorescent dye DAPI (1 mg/ml) for 5-10 min and washed in PBS. DAPI-labeled cells are then mixed with antibody targeted-ELIP or appropriate controls. In ex vivo studies, the cell-multifunctional antibody targeted-ELIP mixture is loaded onto the lumenal surface of the arterial wall and treated with ultrasound at low energy levels.

1.16 Histochemistry and EM of SC Attachment and Penetration to the Porcine Arteries with MF-ELIP and Ultrasound Treatment.

The ex vivo measurement of antibody bearing ELIP-targeted delivery of stem cells to atherosclerotic porcine arteries is conducted. Stem cells labeled with antibody targeted-ELIP are used for these ex vivo studies. The labeled cells are loaded onto the lumenal surface of the arterial segments placed in commercially available Costar transwell plates (Corning Co), which are well plates with a semi-permeable membrane (non-reflective) at the bottom. The arterial segments are randomized to receive ultrasound or not (ultrasound delivered using SONITRON 1000 RICHMAR, 1 MHz, 0.5 W/cm$^2$; 100% duty cycle for 30 sec). After incubation for 2-3 hours, the tissue will be divided into two parts: one will be fixed in 3% paraformaldehyde for Oil Red O staining and other part fixed in 3% glutaraldehyde for electron microscopy. The multifunctional antibody targeted-ELIP-labeled stem cells are easily detected using Oil Red O stains as liposomes are rich in lipids. The porcine aortic segments with surface adhesion of MF-ELIP-labeled stem cells will be fixed in 3% paraformaldehyde. After washing in PBS, the tissue is stained in Oil Red O solution (2:1 PBS:Isopropanol). Surface staining is visualized using a dissecting microscope (Olympus). For the EM studies, the tissue is dehydrated in a graded series of ethanol, 70%, 80%, 90%, 100%, in 10 minute intervals. The aortic surface is scanned using the JEOL JSM-6460 LV scanning electron microscope (SEM) in the LV SEM mode. The multifunctional antibody targeted-ELIP-cells attached on the lumenal surface of the arteries are counted and compared to that from control groups.

As was observed with bifunctional-antibody bearing ELIP, an increased number of SC on the surface of arteries that are exposed to hyperlipidemia or have endothelial damage as the result of balloon treatment-. However, the contamination of endogenous stem cells may cause false positive or false negative outcomes in terms of numbers of SC found on the surface of the arteries. To address this issue not only are the ELIP labeled but the SC cells are also labeled.

2.0 Delivery of Antibody Targeted-ELIP Containing Genes Encoding Anti-Apoptosis and/or Anti-Inflammatory Factors.

Some embodiments provide for the selective delivery of antibody targeted-ELIP coupled stem cells along with anti-apoptosis and/or anti-inflammatory factors (genes, proteins, or drugs) that enhance the survival, proliferation, migration, activity and differentiation of the targeted stem cells to inflammatory atheroma. For example, some suitable drugs or bioactive molecules for loading into an ELIP include, but are not limited to, those that enhance the survival or efficacy of stem cell delivery and include, but are not limited to, erythropoietin (EPO: see for example, Madonna R, et al. Erythropoietin protects myocardin-expressing cardiac stem cells against cytotoxicity of tumor necrosis factor-alpha. *Exp Cell Res.* 2009 Oct. 15; 315(17):2921-8), tetracycline or analogs, statins (such as, atorvastatin, cerivastatin, fluvastatin, lovastatin, mevastatin, pitavastatin, pravastatin, rosuvastatin, simvastatin), and as described, at least in U.S. patent application Ser. No. 11/673,888, published as 20070190651, compounds or drugs which prevent apoptosis, including, but not limited to, caspase inhibitors, losartan potassium, ubiquitin and compounds with local anti-inflammatory activity (as described, at least in U.S. patent application Ser. No. 11/573,508, published as 20080311607).

Some examples of antibodies which may be loaded into an ELIP include, but are not limited to, antibodies that target stem cells or the atheroma. Examples of antibodies that may be used to target stem cells include, but are not limited to, those that bind, CD34, CD146, chemokine receptors, CD140, CD144, PDGF receptor, CD133, CD13, CD29, CD44, CD90, sca-1, VEGF receptor 1, c-kit, stem cell growth factors, SDF, TNF alpha and beta, insulin like growth factor-1 (IGF-1: Yu X Y et al. The effects of mesenchymal stem cells on c-kit up-regulation and cell-cycle re-entry of neonatal cardiomyocytes are mediated by activation of insulin-like growth factor 1 receptor. *Mol Cell Biochem.* 2009 December; 332(1-2):25-32) and clusterin.

Examples of genes configured to be carried by an ELIP and released, taken up and expressed in a target tissue include, but are not limited to, c-kit and clusterin (ApoJ).

Antibodies that may be used to target atheroma include, but are not limited to, intercellular adhesion molecule-1 (ICAM-1), vascular cell adhesion molecule-1 (VCAM-1), fibrin, integrins, vascular endothelial growth factors (VEGF, including, but not limited to, species A-D and VEGF-A isoforms 110, 120 or 121, 164 or 165, 188 or 189 and 206), tissue factor, smooth muscle cell myosins and actins, matrix metaloproteinases (MMPs), E-selectin and P-selectin, insulin-like growth factor-1 receptor (IGF-1R), von Willebrand's factor and macrophage markers (for example AM-3K, 7C3, 25F9, 27E10, carboxypeptidase M (CPM), cathepsin K, chitotriosidase, CD14, CD68 (Ki-M7, Y2/131, Y1/82A, EBM11), CD163, CD163 soluble (sCD163), CSF-1R (colony-stimulating factor-1 receptor), ED-1, ED-2, ED-3, EMR1, F4/80, Factor XIII-A, ferritin, HAM-56, Ki-M1P, lysozyme M, MAC-1/MAC-3, Myeloid-related protein (MRP) 14, RFD7/RFD9, RM3/1). Also useful for targeting atheromas are antibodies directed at scavenger receptors (ScR: such as CD36, ScR-I/II), at chemokine receptors (CXCR4, MCP-1 receptors, CD18), and at TNF receptors (for example R1/R2).

2.1. Gene Delivery to Vascular Endothelial Cells with ELIP.

Figure 6:
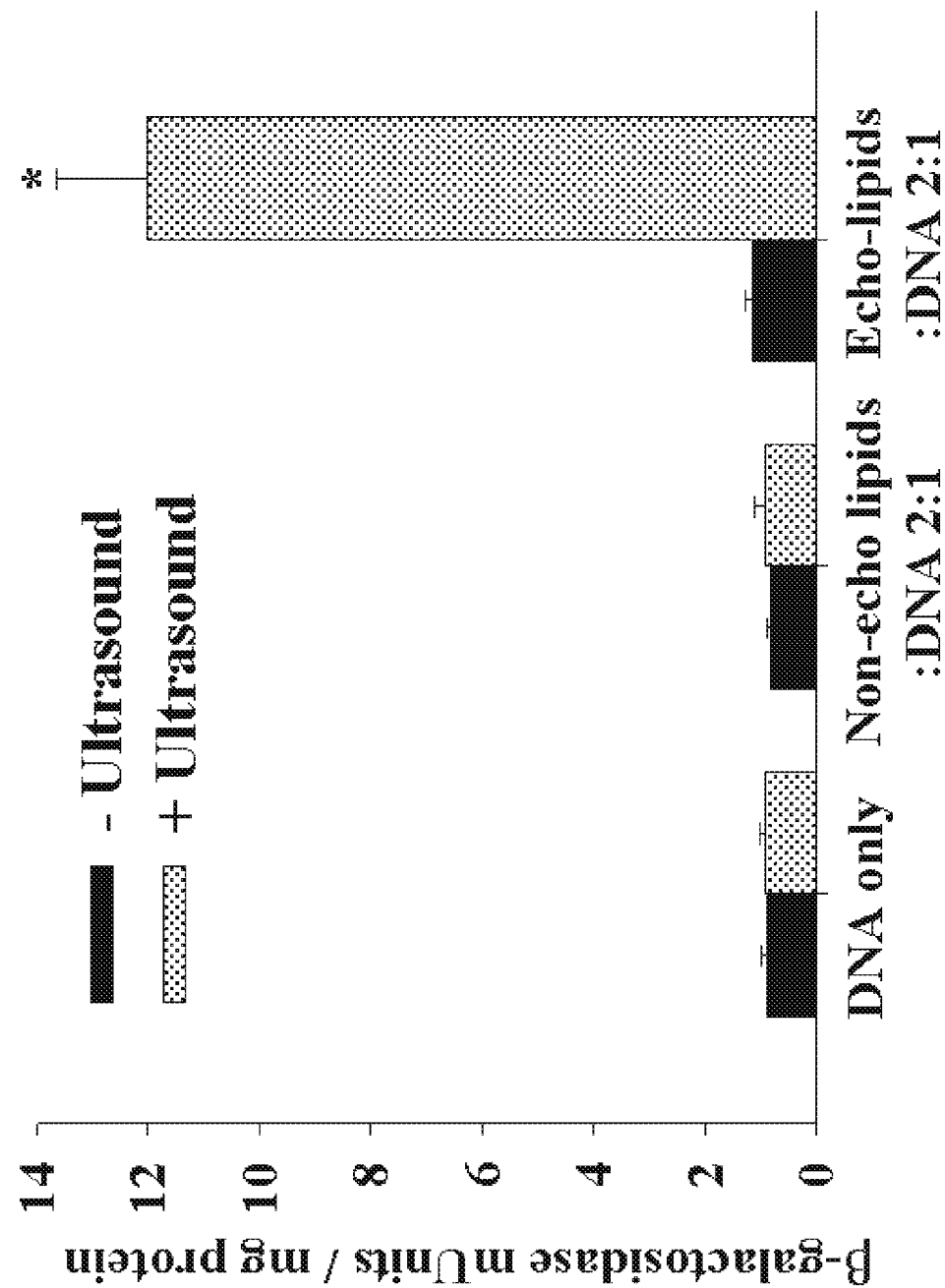
FIG. 6 is a bar graph showing that the addition of ultrasound enhances the transfection efficiency of human endothelial cells with ELIP-LacZ cDNA.

To validate this approach it was first demonstrated that that ELIP can act as a vehicle to deliver a cDNA coding for a reporter gene such as B-galactosidase to the vasculature and that this gene can be effectively be delivered to vascular endothelial cells and released using ultrasound. ELIP that were more cationic were formulated, while maintaining stability and conjugation properties. The reporter gene lacZ encoding ß-galactosidase was then incorporated into ELIP, and transfected the ELIP-lacZ cDNA into human umbilical vein endothelial cells (HUVEC) using the method previously reported by Tiukinhoy et al., 2000 (Tiukinhoy S D, Mahowald M E, Shively V P, Nagaraj A, Kane B J, Klegerman M E, MacDonald R C, McPherson D D, Matsumura J S (2000). Development of echogenic, plasmid-incorporated, tissue-targeted cationic liposomes that can be used for directed gene delivery. *Invest Radiol,* 35:732-738). Treatment with low levels of ultrasound (1 MHz ultrasound at 2 W/cm$^2$ for 10 sec) greatly enhanced the efficiency of the lacZ cDNA-ELIP transfection by up to 30-fold; this effect was significantly attenuated when non-acoustically active agents were used (FIG. 6). Also developed are methods to accurately characterize oligonucleotide encapsulation and release following ultrasound exposure from our ELIP.

2.2 ApoJ cDNA Transfection Enhances Expression of CXCR4 and Stem Cell Migration.

Figure 7:
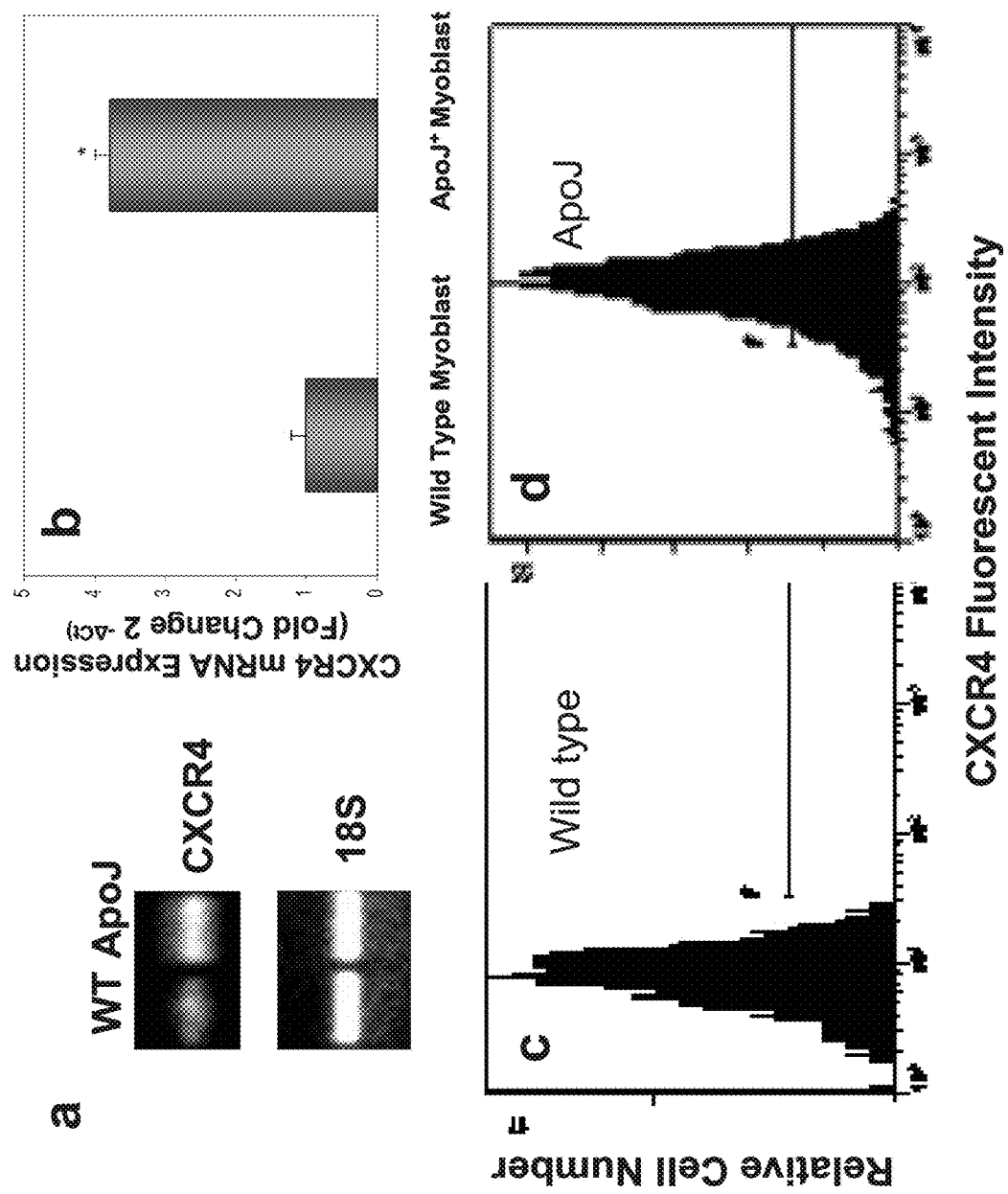
FIG. 7 shows the increased expression of the chemokine receptor CXCR4 in ApoJ-transfected fetal canine myoblasts as determined by: (a) RT-PCR; (b) quantitative real time PCR of CXCR4 mRNA; (c) flow cytometric determination of the relative number of cells expressing CXCR4 in wild-type cells; and (d) in cells transfected to overexpress ApoJ (n=4).

ApoJ is believed to have anti-apoptosis activity, conferring resistance to apoptotic cell death, as well as having anti-inflammatory activity. Therefore we chose to transfect ApoJ into stem cells with the intent of improving their survival, proliferation, migration, activity and differentiation. ApoJ-transfected stromal cells or myoblasts from fetal canine hearts expressed higher levels of CXCR4 mRNA than wild-type control cells as assessed by real time PCR (FIGS. 7a and 7b). Using flow cytometric analysis it was illustrated that there was a significantly increased cell surface expression of CXCR4 in the myoblasts that were overexpressing ApoJ (ApoJ-transfected canine fetal myoblast vs. control myoblasts; 29.8%±3.4% vs. 10.5%±2.1%, respectively; p<0.01) (FIGS. 7c and 7d). Taken in combination, these findings suggest ApoJ expression greatly enhances the migrating capacity of canine fetal myoblasts in a CXCR4 dependent manner.

Figure 8:
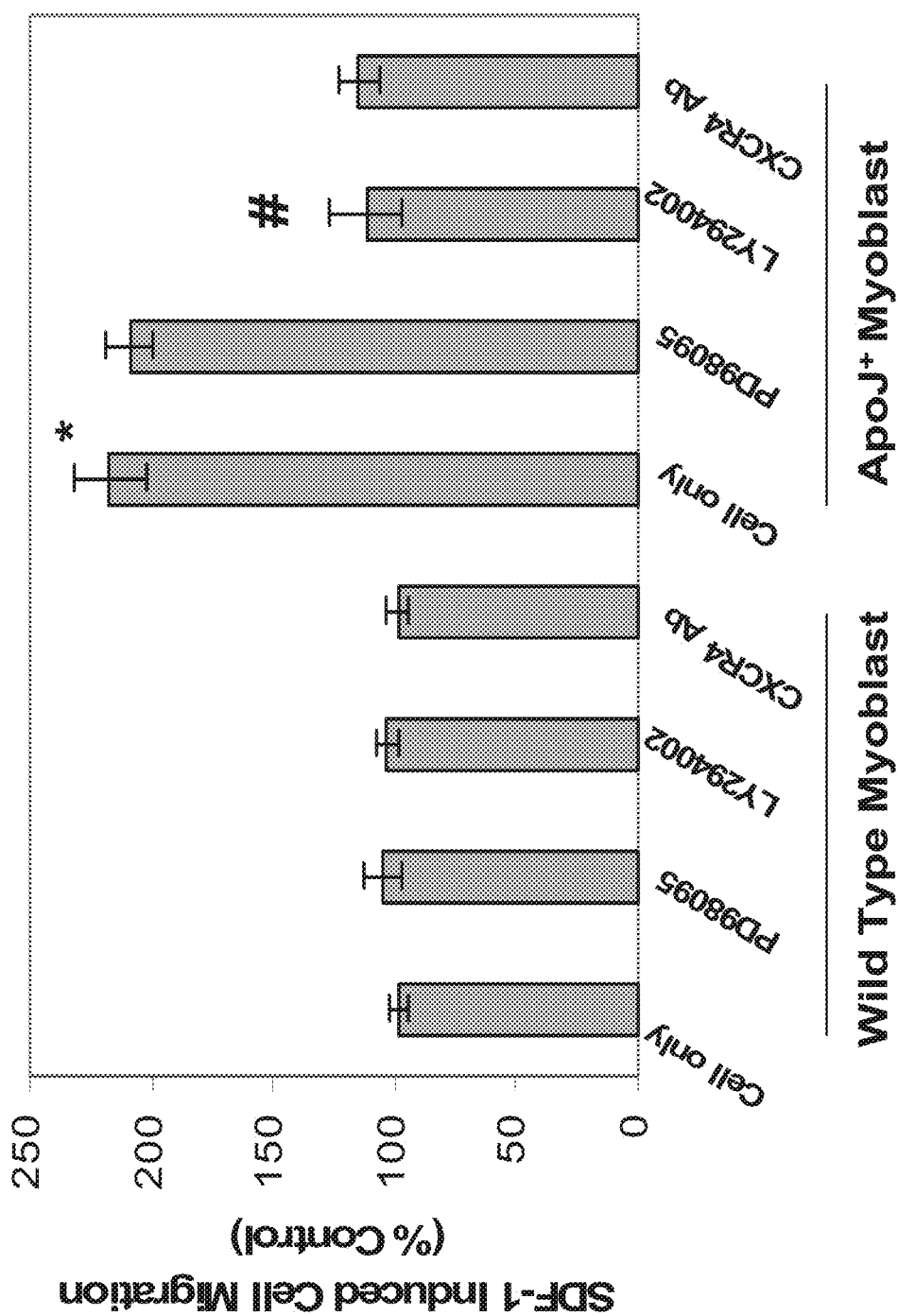
FIG. 8 shows the SDF-1 induced cell migration, in wild-type fetal canine myoblasts and in ApoJ-transfected fetal canine myoblasts. Results are presented as mean±SD with n=6.
Figure 9:
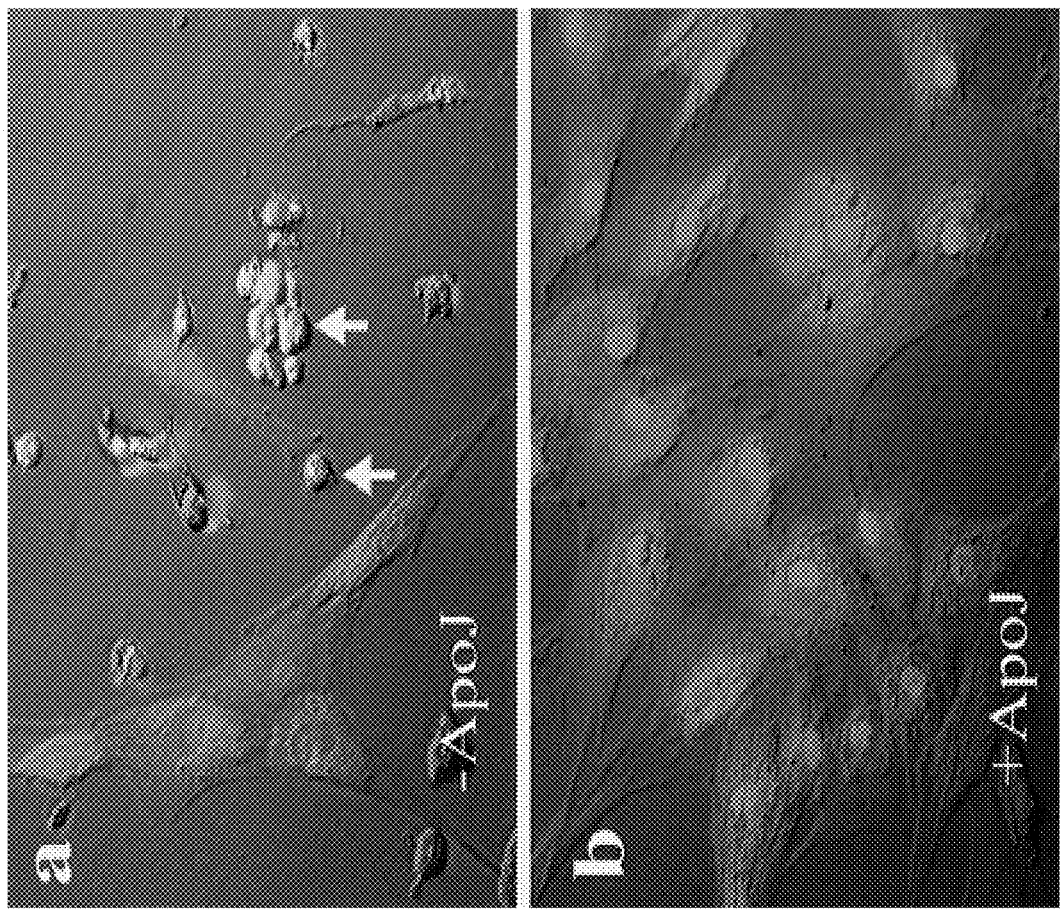
FIG. 9 shows fluorescence micrographs of murine aortic smooth muscle cells obtained from (a) ApoJ-null (ApoJ-) mice and (b) wild-type (ApoJ+) mice after incubation with 7-ketocholesterol. Staining with acridine orange and ethidium bromide revealed more apoptotic cells in the cultures of the ApoJ-null smooth muscle cells. The Arrows point to cells that have undergone apoptosis.

Providing further evidence that expression of ApoJ significantly increases stem cell migration, cell migration assays were performed using a transwell system (BD Biosciences). Cells were placed at a concentration of $5\times10^4$/well in the upper chamber (BD Biosciences), and the chamber was placed in a 24-well culture plate (BD Biosciences) containing culture medium and 100 nM SDF-1 for measuring the migratory capacity of myoblast cells. After 48 hours of incubation at 37° C., the medium was removed, and the insert was transferred to a second plate containing Calcein-AM solution. The plates were incubated for 90 minutes at 37° C. in a 5% $CO_2$ incubator. The fluorescence of migrating cells was read in a fluorescence microplate reader with bottom reading capabilities at excitation/emission wavelengths of 485/530 nm. Over expression of ApoJ significantly increased the number of cells migrating in response to SDF-1 (100 nM). This migration was attenuated by the addition of a PI3 kinase inhibitor (LY294002, 5 µM) suggesting that the ApoJ-induced increase in canine fetal myoblast migration was dependent on activation of PI3 kinase. By contrast, the mitogen-activated protein/ERK kinase inhibitor, PD98059 (30 µM) did not have any significant impact on the cell migration. However, pretreatment with anti-CXCR4 antibody (10 µg/ml) did partially inhibit cell migration (FIG. 8). Apoj expression can also provide protection against apoptotic stem cell death. This finding is consistent with published results that ApoJ expression can provide some protection against apoptotic cell death. Exposure to oxidized cholesterol or oxysterol often triggers apoptosis in a variety of cells and atheroma contains abundant oxysterols such as 7-ketocholsterol. Therefore, a study was done to establish that ApoJ expression will exert protective effects against apoptotic cell death for stem cells. After incubation of vascular smooth muscle cells from the aorta of ApoJ-knockout mice or wild-type mice with 10 µg/ml 7-ketocholsterol for 24-48 the cells were examined for viability by stained with a combination of acridine orange and ethidium bromide. Living cells showed normal morphology and emitted green fluorescence. Dead cells were shrunken and displayed yellow-red fluorescence. Compared to the vascular smooth muscle cells obtained from knockout mice, wild-type vascular smooth muscle cells, that are positive for ApoJ expression, had more surviving cells (FIG. 9). Thus, ApoJ expression did appear to provide protection of vascular smooth muscle cells against apoptotic cell death, such as that which results from oxidized cholesterol in an atheroma.

2.3. Tetracycline (TCN) Activated Apoj Gene Expression Increases Resistance of HEK293 Cells to Apoptosis Induced by TNF-α.

Figure 10:
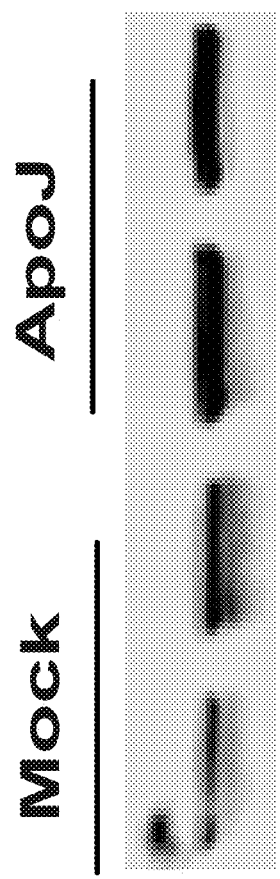
FIG. 10 shows an immunoblot illustrating the expression of ApoJ protein in HEK293 cells that have been mock transfected (as a control), or those that have been stably transfected to overexpress ApoJ cDNA.
Figure 11:
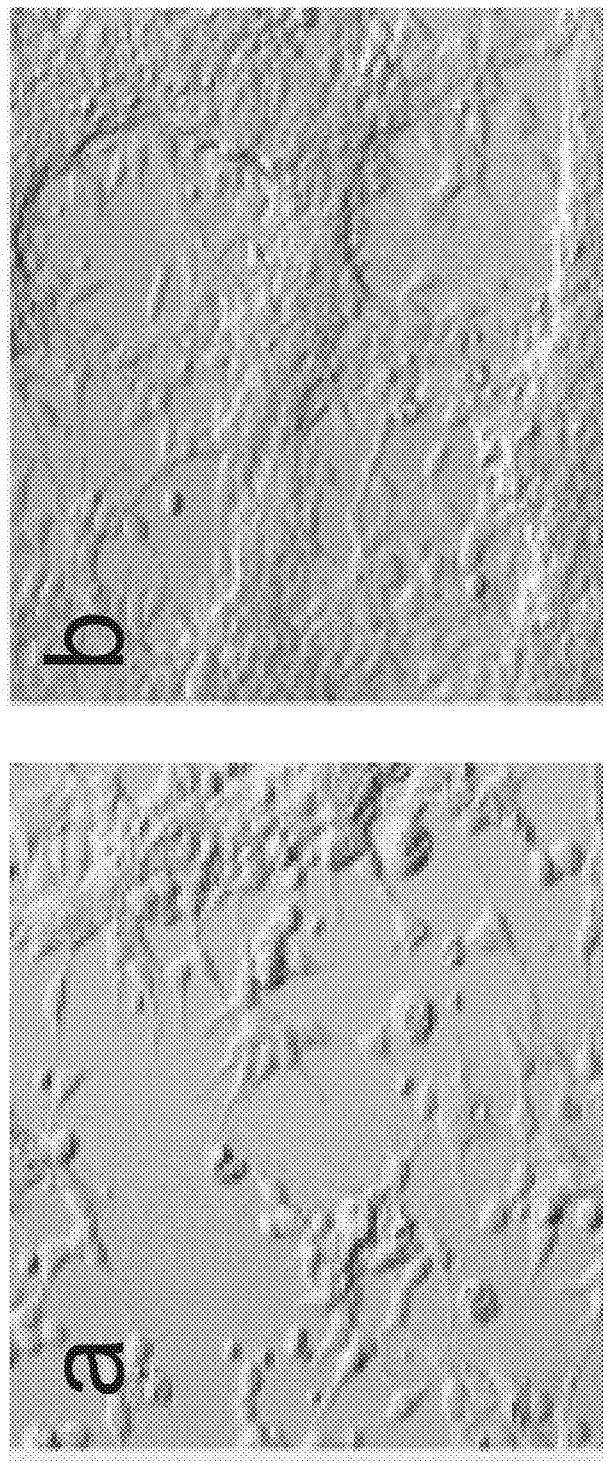
FIG. 11 is photomicrographs of KG-293 cells that have been submitted to TNFα (20 ng/ml) triggering of apoptosis for 48 hrs. (a) cells that have not had ApoJ expression induced by tetracycline and (b) cells that have undergone tetracycline-induced ApoJ expression and were shown to be resistant to TNFα induced apoptosis.

Recent studies have shown that ApoJ can be induced by certain growth factors such as TGF-ß translocate to the nucleus participating in apoptosis regulation. To determine whether intracellular expression of ApoJ inhibits receptor-mediated apoptosis induced by cytokines, we constructed a plasmid (pkS7) with ApoJ cDNA insert lacking the sequence for the domain of protein secretion. The non-secreted, intracellular isoform of ApoJ gene mimics the intracellular isoform inducible by TGF-ß. Under regulation by a CMV promoter with TCN-responding elements, pKS7 transfection of HEK293 cells generated a stable cell line (KG-293) with ApoJ over expression. TCN (1 µg/ml) treatment for 24 hours caused KG-293 cells but not their precursors, T-293 cells, to produce an intracellular form of ApoJ at much higher levels, as identified using Western blot with anti-ApoJ antibody (FIG. 10). Treatment with TNF-α at 10 ng/ml for 24- and 48-hours induced marked apoptosis in the control KG-293 cells that were not exposed to TCN. The pro-apoptotic effect of TNF-α was significantly attenuated in KG-293 cells with intracellular over expression of ApoJ. KG-293 cells over expressing the intracellular form of ApoJ also underwent dramatic alterations in morphology and proliferation. The cells tended to aggregate and showed more proliferating (FIG. 11). Cells with intracellular over expression of ApoJ had a much higher viability than wild-type control cells (viability 83±5% in the transfected vs. 35±6% in the control cells, n=6), suggesting an increased resistance of the ApoJ-transduced cells to apoptosis induced by TNF-α.

2.4 Gene Delivery to Vascular Endothelial Cells with ELIP.

Cationic ELIP were formulated, while maintaining stability and conjugation properties. Various embodiments of antibody targeted-ELIP-TCN delivery systems were developed, and it is proposed that these will be used to activate the ApoJ transgene, while inhibiting osteogenesis and calcification of MSC in ATH-prone ApoE mice.

2.5 ApoJ-ELIP cDNA Encapsulation and Transfection.

In some embodiments, methods have been developed to accurately characterize oligonucleotide or cDNA encapsulation into ELIP and released the gene under ultrasound exposure. Although initially developed for acoustic enhancement and plaque characterization, these ELIP have been modified to allow for gene delivery. ELIP has the capacity to carry drugs or genes within the aqueous core. The ELIP composition was modified to be cationic with retention of echogenicity, stability, and conjugation properties. ApoJ cDNA or a reporter gene (a firefly luciferase or lacZ gene) is loaded into the ELIP, and demonstrated effective transfection in stem cells as well as in endothelial cells. The ELIP-cDNA complex is tested for transfection efficiency after exposure to 1 MHz pulsed ultrasound (SONITRON 2000, Rich-Mar Corp, Inola, Okla.) at a peak-to-peak pressure amplitude of 0.33 MPa for 30 s. This method was previously shown to gain highly efficient cell transfection (an up to 30-fold increase in transfection efficiency.

2.6 Transduction of Full-length or Truncated ApoJ by ELIP-cDNA Transfection.

Figure 12:
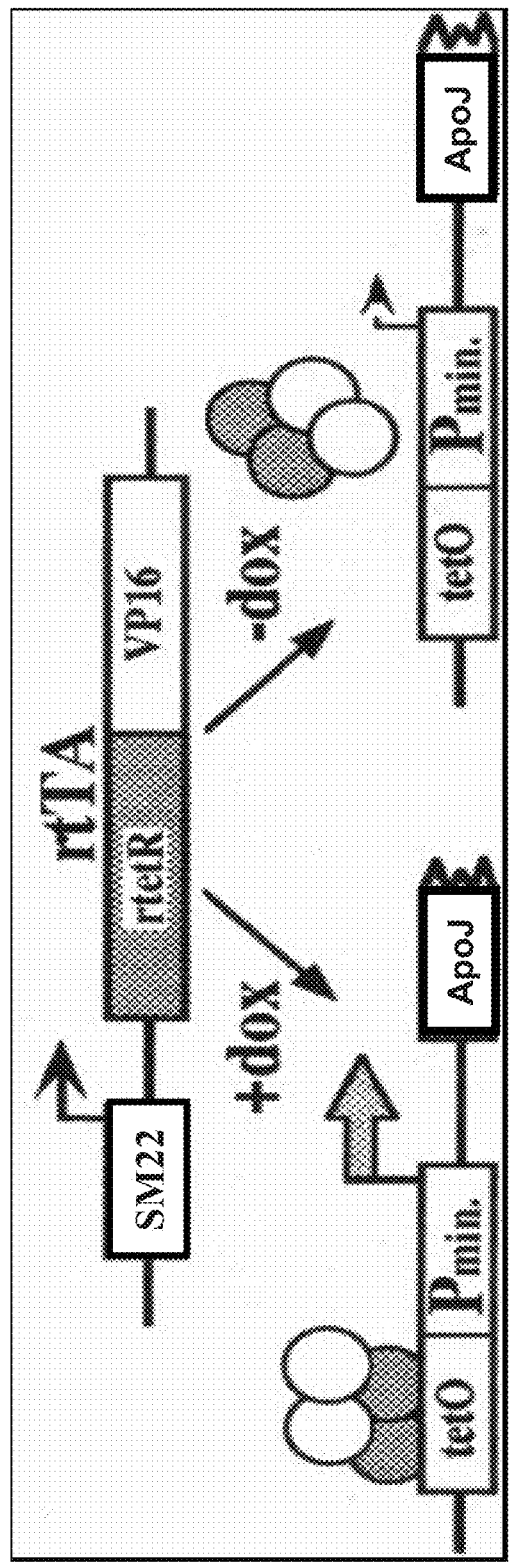
FIG. 12 is a schematic outline of the tetracycline (TCN) regulated transgene for expression of ApoJ transgene in mice. Mechanism of action of the Tc-controlled transactivator (tTA). The fusion protein is composed of the repressor (rtetR) of the TnlO Tc-resistance operon of *Escherichia coli* and a C-terminal portion of protein 16 of herpes simplex virus that functions as a strong transcription activator. rtTA binds in the presence but not absence of TCN or its analog doxycycline (dox) to an array of seven cognate operator sequences (tetO) and activates transcription of apoJ gene from a minimal human cytomegalovirus (hCMV) promoter (Pmin), which otherwise is inactive. Because rtTA expression is driven by SM22, a vascular smooth muscle-specific promoter, or Tie-2 endothelial cell promoter, the dox-regulated apoJ transgenic expression will be specific to the vascular smooth muscle cells or endothelial cells.

ELIP-ApoJ cDNA are prepared by loading ApoJ cDNA plasmid into antibody targeted-ELIP and then the ELIP are incubated with stem cells or vascular cells, and 2-3 days after transfection, cells are examined for ApoJ expression by RT-PCR for mRNA and Western blot for protein. Cultured SMC from murine aortic tissue and monocyte-derived macrophages from peripheral blood are used to illustrate that ELIP-ApoJ cDNA induced ApoJ overexpression reduces apoptosis of vascular cells induced by proinflammatory cytokines. In some studies human embryonic kidney cell line HEK-293 are used as a model system for ApoJ expression because transduction of foreign genes in this cell line is more efficient than in normal cells. The cells are transfected with plasmids containing full-length or truncated ApoJ cDNA inserts. The construction of these plasmids is complete (FIG. 12).

ApoJ cDNA is generated by RT-PCR and full-length or truncated ApoJ cDNA is subcloned into an expression plasmid vector under general (e.g., CMV) or cell-specific promoters (e.g., SM22 for VSMC and Tie-2 for EC). This cell culture system is used to test if ApoJ-transfected cells and non-transfected cells show different or similar apoptotic responses to proinflammatory cytokines, TNFα and IFNγ, FasL or agonistic anti-Fas antibodies.

A plasmid is constructed with a cDNA insert coding for truncated ApoJ which acts as a dominant-negative suppressor to block normal function of ApoJ. Expression of truncated and full-length ApoJ in the cells is controlled by a TCN-sensitive promoter. Cells are stimulated with cytokines and FasL for 2-3 days and are analyzed as to whether ApoJ isoforms are expressed and exert different regulatory effects on apoptosis of endothelial cells and SMC as well as their progenitor VSC. HEK 293 cells will be used as a positive control. In addition, negative control cells are prepared with mock plasmid without ApoJ cDNA. Apoptosis of the treated and untreated cells are determined by assessing morphological alterations, annexin-V binding, DNA fragmentation and caspase activation.

Mitochondrial Membrane Potential and Cytochrome-C (Cyt-c) Release.

Mitochondrial dysfunction is a key step in apoptosis induced by cytotoxic chemicals through non-receptor mediated cell death pathway. The cells are examined for their viability. Several types of membrane-permeable lipophilic cationic fluorochromes, such as DiOC6 and Rh 123, are used as probes for analysis of the potential in flow cytometry. A combination of Rh123 and propidium iodide labels non-apoptotic cells green, early apoptotic cells dim green, and late apoptotic cells red. The membrane potential $\Delta\psi_m$ decrease is usually reflected by reduced intensity of the green fluorescence. The data are analyzed in a computer program for quantitation. Through an adaptor protein, cyt-c released from mitochondria can activate caspase-9 and then a DNase, leading to a final episode of apoptosis. To detect cyt-C release from the mitochondria of vascular cells treated with or without oxLDL and oxysterols, cytosolic proteins are collected for immunoblotting after the oxysterol stimulation. The cellular membrane can be permeabilized with digitonin (10 μg/ml), while the mitochrondrial membrane remains intact as digitonin has no effect on mitochondria. Permeabilized cells are centrifuged and supernatants are collected for immunoblotting with anti-cyt-C antibody (PharMingen).

Analysis of ApoJ-Mediated SC Homing and Trafficking in Multi-Functional Antibody Targeted ELIP Delivery.

Homing and migration are critical steps for stem cells to enter atherosclerotic lesions, differentiate into mature vascular cells, and consequently repair the diseased tissues. However, the mechanisms responsible for stem cell migration are unknown. Our preliminary data showed the regulatory effect of ApoJ, a stress-responding, chaperone-like protein in high-density lipoprotein (HDL), on stem cell migration. Multifunctional-antibody bearing ELIP with ApoJ cDNA will be used for selectively activating expression of ApoJ in the vascular tissue with stem cells transfected with ApoJ cDNA, and subsequently examined whether ApoJ expression will increase expression of CXCR4 (a receptor for stromal cell-derived factor-1, SDF-1) and the migratory response of canine fetal cardiac stem cells or myoblasts to SDF-1.

To determine if ApoJ-induced increase in SDF-1-mediated stem cell migration is controlled by PI3 kinase, the kinase inhibitor LY294002 is added to the cell cultures. For comparison, the mitogen-activated protein/ERK kinase inhibitor PD98059 is used. Immunoblotting with anti-CXCR4 antibody and transwell migration assays (as described herein) is conducted in MSC and VSC with or without ApoJ expression. This protein expression may increase SC migration via CXCR4 chemokine receptor signaling in a PI3/Akt-dependent manner. Stress and growth factor stimulation will induce expression of intracellular ApoJ in stem cells, and that ApoJ-positive cells are resistant to pro-inflammatory, pro-apoptotic cytokines in terms of apoptosis. These findings provide important novel strategies for stem cell therapy by modulating lipoproteins.

Efficacy and Biosafety of Antibody Targeted-ELIP Targeted Delivery of MSC and VSC to Inflammatory Atherosclerotic Lesions.

In vivo studies were performed using antibody targeted-ELIP targeted delivery of MSC and VSC administered by intravenous injection or ventricular injection. A three dimensional culture system was developed to assess outgrowth of stem cells inside the aortic segments with or without atherogenesis. In addition, ELIP loaded with TCN or its derivative was used to inhibit osteogenesis and facilitate differentiation of MSC into VSMC.

Ultrasound Detection of Targeted Stem Cell Delivery with Antibody Targeted-ELIP to Atheroma in Aortas.

Figure 13:
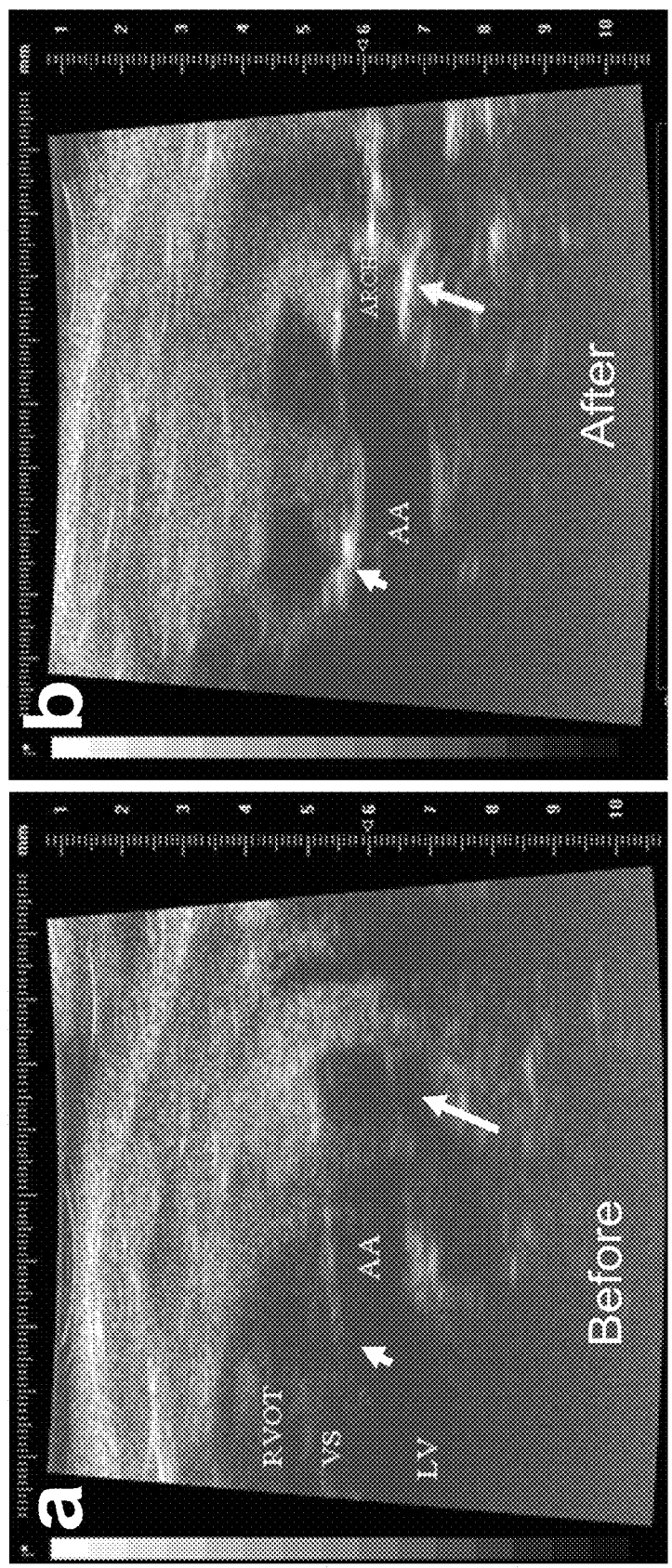
FIG. 13 shows the result of echography of aorta from an ApoE-null mouse before and after ventricular injection of bone marrow stem cells labeled with bifunctional-ELIP coated with antibodies to CD34 and ICAM. 40-MHz B-Mode ultrasound imaging (Visual Sonics VEVO 770) of the aorta in an ApoE null mouse demonstrating highlighting of the aorta with bone marrow stem cells bound to anti-ICAM/CD34 bifunctional ELIP. Arrows points to atheroma lesion sites. Shorter arrows point to the aortic root and longer arrows the aortic arch.

To demonstrate that antibody targeted ELIP can bridge stem cells to atheroma and become detectable by ultrasound, bone marrow-derived mononuclear cells labeled with ELIP coated with antibodies to CD34 and ICAM were injected into the left ventricle of ApoE-null mice (male, 1.5 yrs old). Echography of the heart and aorta was performed before and after injection using the VisualSonics Vevo 770 Echo System with a 40 MHz probe. Mice were anesthetized with isoflurane and the heart rates and body temperature were monitored. Before and after ELIP (acting as an ultrasound contrast agent) injection with or without bone marrow cells, the longitudinal views of the heart and aorta were obtained and digitized images were stored. Control experiments were conducted with ELIP conjugated to non-immune IgG. Before injection of bone marrow cells with BF-ELIP (0.1 ml cell suspension in saline per injection), ultrasound revealed aortic wall thickness, but weak plaque images (FIG. 13a). A more intense signal showed up in both the root of aorta and ascending aorta 3-5 min after injection (FIG. 13b). The region with the enhanced echo signal is known to frequently develop atherosclerotic plaques. Untargeted ELIP alone did not produce the same type of echo signal when injected at the same concentrations. After the ultrasound examination, the aorta was removed and stained with Oil Red O (0.5%) to assess atherosclerotic plaque development.

Figure 14:
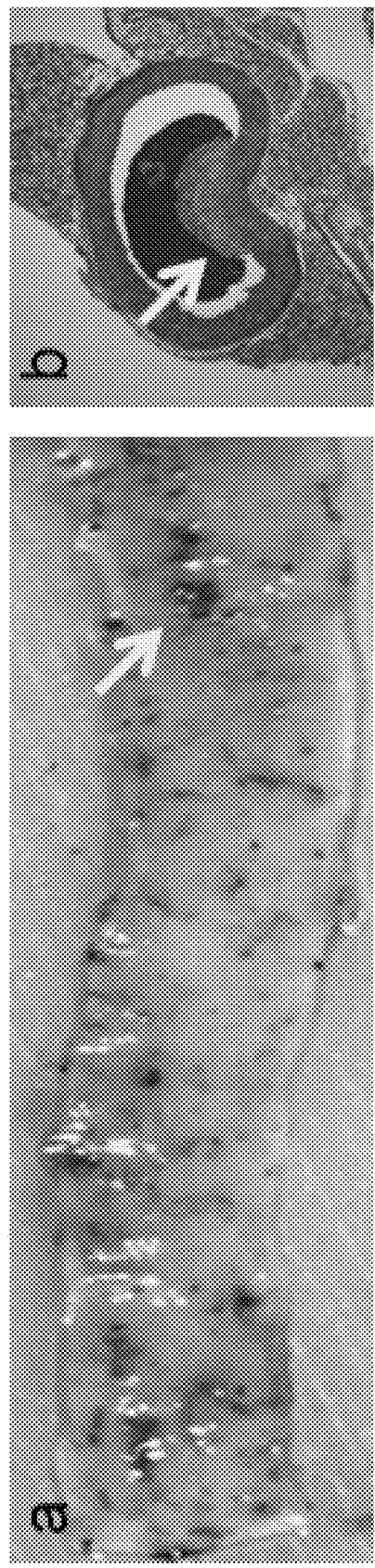
FIG. 14 shows evidence of atheroma development in the aorta of an ApoE-null mouse (approximately 1 yr old, male). Oil-Red O stained atheroma plaques were clearly visualized. (a) Oil-Red O staining of an ApoE-null aorta. Arrow shows an atherosclerotic plaque, and (b) H&E staining of a cross-section of an ApoE-null aorta, showing an atheroma plaque with associated thrombosis.
Figure 15:
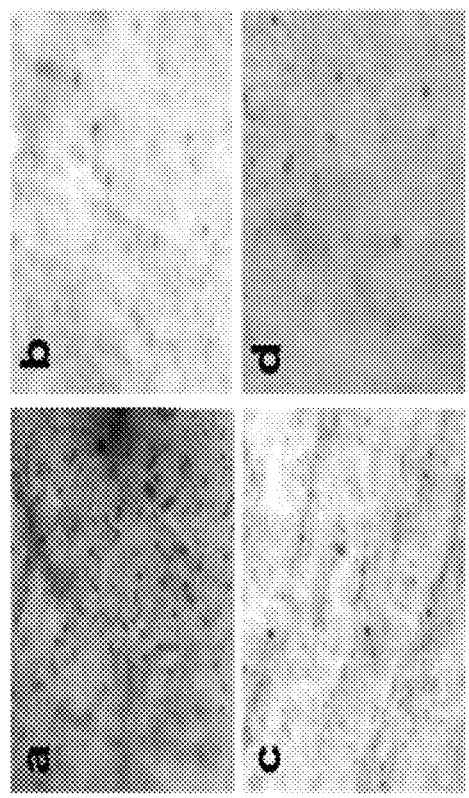
FIG. 15 shows the intensity of surface Oil Red O staining of bifunctional antibody targeted-ELIP-labeled cells attached to the endothelium of porcine aorta in the presence or absence of ultrasound. (a) bifunctional antibody targeted-ELIP-labeled CD34+ stem cells in the presence of ultrasound, (b) BF-ELIP-labeled CD34+ stem cells in the absence of ultrasound, (c) ELIP-IgG and CD34+ stem cells in the presence of ultrasound, (d) PBS and stem cells in the presence of ultrasound, and (e) quantification by morphometry revealed increased density of Oil Red O (ORO) staining in MSCs conjugated with BF and ultrasound treatment.
Figure 15:
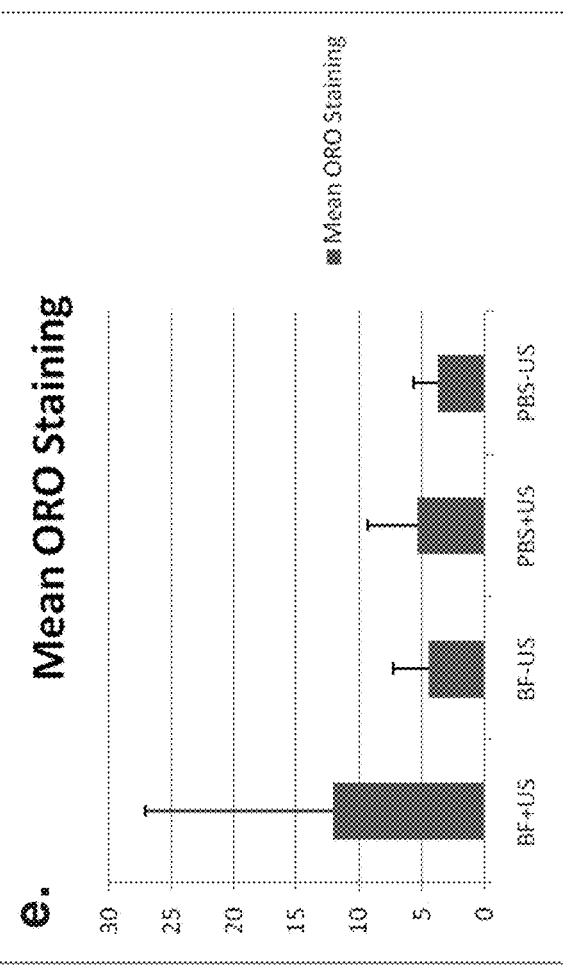

Positive staining for ORO on tissue, an indication of the presence of lipids, was expected to identify atheroma as well as the presence of liposomes on the surface of the aorta. The ApoE-null mice showed severe atherosclerotic lesions throughout the ascending, arch and descending aorta. The regions showing stronger echo signals were evidenced by macroscopically observed atherosclerotic plaques (FIG. 14). Additionally, quantification by morphometry revealed increased density of Oil Red O (ORO) staining in MSCs conjugated with BF and ultrasound treatment (FIG. 15).

3.1 Regression of Atheroma in ApoE-Null Mice after Targeted Stem Cell Delivery with Antibody Targeted-ELIP.

Figure 16:
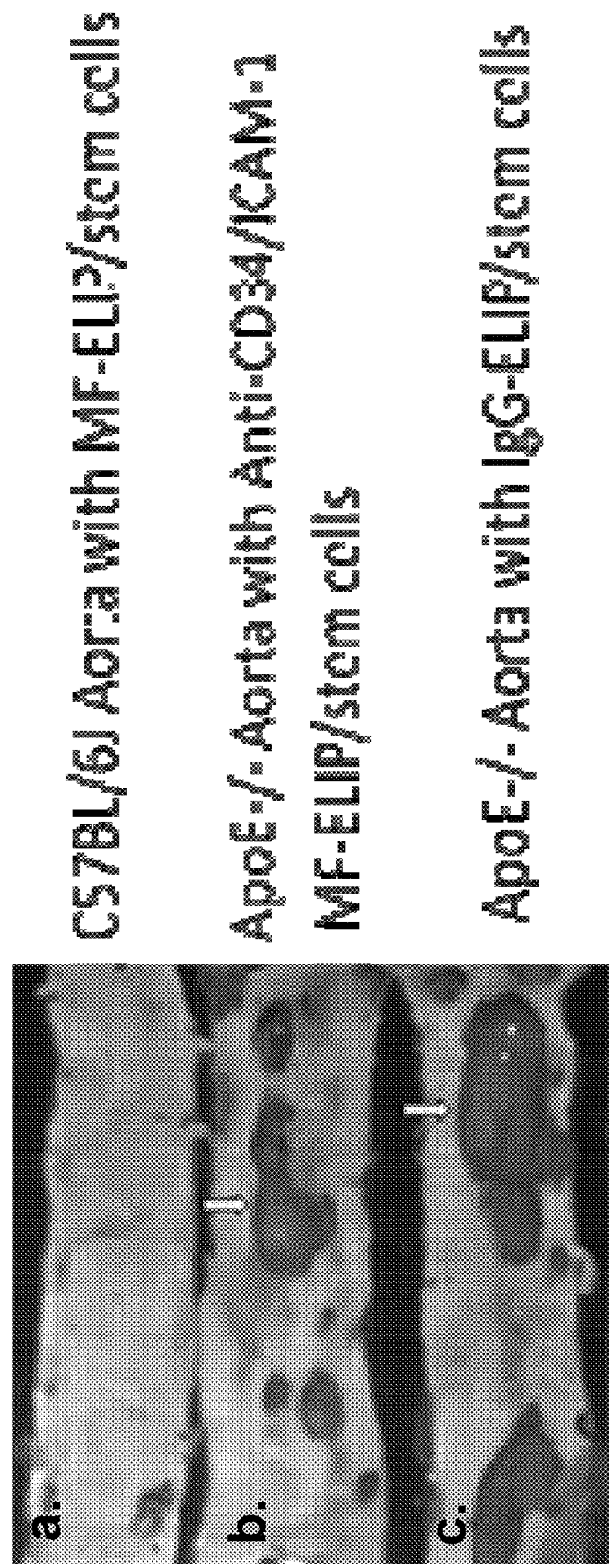
FIG. 16. Transplantation of bone marrow stem cells labeled with anti-CD34/ICAM-1 ELIP reduces atheroma in aortas of ApoE-null mice. Adult ApoE-null and normal C57BL/cJ mice were intravenously injected with anti-CD34/ICAM-1 ELIP-targeted bone marrow stem cells or control stem cells mixed with non-immune IgG-loaded ELIP. En face Oil Red O staining of aorta was performed 45 days after the cell transplantation. (a): Aorta of normal C57BL/6J mouse with anti-CD34/ICAM-1 ELIP-targeted bone marrow stem cells; (b) reduced plaques in the aorta of ApoE-null mouse injected with anti-CD34/ICAM-1 ELIP-targeted bone marrow stem cells; (c) plaques of the aorta of ApoE-null mouse injected with non-immune IgGELIP under the same condition as shown in (a) and (b). Representative images obtained from 5-6 mice per group. Arrows indicate staining by Oil Red O.

En face Oil Red O staining (yielding red color) was performed in the aortas harvested 45 days after wild type and apolipoprotein-E (ApoE) knockout C57BL/6J mice received bone marrow stem cells ($2\times10^6/25$ g body weight) targeted with MF-ELIP. These MF-ELIP were coupled to both CD34 and ICAM-1 antibody. Also included as control groups were wildtype and ApoE knockout mice that were treated with ELIP coupled to non-specific IgG. Ultrasound performed at 40-MHz B-Mode (Visual Sonics VEVO 770) on the vasculature of wild type mice treated with the MF-ELIP revealed little or no plaque signals as expected and this was confirmed in stained aortas (FIG. 16a). But the ApoE knockout mice treated with ELIP coupled to non-specific IgG had abundant evidence of atheroma, as shown in FIG. 16c. However, when ApoE knockout mice were treated with CD34 and ICAM-1 antibody bearing MF-ELIP, there was a significant reduction in atheroma detected as shown in FIG. 16b. These results demonstrate the efficacy of using antibody coupled-ELIP-targeted delivery of stem cells to prevent and treat atheroma.

Figure 17:
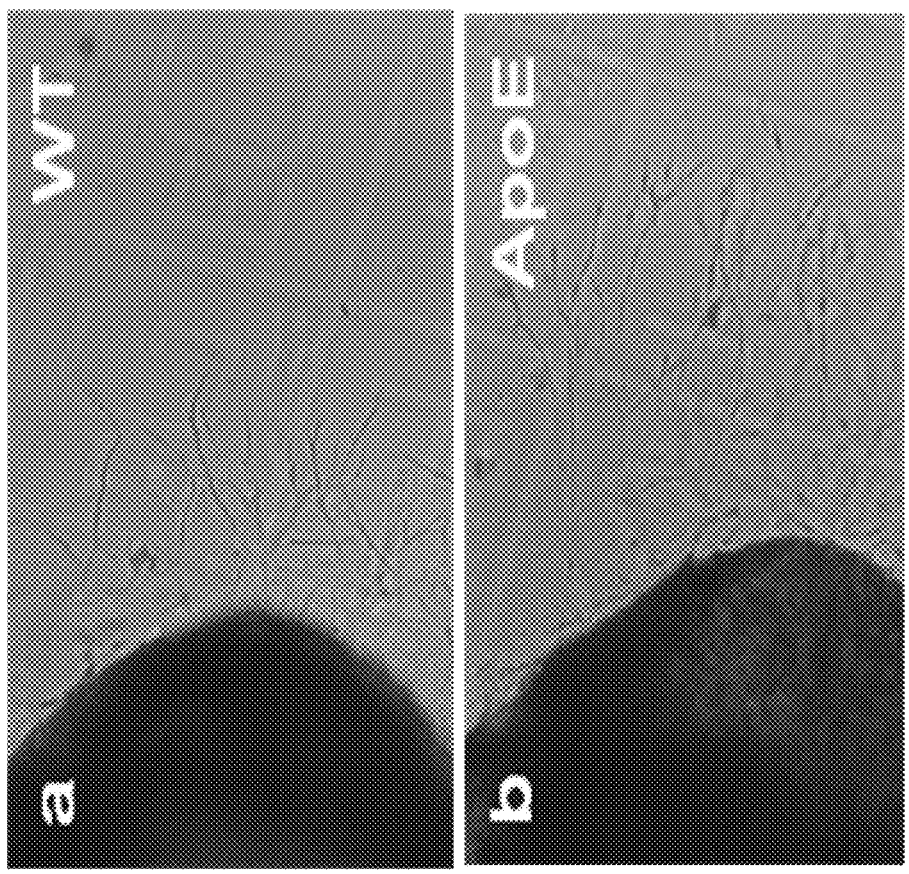
FIG. 17. Vascular outgrowth, shown as tubing network, in the aortic segments obtained from (a) wild type (WT) and (b) ApoE-null knockout mice.

To assess the survival and differentiation potential of antibody targeted-ELIP targeted vascular stem cells ex vivo 3D aortic tissue culture was done using the segments of aortas of ApoE-null and wild type mice. After 1-2 weeks, aortic tissue had outgrown and formed tubing structure in both ApoE-null mouse tissue (FIG. 17a) and wild type mouse tissue (FIG. 17b). Furthermore when grown in fibrin gel cultures, aortic segments obtained from ApoE-null mice appeared to experience increased vascular outgrowth as compared to those obtained from wild type mice.

3.2 Tetracycline (TCN)-Loaded ELIP.

ELIP loaded with tetracycline (TCN) are used to conduct targeted activation of a TCN-controlled ApoJ gene expression (described in detail below), as well as to control osteogenesis and should any arise bacterial pathogen infection in atherosclerotic lesions. It is known that both the osteogenesis and infections are prominent pathological features of atherosclerotic lesions. MSC can not only differentiate into SMC but also bone-forming cells such as chondrocytes and osteoblasts and TCN can inhibit the osteogenic process of MSC.

To formulate a TCN-ELIP, a stock solution of TCN in PBS is obtained and freshly prepared for each experiment. The drug is dissolved in deionized water and mixed with the same volume of 0.64 M mannitol. Phospholipids (total 5 mg) are dissolved in chloroform, rotary evaporated under argon until the chloroform has evaporated, leaving a thin dry film. 500 ml of TCN in mannitol solution is then added to the flask, and the flask shaken, and settled at room temperature for 30 min. The mixture is sonicated in a water bath for 5 minutes, and frozen at $-70°$ C. overnight. The frozen sample is lyophilized.

Varying ratios of drug:lipid (wt/wt) are prepared. Several iterations are anticipated to retain echogenicity as well as optimal drug-loading. All free drug is removed from the drug-liposomal preparation by centrifugation at 300 g for 10 min. Liposomes floating on top of the solution are collected as echogenic liposomes with TCN. The encapsulated, and unencapsulated TCN is measured by a spectrofluorometric method at an excitation 383.3 nm and an emission at 484 nm. Encapsulation efficiency is calculated. The composition that affords maximal echogenicity and stability consists of mixtures of saturated and unsaturated phosphatidylcholine combined with anionic lipids and cholesterol, and as appropriate a maleimido-phosphatidylethanolamine when antibody conjugation is required. The composition, echogenicity and stability are established and the echogenic properties of such liposomes are determined in concert with the incorporation efficiency. Compositional adjustments are done to ensure good encapsulation along with high echogenicity and stability.

Vascular Cell-Specific, TCN-Conditional ApoJ Transgenic Mice.

A conditional, tissue-specific transgenic expression system with modification was used to develop an ApoJ transgenic mouse strain with SM22-driven ApoJ conditional expression in vascular smooth muscle cells (FIG. 12). When fed TCN or its analog doxycycline, ApoJ expression increases dramatically in both the vessel wall and peripheral blood. ApoJ transgenic mice whose serum ApoJ levels increased 3-5 fold that of wild type controls. ApoJ transgenic mice also have higher levels of HDL have been developed.

Preparation of TCN-Multifunctional Antibody Targeted ELIP for Stem Cell Delivery and Activation of ApoJ Transgene.

A stock solution of TCN or its derivative deoxycholine in PBS is freshly prepared for each experiment. The drug is dissolved in deionized water and mixed with the same volume of 0.64 M mannitol. Phospholipids (total 5 mg) are dissolved in chloroform, rotary evaporated under argon until the chloroform is evaporated, leaving a thin dry film; 500 ml of TCN in mannitol solution is then be added to the flask, and the flask shaken, and settled at room temperature for 30 min. The mixture is sonicated in a water bath sonicator for 5 minutes, frozen at $-70$ degrees C. overnight. The frozen sample is lyophilized. Varying ratios of drug:lipid (wt/wt) are prepared. Several iterations are anticipated to retain echogenicity as well as optimal drug-loading. All free drug is removed from the drug-liposomal preparation by centrifugation at 300 g for 10 min. Liposomes floating on top of the solution are collected as ELIP with TCN. The encapsulated and unencapsulated TCN is measured by a spectrofluorometric method at an excitation 383.3 nm and an emission at 484 nm. Encapsulation efficiency is calculated. The TCN-ELIP is first tested in cultured cells transfected with full-length ApoJ cDNA. The ApoJ cDNA is ligated into the TCN-controlled expression plasmid, pTRE-tight-Bi-Zs-Green1, which can also express GFP (Clonetech, CA). To ensure effective expression of a trans-activator (rtTA) in stem cells, the CMV promoter in the TCN-ON Advanced vector (Invitrogen, CA) is replaced with a elongation factor 1 (EF-1) promoter. Both vectors, pTCN-EF1 and pTRE-tight-Zs-Green1, are co-transfected into bone marrow or fat tissue-derived stem cells. To analyze for protein expression, cells are incubated in the presence of various concentrations of deoxycholine (a derivative of TCN) for 24 hours at 37 degrees C. and subjected to electrophoresis and Western blot using antibodies to ApoJ. GFP fluorescence is detected using a Nikon Eclipse E800 microscope.

Injection of SC with TCN-Multifunctional Antibody Targeted ELIP into ApoJ Transgenic and Wild Type Mice.

Once the in vitro test of the TCN-multifunctional antibody targeted ELIP in transduction of ApoJ gene is confirmed successful, the TCN-multifunctional antibody targeted ELIP to stem cell and endothelial cell markers are delivered with or without stem cells into the murine models via intravenous or direct injection to the left ventricle. The dose of each injection is $10^4$ cells/2.5 mg ELIP/100 ul. ApoJ transgenic mice (n=10, both sexes, age 3-6 months) and age- and sex-matched wild-type mice are used in this study. Controls include mice treated with TCN-ELIP without antibodies.

By way of example but not limitation, following injection of TCN-ELIP targeted with antibodies to CD34 and ICAM, conditioned ApoJ transgenic mice and controls are closely monitored and imaging is performed. ELIP labeled stem cells are highly echogenic. The mice are anesthetized with a combination injection of Ketamine HCl (200 mg/kg) and Xylazine HCl (40 mg/kg) intraperitonealy. The animals are placed in a supine position on a heated table and cardiac function is monitored by EKG. For optimal imaging, the abdominal aorta is imaged with high frequency TVUS (VisualSonics Vevo 770, 40 MHz); images obtained are recorded on the internal hard drive. Images are obtained at baseline and following ELIP injections. Cardiovascular function is determined by ventricular wall motion and calculation of ejection fraction. Aortic wall motion is determined as an indicator of stiffness.

Also following the delivery of stem cells with TCN-ELIP, transgenic mice receive TCN in drinking water to induce expression of ApoJ and the level of ApoJ present in the peripheral blood of the ApoJ transgenic mice is determined using ELISA and Western blotting. To determine the level of ApoJ transgenic transcripts quantitative PCR and RNase protection assays are used. To determine if peripheral blood contains circulating VSC, flow cytometric analysis using labeled anti-Flk1, Tie2, CD31 antibodies is done. To determine the absolute number of VSC and the percentage of total mononuclear cells that are VSC, VSC are incubated with DiI-acetylated LDL, because VSC express scavenger receptor and are capable of taking up acetylated LDL the labeled cells are then identified and counted using fluorescent microscopy and/or flow cytometry.

To determine the level of expression of ApoJ transgenic mRNA in aortic tissues, total RNA is isolated from the aorta and reverse-transcribed into cDNA, and then amplified by PCR. A quantitative, real-time PCR cycler (SMART CYCLER, Cepheid, Suwanee, Ga.) is used to obtain real-time ApoJ expression. Alternatively, RNase protection assays are used wherein an ApoJ cDNA fragment is constructed and cloned into a plasmid vector to generate single strand templates for the protection assays.

ApoJ protein levels are determined using immunoblotting with anti-ApoJ antibodies. The total proteins are isolated and loaded into SDS-PAGE. Sections of aorta are deparaffinized and stained with rabbit anti-ApoJ antibodies for immunohistochemistry is used to localize ApoJ in atherosclerotic lesions. Anti-rabbit IgG conjugated with biotin is used as the secondary antibodies and an ABC kit (Vector) is used to develop the immunostains. To co-localize ApoJ with SMC and EC as well as VSC, double staining is performed with a combination of anti-ApoJ and anti-SM-α-actin or anti-CD31, markers respectively for the vascular cells.

ApoJ-transgenic/ApoE-null dual transgenic mice are generated by crossing ApoJ transgenic mice with ApoE-null mice. Because ApoJ is a secreted protein, the ApoJ transgene is initially driven under a tissue non-specific CMV promoter. However, to establish a tissue-specific expression, the SMC-specific promoter SM22 or endothelial cell-specific promoter Tie-2 are constructed and inserted upstream of rtTA fusion gene which encodes proteins controlling expression of the ApoJ transgene. ApoJ mice were crossed with ApoE-null mice to generate a dual transgenic mouse strain to determine the role of ApoJ in regulation of vascular cell apoptosis in atherosclerosis. After many generations of backcrossing, homozygous ApoJ-transgenic/ApoE-null mice were obtained, as well as single ApoJ-transgenic and ApoE-null mice alone.

Mice are examined at two ages (3 and 12 months) for each mouse strain. Each age group contains 8 mice (4 male and 4 female). Because the ApoE-null mice develop hyperlipidemia and atherosclerosis spontaneously when fed normal chow, they will not be feed on high-fat or high-cholesterol diets. The same numbers of control animals, matched in age, sex and genetic background (C57BL/c) are used as well. All the animals are closely monitored and peripheral blood lipid profiles of the animals are determined by using a Sigma lipid assay kit, under both fasting and normal diet conditions.

To establish the capacity for neovascularization or angiogenesis of VSC obtained from different transgenic ApoJ-transgenic, ApoE-null and ApoJ-transgenic/ApoE-null compound mice, VSC are isolated from the peripheral blood, adipose tissue and bone marrow of the mice. The VSC are sorted out after labeling with DiI-acetylated LDL (acLDL) and flk1. To track the cells of the vascular cell lineage, cells are tagged with AKT-GFP using adenoviral vector. The angiogenesis assays are performed using a minimal volume of Matrigel in 96 well plates (BD Biosciences, MA USA), that allows both tubule and vascular network formation.

The following cell types are used for the assay: human vascular endothelial cells (passages 2-5) as positive control, total unfractioned mononuclear cells, sorted ScR+ (acLDL-uptake) cells and ScR− cells. Before initiation of the assays, cells are grown for 72 hours in endothelial basal medium (EBM) supplemented with growth factors (2.5% FBS, hydrocortisone, human epidermal growth factor, 100 ng/mL vascular endothelial growth factor, basic fibroblast growth factor and heparin). At subconfluency, cells are incubated with DiI-acLDL (5 ug/mL) for 7 hours, and then changed to 10% fetal bovine serum and plated ($2 \times 10^5$) on Matrigel. Images of vascular tubes are acquired under an inverted microscope with Normaski and Texas Red channel with a 4× objective. The angiogenesis index is calculated using Metamorph software (Universal Corporation, West Chester, Pa.).

A 3D aortic outgrowth system, as described, is used to assess the function of MSC or VSC that are delivered selectively to atherosclerotic lesions with the ultrasound-BF-ELIP with antibodies bridging between stem cells and the vascular wall.

To allow histological analysis of atherosclerotic lesions, animals are sacrificed for analysis of atherosclerosis, apoptosis and ApoJ expression. The aortic tissue is divided into three parts: the aortic root, arch and descending aorta. The aortic root is used primarily for histopathological studies as this region is most sensitive to atherosclerosis and morphometrically easier for quantitative determination. The aortic arch will be used for RNA and protein extraction. The descending aorta will be used for vascular cell isolation. Routine histopathological examination will be conducted. The aortic tissue will be fixed in 10% formaldehyde. After dehydration, the tissue will be embedded in paraffin, sectioned and then stained with H&E. Stained sections will be examined under a bright field microscope. Images will be collected with a digital camera, and the atherosclerotic lesions are quantitatively determined by morphometry with a computer image station. To determine gross neutral lipid contents Oil-Red O staining or Nile-Red staining is done. Nuclear counterstaining is done with the DNA-binding fluorescent dye DAPI. After staining, the sections are mounted and examined under an Olympus microscope. The images of the arterial sections are collected by a digital camera and quantitative or semiquantitative analysis is conducted using a computer image station.

4.1 Ultrasound Treatment of Antibody Targeted-ELIP Enhances Stem Cell Adhesion to Activated Endothelium.

Because the porcine atheroma model more closely mimics human atheroma development, it was determined that MSC and VSC delivered to atherosclerotic lesions by ultrasound-antibody targeted-ELIP enhancement promotes progression or regression of atheroma developed in porcine arteries. The clear efficacy of human stem cells coupled to MF-ELIP as an effective delivery and activity enhancement mechanism in the well accepted model of human atheroma, i.e., porcine atheroma, strongly supports the use of a MF-ELIP-stem cell delivery mechanism to treat atheroma in other mammals, including humans, who suffer from atheroma.

To demonstrate that MSC and VSC delivered to atherosclerotic lesions by ultrasound activated-antibody targeted-ELIP promote progression or regression of atheroma developed in porcine arteries. Mononuclear cells were isolated from porcine bone marrow or subcutaneous fat were incubated with antibody targeted-ELIP coated with anti-CD34 and ICAM antibodies as well as the red fluorescent dye rhodamine B. After free ELIP were removed by aspiration, the labeled cells were loaded on the lumen surface of porcine aortic segments and ultrasonicated (SONITRON 1000

Figure 18:
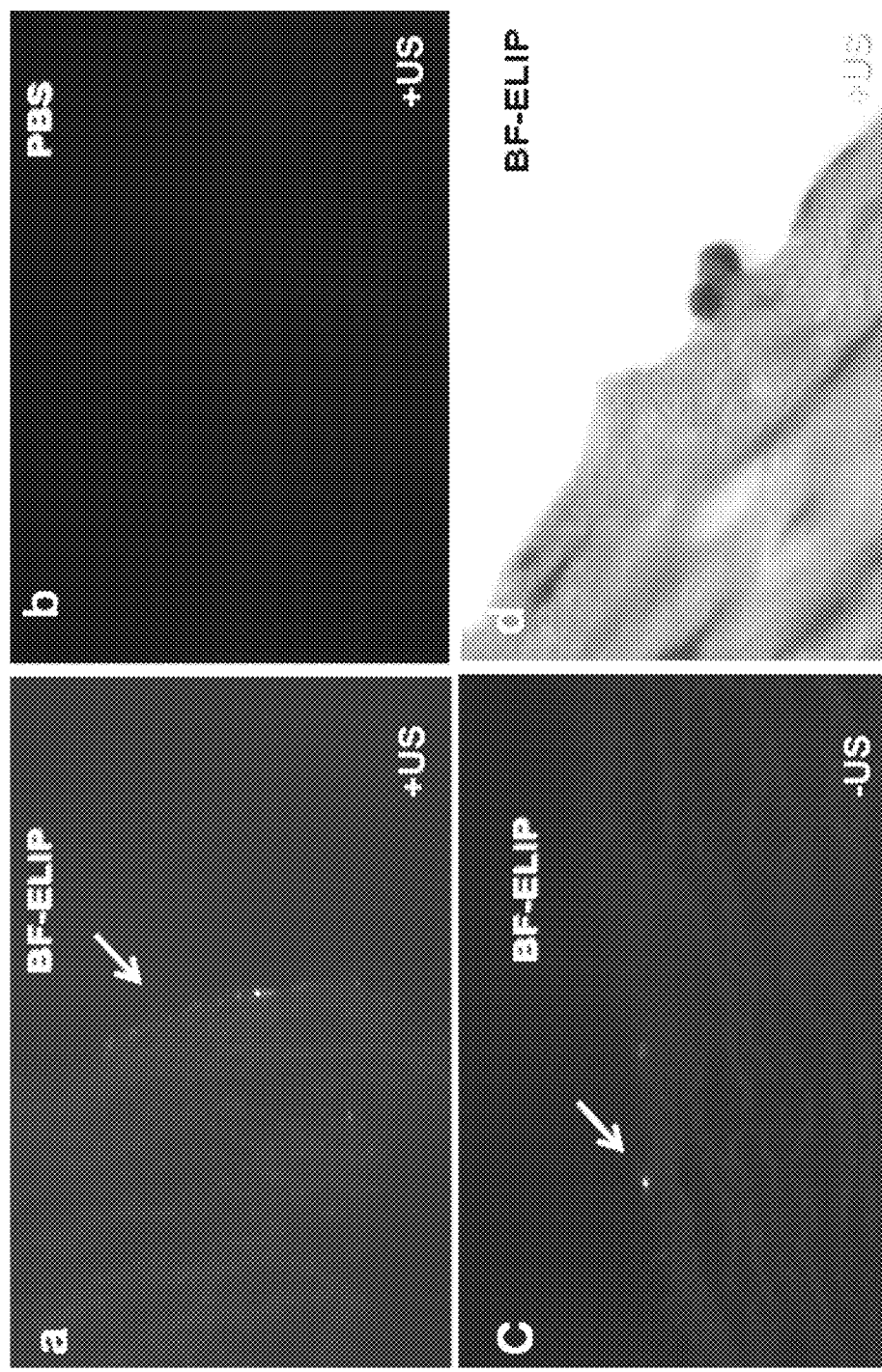
FIG. 18. is a group of photomicrographs evidencing bifunctional-ELIP targeted delivery of CD34+ bone marrow cells to porcine aortic surface with ultrasound (US) enhancement. (a):fluorescence of rhodamine containing bifunctional-ELIP-bound with ultrasound treatment (bright spots); (b):cells in PBS treated with ultrasound, (c):rhodamine containing bifunctional-ELIP-bound cells without US; and (d): H&E staining of a parallel section of the same aorta shown in (a). Arrows point out bifunctional-ELIP-targeted CD34+ cells attached to the endothelium.

RICH-MAR, 1 MHz, 0.5 W/cm$^2$; 100% duty cycle for 30 sec). The aortic segments were washed in PBS, and then fixed in 4% paraformaldehyde or frozen in OCT medium for histological studies. The antibody targeted-ELIP labeled cells on the surface of endothelium were clearly detected by fluorescence microscopy, which illustrated numerous red fluorescence on the surface of the aortas with ultrasound enhancement (FIG. 18). The ultrasound treatment (FIG. 18 a) significantly increased the attachment of antibody targeted-ELIP-stem cells to the aorta, as only a few stained areas were observed scattered about the surface of the aorta in the absence of ultrasound treatment (FIG. 18 c). The PBS treatment control did not show any red fluorescence (FIG. 18 b). H&E staining of the tissue confirmed that antibody targeted-ELIP-targeted delivery increased the successful targeting of mononuclear cells to the endothelium (FIG. 18 d). Without being limited to any particular theory, it is thought that in some embodiments ultrasound with an energy at non-cytotoxic levels may enhance the stem cell adhesion and transmigration through endothelium by cavitation and bursting out ELIPs, which allows a firm attachment of stem cells to endothelium.

4.2 Endothelial Attachment of Antibody Targeted-ELIP-CD34+ Cells by SEM.

Figure 19:
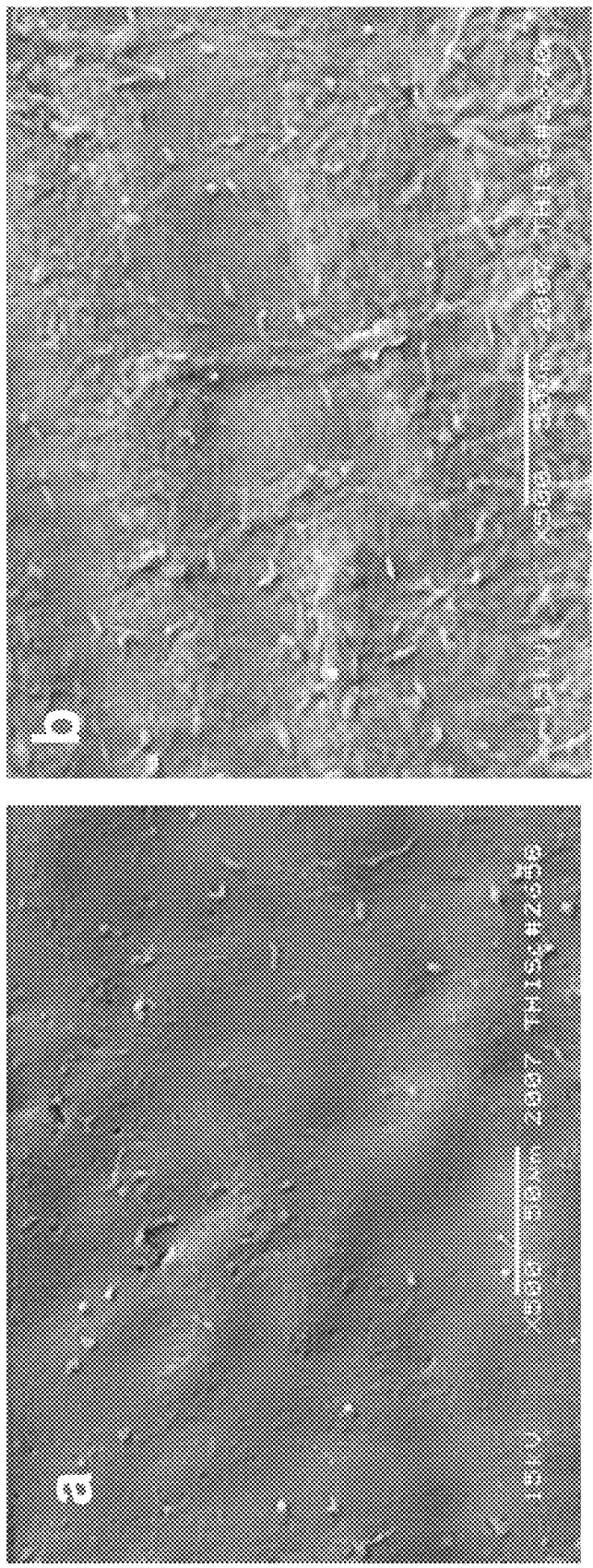
FIG. 19 is a scanning electron micrograph of the lumal surface of a porcine aorta with CD34+ cell attachment enhanced by the BF-ELIP-ultrasound treatment. (a): only scattered cell attachment is present in the normal aortic surface and (b): greatly increased amounts of cells are attached and penetrate in the region of fatty streaks.

The attachment of antibody targeted-ELIP-labeled stem cells to the aortic tissue was further demonstrated using scanning electron microscopy (SEM). The aortic surface was scanned using the JEOL JSM-6460 scanning electron microscope in the LV SEM mode. This revealed that there were numerous antibody targeted-ELIP-stem cells attached on the lumen surface of aortas as shown in FIG. 19. Compared to the areas of the aorta that contained fine endothelium (FIG. 19a), the areas containing fatty streaks had much greater numbers of stem cells attached on its surface (FIG. 19b), and some of these cells appeared to penetrate the endothelial layer. Thus, ultrasound therapy did enhance the attachment and penetration of the antibody targeted ELIP-labeled stem cells to the arterial wall in regions of atherosclerotic lesions.

4.3 Immunohistochemical Identification of Vascular Stem Cells in Atherosclerotic Arterial Tissue.

Figure 20:
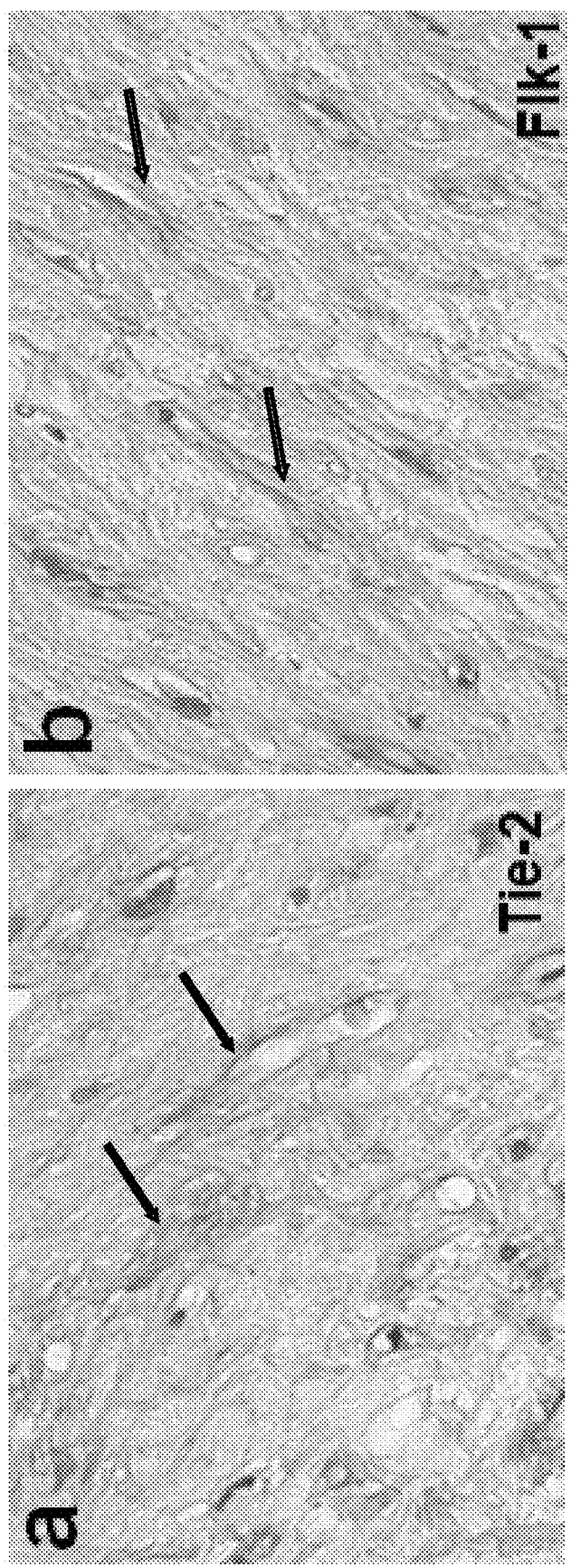
FIG. 20 shows immunohistochemical staining for Tie-2 and Flk-1 in human atherosclerotic aortic tissue. Sections were stained with anti-Tie-2 and Flk-1 antibodies. Bound antibody was detected using biotinylated second antibodies and avidin-AKP system with Fast Red as the substrate. Immunostains shown in red color appear as dark grey regions (arrows) and hematoxyline nuclear counterstain is blue, but which appears light grey in the figure.

To identify VSC cells in atherosclerotic arterial tissues and demonstrate that these lesions contain reduced levels of VSC, immunohistochemical staining was used for detection of vascular stem cells in the arterial wall. VSC bear several biomarkers, such as Flk-1 and Tie-2. Therefore, paraffin embedded sections were prepared and stained using labeled antibodies that bind Flk-1 and Tie-2. The results, shown in FIG. 20, showed that both Tie-2 and Flk-1 proteins could be identified in arterial tissues and in particular in the smooth muscle multi-layers.

Figure 21:
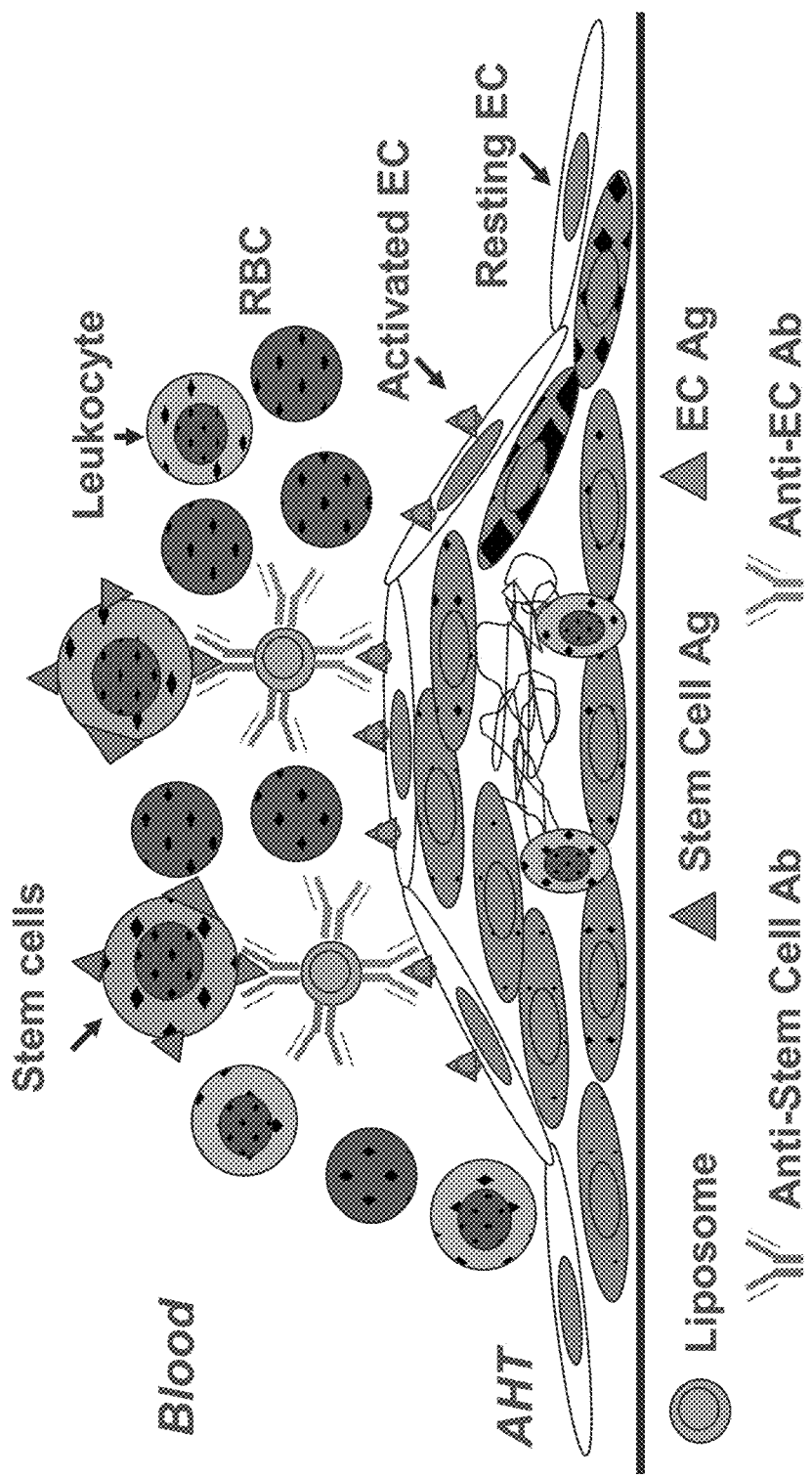
FIG. 21 is a schematic illustration of a bifunctional-ELIP-bridging of stem cells to the activated endothelium covering ATH. AHT, atheroma; Ag, antigen; Ab, antibody; EC, endothelial cells; RBC, red blood cells.

Having demonstrated the activity of multi-functional antibody targeted-ELIP in vivo using murine stem cells, and in the porcine atheroma model which more closely mimics human atheroma development, it is believed that similar results will extend to treatment of human atheroma and diabetes. In accordance with certain embodiments, an above-described bifunctional echogenic liposomes (BF-ELIP) is used to target stem cells to atheromas. In some embodiments a multifunctional echogenic liposome (MF-ELIP) is provided, and in some embodiments the MF-ELIP is used to target stem cells to atheroma or other target tissues. For example, in some embodiments the target tissue is a lesion in a blood vessel of a person with atherosclerosis or diabetes, and in some embodiments the target tissue is a wound or site of inflammation and in still other embodiments that target tissue is highly vascularized, such tissues include but are not limited to, heart, spleen, liver and lung. A bifunctional ELIP is one that has 2 types of antibodies with different specificities attached, one of which binds to the stem cell of interest and the other that binds to the marker on the atheroma, or other target tissue. For example, as schematically illustrated in FIG. 21, the resulting BF-ELIP structure comprises a stem cell (approx 12-15 microns in diameter) coupled to an echogenic liposome (about 1-2 microns) which, in turn, is coupled to an atheroma on an arterial wall of a patient. The multifunctional version (MF-ELIP) incorporates additional antibodies (more than two) that either strengthens the binding of the stem cell (e.g., via a second marker) or strengthens the targeting of the atheroma. The additional antibody or antibodies may in some cases have a negative activity, i.e., that blocks the binding of a predetermined marker, thus enhancing stem cell survival or stimulating the cell or atheroma to express something that increases survival or activity or differentiation of the stem cells to cells that stabilize the plaque (atheroma), for example.

The incorporation of a third or more antibodies that bind additional markers on either the stem cells or the atheroma (target tissue), provides the added benefit of being able to more specifically identify the target cell or the stem cell desired. For example, sometimes more than one type of cell will share the same marker (antigenic determinant). This can occur for example, if they derive from the same precursor lineage. However, as the cells develop further they can also begin to express additional markers unique to their line as the result of developing specific functions or their particular developmental stage. Thus, the ability to add a third (or more) selecting antibody can result in greater specificity in the selection process, as well as enhanced (stronger) binding of the MF-ELIP.

The incorporation of a third or more antibodies that bind additional markers that are shared by both the stem cells and the target tissue (atheroma), provides the added benefit of being able to strengthen the binding of the stem cell-ELIP-target tissue complex. This not only makes the interaction more stable, but it also increases specificity because the multi-functional-ELIP now has two determinants that it binds on the target tissue, or on the stem cell or on both the target tissue and the stem cell, when for example the multi-functional ELIP contains four different types of antibodies.

In some embodiments, the BF-ELIP or MF-ELIP combines the use of cytokines or DNA in the ELIP along with multiple targeting antibodies. In various embodiments, the ELIPs, which are readily detected via ultrasound, are filled with genes, or gene products, or drugs that facilitate stem cell survival/activity or differentiation. For example, in some embodiments, tetracycline or ApoJ (clusterin)-filled ELIPS are used to image the presence of stem cells at the atheroma, via ultrasound detection techniques, and the ultrasound also stimulates release of the contents of the ELIP in close proximity to the stem cells at the site of the atheroma. Thus, the targeting of the antibody element is combined with the delivery and controlled release of liposome contents that will enhance the stem cells activity at the site of action.

In some embodiments, specific MF-ELIP are subjected to are subjected to lower energy ultrasound which is sufficient to allow monitoring of their in vivo location (i.e., "imaging ultrasound"), but not sufficient to also induce release of the active agents (drugs, genes, or stem cell enhancing agents). The release-inducing ultrasound is higher energy than the US used for tracking. The release-inducing ultrasound is higher energy than the US used for tracking. B-mode ultrasound, used for monitoring of the ELIP in vivo locations, do not provide cavitation effects, whereas therapeutic (such as pulsed Doppler) ultrasound does.

In some other embodiments, ultrasound-inducible release is not required for the release of bioactivity of a MF-ELIP, because in some cases, the liposomes are formulated to be sufficiently permeable to allow the active agents (such as drugs, genes or stem cell enhancing agents) to be passively eluted at the target site or released as a consequence of conditions that develop at the site of interaction between the stem cell and target site. Alternatively, any other suitable means of controlled release may be employed, as are known for releasing substances from liposomes.

5.0. Local Administration of NO-ELIP Significantly Inhibited Development of Neointimal Hyperplasia in a Rabbit Atherogenesis Model.

The encapsulation of air into these liposomal formulations results in a contrast agent that is suitable for ultrasound image enhancement and controlled release of therapeutic agents, while being stable in the circulation for a prolonged period. The encapsulated NO was effectively sequestered from hemoglobin scavenging and local administration of NO-ELIP significantly inhibited development of neointimal hyperplasia in a rabbit atherogenesis model. A major advantage of the ELIP formulation for use with these liposomes is that they can be readily targeted to pathologic structures by conjugation of antibodies and other ligands to the phosphatidyl ethanolamine head groups. Preliminary studies demonstrated, however, that conjugation of antibodies directly to NO-loaded ELIP resulted in >90% loss of antibody immunoreactivity, mainly due to protein denaturation induced by gas pressurization and freeze-thawing procedures.

Gas entrapping microbubbles have proven difficult to target with protein ligands, because of denaturation during the microbubble preparation procedure. This difficulty can be largely obviated by coupling the targeting ligands to preformed microbubbles using biotin/avidin linkage technology. There is a similar propensity to denaturation of antibodies conjugated to liposomes, when subjected to pressurization and freeze-thawing procedures required to encapsulate bioactive gases. Recently, microbubble-liposome complexes, have been produced using biotin/avidin linkage technology, in order to improve the drug-delivery capacity of microbubbles. Intrinsically echogenic liposomes (ELIP) compare favorably to microbubbles in terms of in vivo stability and targeting capabilities, as well as drug and gene delivery capacities. Thus, utilization of the biotin/avidin linkage strategy to form multi-liposomal complexes may not only surmount the barrier to site-specific delivery of bioactive gases encapsulated in ELIP, but also may enhance the utility and versatility of the ELIP technology's therapeutic potential.

A 4:1 ratio of available biotin between gas-loaded and targeted ELIP, respectively, with an equal proportion, by weight, of both types of liposomes was chosen to favor formation of complexes likely to feature targeted ELIP modules at the surface, where they would be available for binding to their molecular targets. Fluorescence deconvolution microscopy confirmed that, while targeted modules were not preferentially situated on the complex periphery, some were available for binding at the surface in most aggregates. Although some large aggregates of up to 500 liposomes were observed, most were ≤3 μm in diameter. Beckman Coulter Multisizer 3 analysis indicated that more than 20% of liposomes were aggregated, but that complexes ≥2 μm in size comprised 2.4% of the particle population, suggesting that the average aggregate consisted of approximately 8 liposomes, which is consistent with the observed size of the complexes. Dual-labeled particles enumerated by flow cytometry comprised 1.2% of the total, further suggesting that half of the complexes were monotypic. As expected for biotin-avidin interactions, which are characterized by very high affinity associations, complex formation was essentially complete within 1 min. This demonstrates that bioactive gas delivery with essentially full retention of echogenicity and targeting capabilities can be achieved. Both characteristics were somewhat decreased in monotypic targeted ELIP complexes, produced by addition of streptavidin to Ab-bELIP, without NO-loaded bELIP modules, probably because of steric factors. Interestingly, no such impairment was seen with the mixed aggregates, confirming that a sufficient proportion of targeting modules was maintained on the periphery of complexes to preserve their targeting capacity and that the NO-loaded bELIP were highly echogenic. More important, a 225% enhancement of bifunctional ELIP-potentiated stem cell passage through endothelial cell monolayers in vitro demonstrated the functional utility of the modular complex strategy, while simultaneously supporting several hypotheses. First, modular ELIP complexes can deliver liposome-encapsulated bioactive gases to specific cellular sites. Second, nitric oxide delivered in this manner increased the permeability of endothelial cell monolayers to stem cells, establishing a mode of enhanced perivascular and intravascular delivery of a range of therapeutic agents, including entire cells.

Bifunctionally targeted liposomes, conjugated to antibodies specific for both a stem cell marker and an adhesion molecule expressed by inflammatory endothelium (in this case, CD34 and ICAM-1, respectively), were developed as a means of bridging stem cells and atheroma. To demonstrate BF-ELIP bridging function a transwell system was employed because it also offered an effective means to establish that the targeted ELIP modular complex strategy increases endothelial permeability. The number of HMNC migrating through endothelial cell monolayers under conditions of NO-enhanced permeability was relatively consistent (CV=21% for 3 experiments), while variability was higher (CV>35%) without site-specific NO enhancement. Thus was established an in vitro method for evaluation of ELIP modular complexes. Evidencing that the ELIP modular complex strategy has great potential for facilitating targeted delivery of therapeutic agents that may otherwise interfere with targeting strategies.

Preparation of Standard ELIP:

A 27:42:8:8:15 molar ratio of the lipid components 1-α-phosphatidylcholine (chicken egg; EPC), 1,2-dipalmitoyl-sn-glycero-3-phosphocholine (DPPC), 1,2-dipalmitoyl-sn-glycero-3-[phosphor-rac-1-glycerol] (DPPG), 1,2-dipalmitoyl-sn-glycero-3-phosphoethanolamine (DPPE), and cholesterol (CH) were mixed in a round-bottom flask as chloroform solutions. For preparation of fluorescent ELIP, 0.2 mol. % lissamine rhodamine B-DPPE or carboxyfluorescein-dioleoyl PE (Avanti Polar Lipids) was included in the formulation, which was subsequently protected from exposure to light. The chloroform was then removed by evaporation under argon, while the flask was rotated in a 50° C. water bath. The resulting lipid film was placed under vacuum for 4 h at ≤100 mTorr pressure for complete removal of the solvent, followed by rehydration of the dry lipid film with 0.32 M mannitol to a concentration of 10 mg lipid/ml. The hydrated lipid was incubated at 55° C. for 30 min to ensure that all lipids were in the liquid phase during hydration. The mixture was then sonicated in a water bath for 5 min. Aliquots of the suspension were frozen at −80° C.

and lyophilized for 24-48 h. Each lyophilized dry cake was resuspended with the original volume of nanopure water immediately before use.

Preparation of NO-ELIP:

Liposomes of the above composition were prepared according to a previously developed pressurization-freeze method (as described in S. L. Huang, P. Kee, H. Kim, M. R. Moody, S. M. Chrzanowski, R. C. MacDonald and D. D. McPherson, Nitric oxide loaded echogenic liposomes for nitric oxide delivery and inhibition of intimal hyperplasia, *J. Am. Coll. Cardiol.* 54 (7) (2009), pp. 652-659). Briefly, after drying and hydrating the lipid film, 300-μl aliquots of the suspension were transferred to 2-ml borosilicate glass vials (12×32 mm), which were then sealed with Teflon-coated silicon rubber septal screw caps. Nitric oxide (5.4 ml STP), washed and purified by passage through a saturated sodium hydroxide solution in order to remove nitrogen dioxide produced by contaminating oxygen, or a mixture of NO and argon was introduced into each vial through the septum and pressurized to 9 atm using a syringe fitted with a 27 G×½" needle. The pressurized gas/liposome dispersion was incubated for 30 min at room temperature, followed by freezing on dry ice for ≥30 min. Vials were stored at −80° C. Prior to use, the pressure was released by loosening the caps immediately after removal from storage, followed by thawing of the NO-ELIP suspension at room temperature.

Preparation of Control, Fibrinogen and Bifunctional (Stem Cell and ICAM-1) Targeted ELIP:

For conjugation, anionic ELIP were prepared as described above, substituting 1,2-dipalmitoyl-sn-glycero-3-phosphoethanolamine-N-[4-(p-maleimidophenyl) butyrate] (MPB-PE) for PE. For preparation of bifunctional targeted ELIP (BF-ELIP), monoclonal anti-human/mouse ICAM-1 (0.2 mg)+0.2 mg rabbit anti-human/mouse CD34 (both from Santa Cruz Biotechnology, Inc.)+1.6 mg nonspecific mouse IgG were reacted with 3-(2-pyridyldithiolpropionic acid)-N-hydroxysuccinimide ester (SPDP) at a SPDP-protein molar ratio of 15:1 for 30 min at room temperature (RT). For a control preparation, 2 mg of nonspecific IgG was used without specific antibody (Ab). For fibrinogen targeting, 2 mg of rabbit anti-human fibrin(ogen) Ab (American Diagnostica, Inc.) was utilized. Protein was separated from unreacted SPDP by gel chromatography on a 50 ml Sephadex G-50 column equilibrated with 0.05 M citrate-phosphate buffer, pH 5.5. Protein fractions were identified (optical absorbance at 280 nm, A280), pooled and concentrated to ≤2 ml using Centricon YM-10 centrifugal filter units. The PDP-protein was reduced in 25 mM dithiothreitol (DTT) for 30 min at RT. The thiolated protein was isolated (G-50 column), equilibrated and eluted with pH 6.7 citrate-phosphate buffer. Protein-containing fractions were pooled and concentrated. The thiolated protein was reacted with 30 mg of reconstituted MPB-ELIP (10 mg lipid/ml 0.1 M phosphate buffer, pH 6.62) under argon overnight at RT. Conjugated ELIP were separated from free protein and low molecular weight products by gel filtration on a 20-ml Sepharose CL-4B column that had been pre-saturated with unconjugated ELIP according to the method of Lasch J, et al., 2003 (M. Preparation of liposomes. In Torchilin, V. P., Weissig, V. eds. Liposomes, 2nd Ed. New York: Oxford University Press, pp 24-25) and eluted with 0.02 M phosphate-buffered saline (PBS), pH 7.4. Liposome-containing fractions were identified by optical absorbance at 440 nm prior to elution of free IgG, established during calibration of the column. The pooled liposome fraction was lyophilized in the presence of 0.1 M D-mannitol. Conjugation efficiency (CE; in pg Ab/mg lipid) of IgG- or Ab-ELIP was determined by quantitative immunoblot assay (as described in M. E. Klegerman, A. J. Hamilton, S. L. Huang, S. D. Tiukinhoy, A. A. Khan, R. C. MacDonald and D. D. McPherson, Quantitative immunoblot assay for assessment of liposomal antibody conjugation efficiency. *Anal. Biochem.* 300:46-52) relative to a composite curve of IgG-ELIP secondary standards. Ab-ELIP size distribution and number were determined with a Coulter Multisizer 3, fitted with a 20 μm aperture tube, which permits sizing down to 400 nm equivalent spherical diameter. Based on the number of liposomes, CE is also expressed as the number of Ab molecules per liposome.

Liposome Biotinylation and Complex Formation:

ELIP were prepared with 8 mol. % biotinyl-DPPE (instead of DPPE) for NO loading and with 2 mol. % biotinyl-PE (in addition to the 8 mol. % MPB-PE, while decreasing the DPPC content by 2 mol. %) for IgG or Ab conjugation. Complex formation was initiated by addition of excess streptavidin (a 20 μg/ml solution equal in volume to the IgG-ELIP component) to equal proportions (by weight) of the two preparations.

Enzyme-Linked Immunosorbant Assay (ELISA) Characterization of Fibrinogen-Targeted and Bifunctional ELIP:

The direct ELISA protocol for evaluation of fibrinogen-targeted ELIP was described previously (Lasch, et al.). A sandwich ELISA protocol was used to determine the antiICAM-1 immunoreactivity of BF-ELIP. Nunc MaxiSorp microtiter plates were coated with 5 μg/ml of a polyclonal anti-human ICAM-1 capture Ab (R&D Systems) in 0.05 M sodium bicarbonate, pH 9.6, overnight at 4° C. All incubation volumes were 50 μl/well. One-third of the wells were left uncoated for determination of nonspecific binding. After aspirating well contents, all wells were blocked with conjugate buffer (1% bovine serum albumin in 0.05 M Tris buffer, pH 8.0, with 0.02% sodium azide) for 1 h. All incubations were at 37° C. Each incubation was followed by aspiration of well contents and washes (3×) with PBS-T (0.02 M phosphate-buffered saline, pH 7.4, with 0.05% Tween 20). All wells were then incubated with 200 ng/ml of recombinant soluble human ICAM-1 (Bender MedSystems) in 0.1% BSA/PBS-T diluent for 2 h. For assay of intact Ab-ELIP, wells were washed with PBS after this incubation and the first wash after the Ab-ELIP incubation was also with PBS. Various dilutions of antiICAM-1 Ab and Ab-ELIP (both in PBS) were incubated for 1 h, followed by a 1-hour incubation with 1:1000 goat anti-mouse IgG-alkaline phosphatase (Bio-Rad Laboratories) in conjugate buffer. The substrate incubation consisted of 50 μl of substrate buffer (0.05 M glycine buffer, pH 10.5, with 1.5 mM magnesium chloride)+50 μl p-nitrophenyl phosphate (Sigma Chem. Co.; 4 mg/ml) in substrate buffer per well for 15 min. The reaction was stopped with 50 μl 1 M sodium hydroxide per well.

The optical absorbance of each well at 405 nm (A405) was measured with a Tecan Safire2 microplate reader. Net A405 was determined by subtracting the absorbance of background wells from that of capture Ab-coated wells. The dissociation constant (KD) of Ab-ELIP binding to rshICAM-1 was derived as b of y=ax/(b+x) from a hyperbolic fit of the ELISA data (y=Net A405, x=[Ab]) performed with SigmaPlot software. Antibody concentration ([Ab]) for Ab-ELIP was calculated from the CE. KD values were corrected for perturbation of equilibrium conditions during the anti-mouse IgG-AP incubation according to a modification of Underwood (P. A. Underwood, Problems and pitfalls with measurement of antibody affinity using solid phase binding in the ELISA, *J. Immunol. Methods* 164 (1) (1993), pp.

119-130; M. E. Klegerman, S. Huang, D. Parikh, J. Martinez, S. M. Demos, H. A. Onyuksel and D. D. McPherson, Lipid contribution to the affinity of antigen association with specific antibodies conjugated to liposomes, *Biochim. Biophys. Acta* 1768 (7) (2007), pp. 1703-1716) Loss of immunoreactivity in ELIP complexes was determined by measuring [Ab] relative to the antiICAM-1 standard in the ELISA and setting an Ab-ELIP control (without NO-ELIP or streptavidin) equal to 100% immunoreactivity.

Echogenicity Analysis:

The liposomes were imaged with a 15 MHz intravascular ultrasound (IVUS) catheter in a glass vial, utilizing a modified CVIS IVUS system (Boston Scientific Inc.). Relative echogenicity (apparent brightness) of the liposome formulations was objectively assessed using computer-assisted videodensitometry. This process involved image acquisition, pre-processing, and gray scale quantification. All image processing and analyses were performed with Image Pro-Plus Software (Ver. 4.1, Media Cybernetics, Silver Spring, Md.). Images were digitized to 640×480-pixel spatial resolution (approximately 0.045 mm/pixel) and 8-bit (256 level) gray scale. For a pixel in an 8-bit bitmap image, an intensity value of 0 corresponds to no ultrasound reflectivity (black), while a value of 255 signifies maximal reflectivity (white). Data are reported as mean gray scale values (MGSV).

Fluorescence Deconvolution Microscopy:

Biotinylated IgG-conjugated and NO-loaded ELIP were labeled with rhodamine B and fluorescein, respectively, as described above. A cover slip precoated with 0.1% poly-1-lysine was covered with a fivefold dilution of the mixed liposomal suspension 10 and 30 min after initiation of complex formation. After removal of excess fluid, the cover slip was inverted and mounted on a microscope slide with Elvanol anti fade (DuPont, Wilmington, Del.). The slides were scanned with an Applied Precision DeltaVision Fluorescence Deconvolution System (Applied Precision, Issaquah, Wash.) fitted with an Olympus IX-70 inverted microscope, followed by 3D image reconstruction as previously described (B. J. Poindexter, Immunofluorescence deconvolution microscopy and image reconstruction of human defensins in normal and burned skin, *J. Burns Wounds* 4 (2005), p. e7). Image analysis was with Soft-WoRx™ software (Applied Precision, Issaquah, Wash.), using a point-spread function, algorithm method. All data sets were subjected to five deconvolution iterations and then used for image reconstruction and modeling. Stacking of individual sections produces a three dimensional image on a two dimensional background, resulting in an image projection.

Flow Cytometry:

ELIP complexes were prepared with biotinylated fluorescein-labeled NO-loaded ELIP (NO-bELIP) and unlabeled IgG-bELIP. Two-color analyses were performed on the individual ELIP component controls and the complexes, 5 and 30 min after initiation, stained with anti-mouse IgG-phycoerythrin (Novus Biologicals, Littleton, Colo.), using a FACS Canto II (BD Biosciences), which has 3-laser, 8 color capacity, and BD FACS Diva 6.1.1 software.

Transwell System for Measurement of BF-ELIP Facilitation of Stem Cell Passage Through Endothelial Cell Monolayers:

Human coronary artery endothelial cells (HCAEC) were grown to confluence in 24-well transwell insert plates (8 μm pores; Corning Life Sci., Lowell, Mass.) and were then pre-treated overnight with TNF-α (20 ng/ml IMDM). IgG- or BF-bELIP (120 μg lipid/well), sterilized by ultraviolet light for 60 min, with and without complexed NO-bELIP (UV-sterilized for 15 min), was incubated with the cells for 5 min at 37° C. in an atmosphere of 5% $CO_2$/95% air, followed by a single wash with Dulbecco's PBS (DPBS). DAPI-stained or GFP-transfected human peripheral blood mononuclear cells (HMNC), isolated from buffy coat by Ficoll-Paque (Sigma-Aldrich) density gradient centrifugation (4×10$^4$ cells/well), were added to the wells and allowed to incubate under the same conditions for 5 min, followed by a single wash. IMDM (200 μl) was then added to the inserts and the plates were incubated under the same conditions for 24 h, after which all cells were removed from the apical membrane surface with a cotton swab. Cells that had migrated to the underside of the membrane were examined and enumerated by fluorescence microscopy with a Nikon Eclipse E800 microscope.

Statistics:

SigmaStat (Ver 3.1, Systat Software Inc.) was utilized for statistical analyses. Data groups were subjected to normal variance analysis and were compared by a one-tailed t-test. Immunoreactivity data of treatment groups were compared by one-way ANOVA and the Holm-Sidak method. Proportions of two-color staining liposome preparations in flow cytometry were compared by chi-squared ($\chi^2$) analysis.

Figure 24:
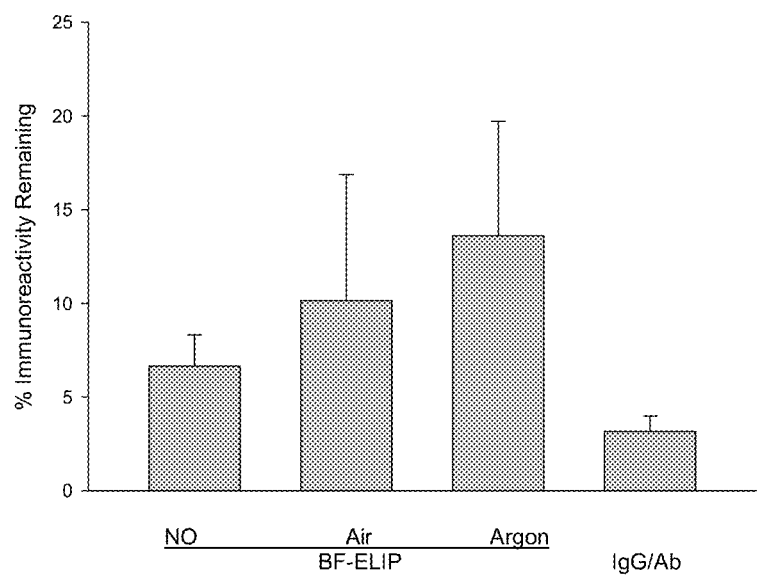
FIG. 24 demonstrates the effect of gas treatment on anti-ICAM-1 immunoreactivity. The reactivity of anti-ICAM1-conjugated ELIP, pressurized with various gases were compared with untreated Ab-ELIP. IgG/Ab refers to a mixture of unconjugated anti-ICAM-1 and mouse IgG in the same proportions as were conjugated, subjected to the same NO pressurization procedure as the Ab-ELIP. Values are the mean of 6-9 determinations; bars=SD.
Figure 25:
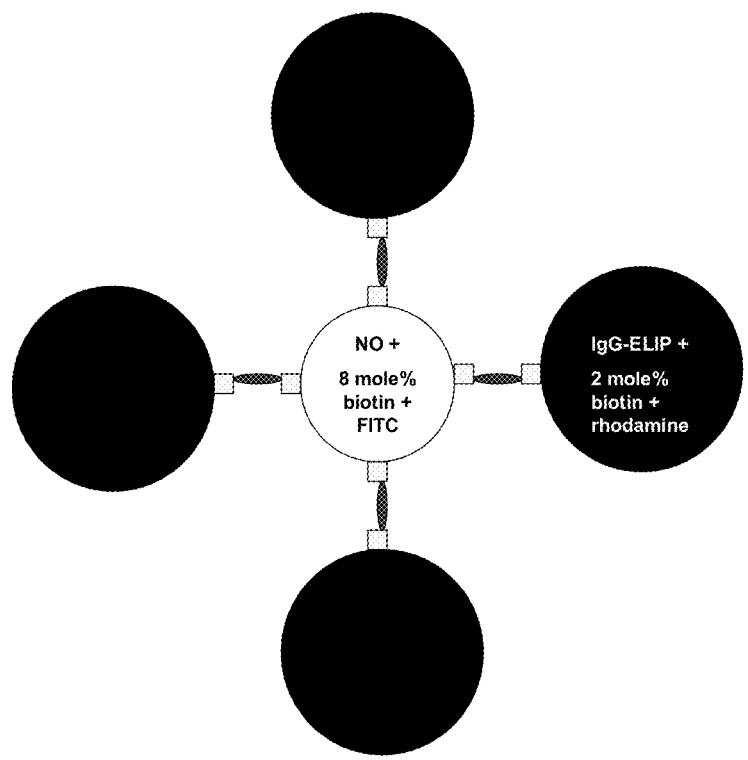
FIG. 25 is a schematic representation of IgG-/NO-bELIP (biotinylated ELIP) modular complexes. Small squares represent biotin molecules; narrow ovals represent streptavidin bridges.
Figure 26:
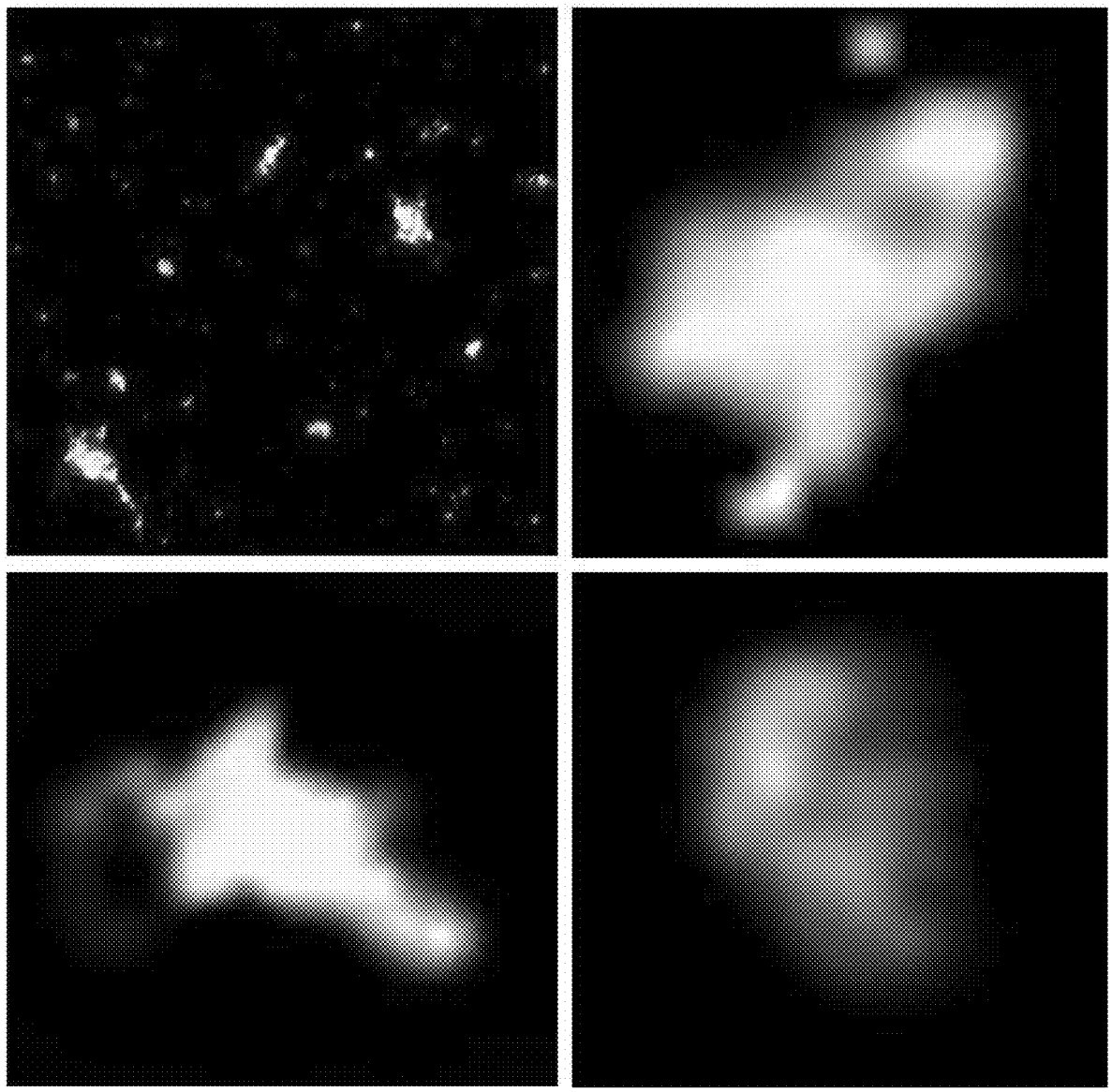
FIG. 26 demonstrates fluorescent microscopy of ELIP modular complexes formed from rhodamine B-labeled IgG-bELIP and fluoresceinated NO-loaded bELIP. Upper left panel: entire field of suspension 30 minutes after complex initiation; oil immersion with 100× objective. Scale: 1 mm=2 µm. Remaining panels: deconvoluted images of individual complexes in the field. Scale: 1 cm=1 µm.
Figure 27:
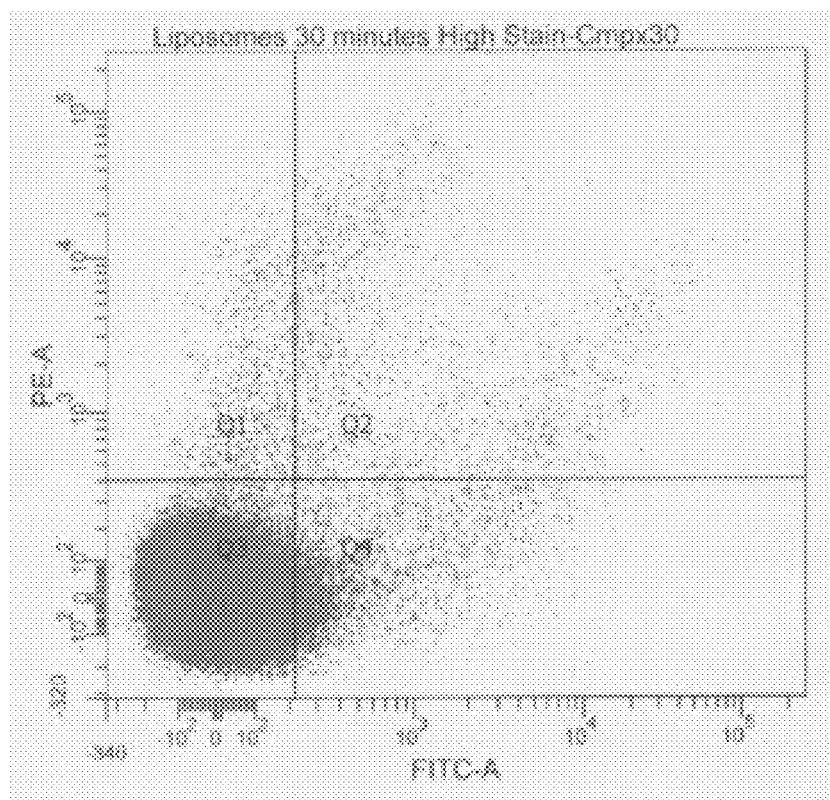
FIG. 27 demonstrates flow cytometry of ELIP modular complexes 30 minutes after initiation. Unlabeled IgG-bELIP was mixed with fluoresceinated NO-bELIP, complexed with streptavidin, and subsequently stained with anti-mouse IgG-phycoerythrin. Points in Quadrant 2 (Q2) represent mixed complexes.

Results:

When BF-ELIP pressurized with NO were tested for ICAM-1 targeting efficiency in the ELISA, it was found that 93% of Ab immunoreactivity had been lost (FIG. 24). The loss of Ab reactivity was apparently caused mainly by the gas pressurization process, since 86.4±6.1% reactivity was lost after pressurization with argon. Additional incremental losses of immunoreactivity were produced by air and NO pressurization (significantly greater than immunoreactivity after Ar pressurization; p=0.0122), indicating further destructive effects of oxidation and free radical reactions, respectively. Liposomal conjugation of Ab was somewhat protective, since 97% of unconjugated Ab reactivity was lost after NO pressurization (FIG. 24). The biotin/avidin-mediated ELIP modular complex scheme (FIG. 25) was tested with rhodamine B-labeled IgG-ELIP and fluoresceinated NO-loaded ELIP modules. Deconvolution fluorescence microscopy of slides prepared from ELIP suspensions 10 and 30 min after complex initiation showed numerous mixed complexes of ≤10-500 liposomes (30-minute panels shown in FIG. 26). No consistent pattern of liposomal organization was seen, but some rhodamine-labeled modules were frequently observed at the edge of the complexes, indicating likelihood that their molecular targeting characteristics would be preserved. Flow cytometric analysis of 200,000 particles indicated that extensive complexation occurred prior to 5 min after initiation, but continued to increase thereafter. Mixed complexes accounted for 0.70% of total particles 5 min after initiation, which increased to 1.19% at 30 min (FIG. 27). The difference between these two proportions was significant ($\chi^2$=258).

Figure 28:
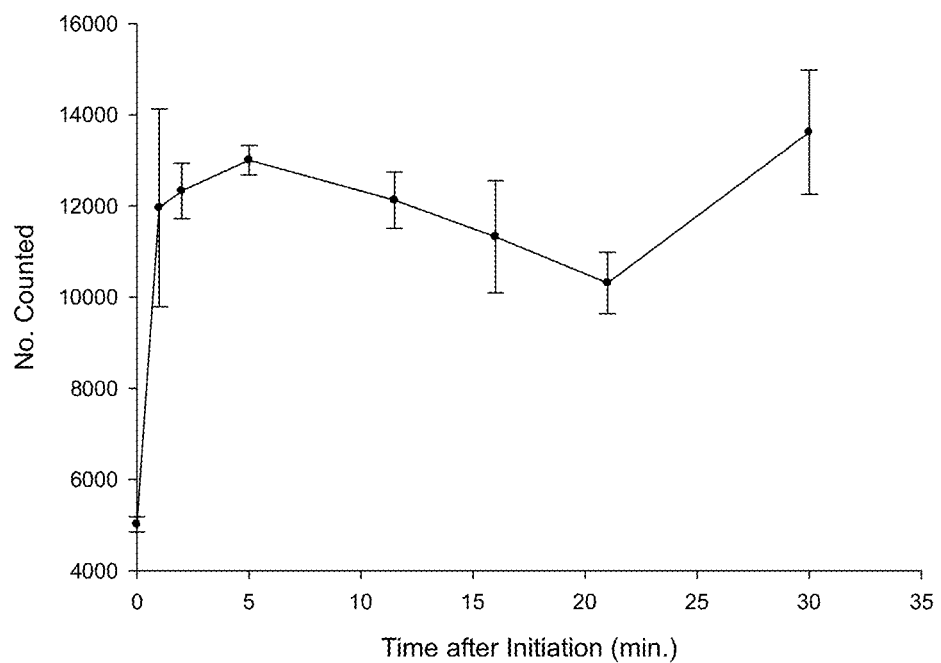
FIG. 28 shows a kinetic analysis of ELIP modular complex formation using the Beckman Coulter Multisizer 3. The number of particles of equivalent spherical diameter=2-4 µm was measured at various time points after complex initiation. Each point represents the mean of 3 determinations (bars=SE). Particle number at 2 min. is significantly greater than at 0 min. ($p<0.01$) and is significantly greater than that of a control consisting of mixed IgG-/NO-bELIP without added streptavidin ($p<0.02$).

Beckman Coulter Multisizer 3 analysis indicated that complex formation was essentially complete within 1 min after initiation (FIG. 28). The median spherical diameter of the IgG-bELIP and the NO-bELIP was 737±83 nm (SD, n=3) and 566±24 nm, respectively. The proportion of new particles >2 μm in diameter formed within 30 min after complex initiation (2.4%) was comparable to the proportion of mixed complexes determined by flow cytometry and may indicate that about half of the total complexes formed contained a single type of liposome. The mean of total particle number after complex formation (1.68±0.14×10$^{10}$/ ml; n=21) was 21% lower than that of the control preparation (2.12±0.19×10¹⁰/ml; n=9, p<0.0001), indicating that >20% of the ELIP were involved in complex formation.

Figure 29:
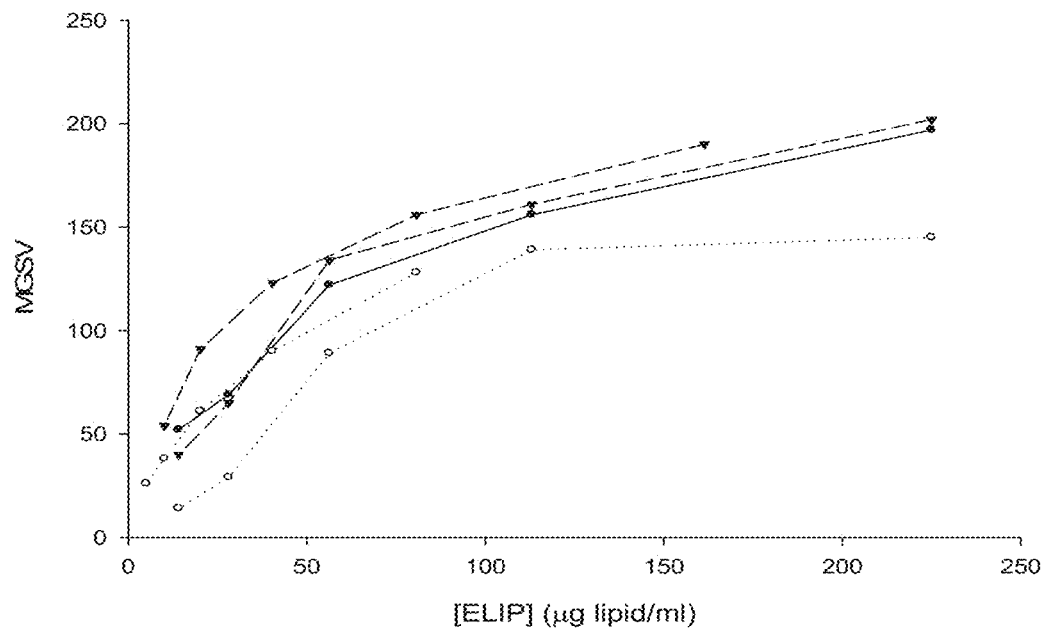
FIG. 29 demonstrates echogenicity of modular ELIP complexes. Densitometric representation of IVUS sonographic brightness, expressed as mean gray scale value (MGSV; 256-value scale), of anti-fibrinogen Abs conjugated to bELIP without NO-bELIP or streptavidin (closed circles, solid line; individual points from one experiment shown), Ab-bELIP with streptavidin only (open circles, dotted line; individual points from two experiments shown), and Ab-/NO-bELIP complexes (inverted triangles, dashed line; individual points from two experiments shown).
Figure 30:
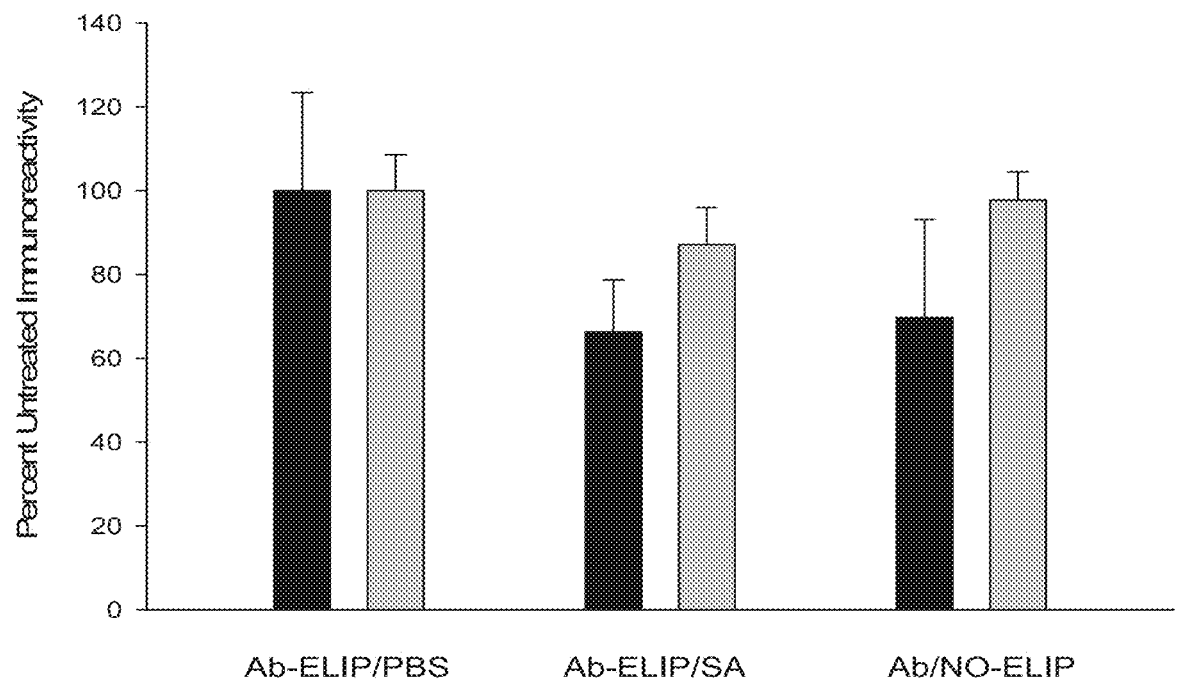
FIG. 30 demonstrates the effect of nitric oxide-loaded biotinylated ELIP module coupling on antibody-conjugated ELIP immunoreactivity. Conjugated Ab: black=anti-fibrinogen; gray=antiICAM-1. Values are the means of 6-8 determinations±SD.

The echogenicity of Ab-bELIP (anti-fibrinogen) was fully retained after complexation with NO-bELIP (FIG. 29). Addition of streptavidin to Ab-bELIP alone, which would be expected to form monotypic complexes, appeared to diminish the echogenicity somewhat. Data demonstrating that the biotin/avidin-mediated modular complex strategy succeeded in preserving targeted ELIP immunoreactivity are shown in FIG. 30. While there was no significant difference between the antigen reactivity of the control preparation and the NO-/Ab-bELIP complexes (p>0.05), with a minimum average 70% retention, monotypic complexes exhibited significantly decreased immunoreactivity (p=0.01).

Figure 31:
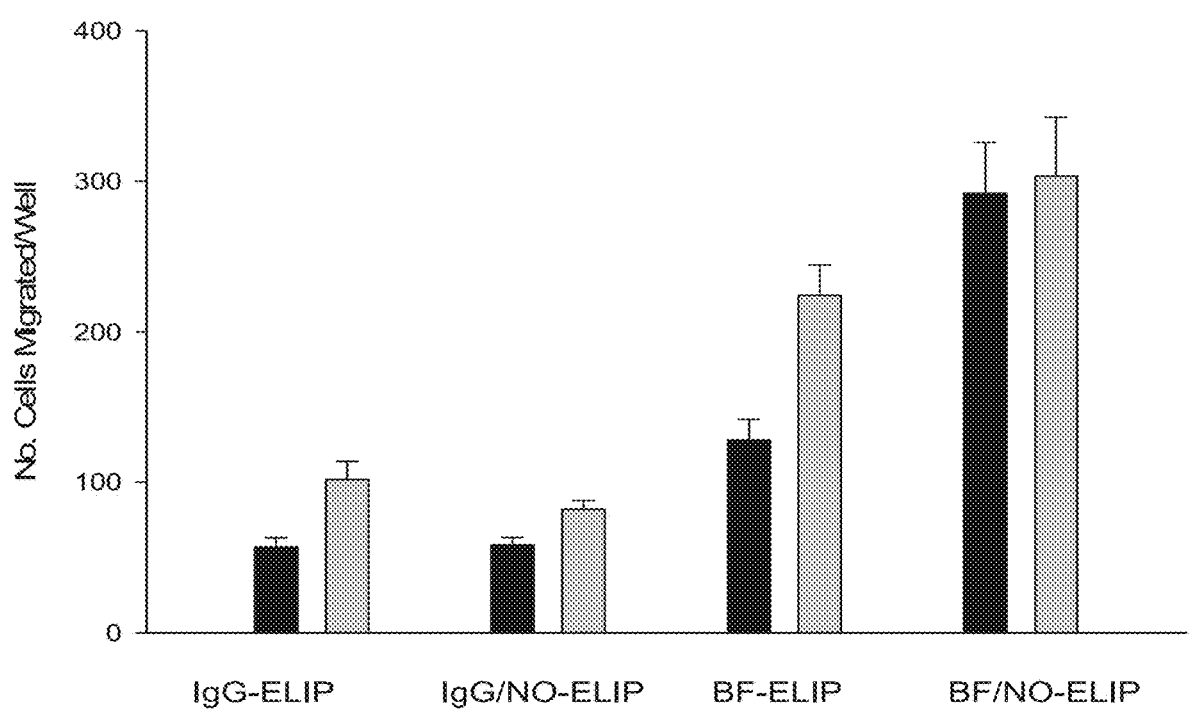
FIG. 31 shows enhancement of BF-ELIP promotion of stem cell passage through endothelial cell monolayers by complexation of NO-loaded biotinylated ELIP. Different colored bars represent separate experiments. Values are the means of 3 determinations±SE.

Transwell passage of CD34+ human peripheral mononuclear cells through TNFα-stimulated human coronary artery endothelial cell monolayers (FIG. 31) was more than doubled (relative to IgG-bELIP controls; p<0.02) by inclusion of BF-bELIP targeted to both CD34 and ICAM-1 prior to introduction of stem cells, followed by washes after each incubation step. Complexation of NO-bELIP to the BF-bELIP caused a more than twofold additional increase in transwell passage (p<0.002). Such incremental stimulation of stem cell penetration after successive washing steps indicates that the enhanced endothelial permeability was caused by NO encapsulated in biotinylated liposomes bound to BF-bELIP through a streptavidin bridge.

6.0. Trifunctional-ELIP with Additional Functionality to Block the Human CXCR4 on Stem Cells.

One possible obstacle to full clinical efficacy of some of the embodiments presently disclosed is the fact that CD34⁻ hematopoietic stem cells express the chemokine receptor CXCR4, this could potentially result in the cells being diverted to the bone marrow through the action of the CXCR4 ligand, stromal cell-derived factor 1 (SDF-1: as describe in for example, Penn M S. Importance of the SDF-1:CXCR4 axis in myocardial repair. Circ Res 2009 May 22; 104(10):1133-5).

One mechanism that would improve the efficiency of MF-ELIP activity is to prevent SDF-1 binding of cell-associated CXCR4 and resultant sequestration, through the addition of another ELIP targeting functionality, for example, a monoclonal antibody to CXCR4 that could block CXCR4 and prevent interactions. Therefore, a bifunctional-ELIP (targeted to ICAM-1 and CD34) without this added feature was compared with a multifunctional, in this example, a trifunctional-ELIP, prepared by the additional conjugation of antibody specific for human CXCR4. The intention was for this additional functionality to block the human CXCR4 on the stem cells and thus prevent potential diversion to the bone marrow.

To clearly demonstrate in vitro proof-of-concept of the usefulness of the principle of adding and mixing blocking functionalities with targeting functionalities to the MF-ELIP, monoclonal antibody specific for human CXCR4 was conjugated to a previously bifuctional-ELIP (targeted to ICAM-1 and CD34) to prevent binding of fluorescently labeled anti-CXCR4 to human coronary fat cells (HCFC), a stromal stem cell population bearing CXCR4. Effective blocking was demonstrated using both fluorescent microscopy and flow cytometry.

Fluorescent Microscopic Analysis:

Biotinylated anti-human CXCR4 antibody (50 μg in 100 μl: BioLegend, San Diego, Calif.) was mixed with 8 μl (8 μg) streptavidin-DyLight 488 conjugate (SA-DL488: Pierce Biotechnology, Rockford, Ill.) and incubated at 4° C. overnight to produce the fluorescent anti-CXCR4/DL488 antibody conjugate. One vial of human coronary fat cells (HCFC: prepared and stored in 1-ml aliquots at −80° C.) was rapidly thawed in a water bath at 37° C. The cells were added to 9.0 ml of 0.02M phosphate-buffered saline (PBS), pH 7.4, and centrifuged at ~400×g in a table-top centrifuge for 10 minutes. The pellet was resuspended in 6 ml PBS; 50 μl was mixed with an equal volume of trypan blue stain. Viable cells were enumerated in a hemacytometer using a phase contrast microscope. The remainder of the cell suspension was equally divided among 6 microfuge tubes and spun in an Eppendorf microfuge for 10 minutes at 2,000×g. Each pellet was resuspended in 0.3 ml of normal human serum (NHS:BioWhittaker, Walkersville, Md.) and incubated for 30 minutes at room temperature; 0.7 ml of PBS was added to each tube, followed by centrifugation and resuspension of each pellet in 0.9 ml of PBS plus 0.1 ml of the following: PBS (untreated negative control); rhodamine-labeled bifunctional (BF)-ELIP (targeted to ICAM-1 and CD34—serving as a positive binding control); DL488 labeled anti-CXCR4 BF-ELIP (serving as a positive control for the presence of CXCR4); IgG-ELIP (nonspecific IgG, untargeted control); rhodamine-labeled BF-ELIP (BF-ELIP test prep); and multifunctional (or trifunctional: TF)-ELIP (test prep). IgG-ELIP, BF-ELIP and TF-ELIP were prepared in the Cardiology Research Laboratory at the Texas Heart Institute, Houston, Tex. The tubes were incubated for 30 minutes at room temperature with rocking and then spun in the microfuge. Pellets were resuspended in 100 μl PBS (first two tubes) or 95 μl PBS+5 μl A-CXCR4/DL488 conjugate (remaining 4 tubes). After 30 minutes at room temperature, 0.9 ml PBS was added to each tube, followed by centrifugation and resuspension of pellets in 0.3 ml PBS each. One drop of each suspension was placed on a glass slide. One drop of glycerol was added to each and a cover slip placed over the fluid. Slides were examined immediately with an Olympus fluorescent microscope fitted with the Nuance Multispectral Imaging System (Cambridge Research & Instrumentation, Inc., Woburn, Mass.) or subsequently after storage in the dark at 4° C.

When rhodamine-labeled BF-ELIP (targeting ICAM-1 and CD34) were used to treat HCFC, fluorescence patterns were seen that indicated that rhodamine labeled-BF-ELIPs were adhering to the cell surfaces, via targeting of the CD34+ stem cells. And when additional BF-ELIP (coupled to DL488 labeled anti-CXCR4) were added, a strong green staining of many cells was seen. When DL488 labeled anti-CXCR4 BF-ELIP followed the addition of rhodamine labeled-BF-ELIP, a yellow staining indicated co-localization of both BF-ELIP populations. Thus it was confirmed that BF-ELIP targeted CD34+ stem cells without blocking of CXCR4 sites, allowing the secondary CXCR4 targeted liposomes to attach to the same cells. However if multifunctional TF-ELIP were first used to bind the cells, no secondary binding of the cells by DL488 labeled anti-CXCR4 BF-ELIP was observed as the samples demonstrated no fluorescence by visual examination. This indicated that CXCR4 sites had been blocked. Even using the Nuance measurement function, green fluorescent intensity of the cells was only 7.7% that of the positive control.

Flow Cytometric Analysis:

One vial of HCFC was thawed and divided into 4 aliquots (2.95×10 viable cells/tube). The samples consisted of unstained HCFC as a negative control, a DL488 fluorescent label conjugated to an anti-CXCR4 antibody-stained positive HCFC control not preincubated with ELIP, BF-ELIP and multifunctional, TF-ELIP samples (as described above). Each pellet was finally resuspended in 0.5 ml PBS before analysis in a Beckman Coulter Gallios flow cytometer. A pronounced high-intensity green fluorescent peak was identified in the cells first treated with BF-ELIP, followed by staining with DL488 fluorescence conjugated anti-CXCR4 antibody. This peak was not present in cells treated with the multifunctional TF-ELIP, providing verification that multifunctional ELIP-conjugated anti-CXCR4 antibody had effectively blocked CXCR4 sites on the stromal cells, such that they were no longer available for staining with DL488 fluorescence conjugated anti-CXCR4 antibody.

These results provide in vitro proof-of-concept of a principle designed to facilitate increased localization of stem cells complexed with multifunctional (TF) ELIP, through the addition of a functionality to block the human CXCR4 on the stem cells and thus prevent potential diversion to the bone marrow. This provides clear evidence that stem cells complexed with multifunctional ELIP are superior to bifunctional-ELIP for use in treating atheroma and atherosclerosis in human and veterinary patients, as well as in related animal models, such as ApoE knockout mice.

7.0. Histopathological Analysis of ELIP Treated Tissue.

In brief, routine histological analysis, such as H&E stain and matrix protein staining, will be conducted for each project. Both paraffin and frozen sections are prepared all projects that need special studies in immunohistochemistry or histochemistry of the arterial tissue samples collected from in vitro, ex vivo and in vivo studies. Specifically, full thickness of arterial wall specimens will be collected from the animal studies. Arterial segments will be fixed in solution containing 4% formaldehyde in PBS for 15 min at 4° C. Samples are snap-frozen in OCT (Tissue Tek) compounds at −80° C. or for paraffin sectioning. Each sample will be divided into two parts for histopathological studies and protein immunoblotting. Tissue for protein and riboxynucleic acid (RNA) are frozen in liquid nitrogen and stored at −80° C. Routine histological examination of arterial tissues with or without ATH will be conducted. Arterial tissues will be fixed in 10% formalin overnight, and dehydrated through an ethanol gradient (0, 75, 95 and 100%). After dehydration, samples are embedded in paraffin, and sectioned by using a microtome. Sections will be deparaffinized, rehydrated and stained with H&E. A total of 20 transverse cryosections (10 uM thickness) will be obtained. In some cases, Mallory's elastin trichrome staining will be performed on the aortic tissue sections.

Light Microscopy:

Sections are dehydrated in graded alcohol, embedded in paraffin and 5-1 μm thick sections cut with a Leica RM2135 or LKB 2218 Historange microtome. Sections are placed on glass slides and stained with H&E, or Mason's Trichrome or modified Movat stains for assessing collagen and elastin fibers.

Fluorescence Microscopy of Fluorochrome-Labeled Cells and Tissue Sections:

Fluorescence of ELIP conjugated with different fluorochromes (e.g., rhodamine and FITC) can be detected in cultured cells and tissue sections by fluorescence microscopy (Olympus). Nuclear counterstaining of cells and tissues is performed using DAPI (Sigma Aldrich, F.W. 450.4), a fluorescent dye which primarily binds to the double strand of the DNA helix. To track stem cells (SC) and determine their fate, SC are labeled with DAPI. SC harvested from culture dishes or freshly isolated from bone marrow, adipose tissue or peripheral blood are washed in PBS, and then suspended in tissue culture medium containing DAPI (1 ug/ml) for 10 min at 37° C. and 5% CO2. After incubation, cells are washed three times with PBS to remove free DAPI. To confirm DAPI nuclear labeling, a drop of cell suspension is placed on a glass cover slip and observed under a fluorescence microscope with an ultraviolet (UV) filter.

Transmission Electron Microscopy (TEM):

Tissue specimens are received in 3% glutaraldehyde. Specimens are post-fixed in 1% osmium tetroxide, dehydrated in a series of graduated alcohol, infiltrated in an acetone/epoxy plastic, and embedded in a plastic mold. Plastic blocks are cut using a Sorvall MT2-B microtome. Thick sections are stained with Toluidine Blue. Sections are then evaluated and appropriate areas identified for thin sectioning. Thin sections are cut at silver-gray interference color (65-80 nm) and placed on copper mesh grids. Grids are stained with uranyl acetate and lead citrate. JEOL 1200 TEM is used to evaluate sections.

Scanning Electron Microscopy (SEM):

For processing, the artery is bisected (parallel with the long axis) and one half submitted for high vacuum SEM (HVSEM) and the other half for low vacuum SEM (LVSEM). Samples are initially fixed in 3% glutaraldehyde. Tissues are then post-fixed in 1% osmium tetroxide. They are dehydrated in a series of increasing grades of ethanol. Further drying is completed with a Critical Point Dryer. Tissue is grounded on an aluminum stub with silver conducting paint. Dried specimens are sputter-coated with gold. Sections are evaluated using a HVSEM (JEOL-JSM-6400LV). For SEM at low vacuum, the vessel samples are dehydrated in a graded series of ethanol. Once absolute alcohol concentration is reached, the specimen is dried at room air or in a vacuum desiccator. Specimens are mounted on an aluminum stub using double sided tape and copper tape. Specimens are placed in a LVSEM (JEOL-JSM-6400LV) and examined under low vacuum, (initial settings are: 15 Kv, spot 80 and pressure 18-50 Pa).

Immunohistochemistry:

After deparaffinization and rehydration, the arterial sections are blocked in PBS containing 2% milk solids at room temperature for 30 minutes, washed three times in PBS, and incubated with primary Abs in PBS at 4° C. overnight. The slides will be incubated with biotin-conjugated second Ab (1:200, Vector Laboratories, Inc) for 60 minutes at room temperature. An avidin-alkaline phosphatase-fast red reagent or the peroxidase-3,3'-diaminodbenzidine (DAB) system (Vectastain ABC kit, Vector) will be used to visualize the Ab stains. Normal mouse IgG (Sigma Chemical Co) will be used as the control for the immunostains. Immunohistochemistry is performed on separate sequential sections using a panel of Abs to determine RhoA Kinase activation [anti-phospho-myosin light chain kinase (pMLC) Ab], NF-kB activation (anti-Rel A Ab, and anti-pSer536 Rel A Ab), macrophage infiltration (anti-Mac1 Ab), and lymphocyte infiltration (anti-CD3 Ab). The first section will be used for H&E stain. In the 2nd section, control IgG will be used to stain the fixed aortic cryosection. The 3rd will be stained with anti-pMLC Ab; the 4th, with Rel A; the 5th with anti-pSer536 Rel A; the 6th with anti-Mac3; the 7th with anti-CD3 Ab; and the remaining sections saved. For staining, sections are washed, incubated with a range of 1:50-1:250 dilutions of primary rabbit Ab. After primary staining, slides are washed and incubated with FITC-conjugated donkey anti-rabbit IgG secondary Ab (Dako). After staining, slides are mounted in anti-fade mounting solution (DAKO Inc. Carpinteria, Calif.), and immunofluorescence detected by a Zeiss LSM510 META System using the 488 nm line of the Argon-laser for excitation of FITC. Relative quantification of staining intensity will be determined relative to IgG controls, and the mean number of positive cells scored per 4 high power fields in the same section by an observer blinded to treatment condition.

Identification of ELIP and ELIP-Targeted Cells and Tissues:

Histochemistry is conducted to analyze ELIP-targeted drug, gene and cell delivery to ATH lesions. As ELIP are lipid rich particles, they are easily identified by Oil Red O staining in culture and on the surface of the arterial wall. Vascular tissues with Ab-coated ELIP delivery will be fixed in formalin or 3-4% paraformaldehyde in PBS. After washing in water, fixed cells and tissues will be incubated with 0.2-0.5% Oil Red O solution for 20-30 min at room temperature. Stains are observed in bright field and quantified using an imaging analyzing software (Q-capture, Olympus). ELIP labeled with fluorochromes are also be detected by fluorescent microscopy. In some experiments anti-Fc immunostaining is performed together with lipid staining to detect ELIP coated with IgG.

Ultrastructural Analysis of Arterial Tissues Treated with ELIP and Ultrasound:

EM is used to analyze ultrastructural changes in the subcellular compartment. ELIP-US targeting may alter platelet structure and affect thrombogenesis, SC-endothelium interaction and the efficiency of drug and gene delivery. The ultrastructure of MF-ELIP interacting with host and donor cells is examined by EM. SEM is performed to characterize endothelial cell integrity and permeability morphologically.

Morphometry of Atheroma (ATH) Plaques:

For specific atheroma morphological characterization, the proximal, distal, medial, and lateral aspects of each artery will be marked on the adventitial surface with India ink and histologic colored dyes. After the collection of arterial segments, the arterial lumen is washed in PBS by perfusion and the arterial tissue then fixed with formalin in situ or injected with a barium-formalin mixture at 100 mmHg. Tissues are fixed with either formalin or by flash freezing. Formalin fixed arteries are used for preparation of paraffin sections and the sections are stained by H&E routinely. Fresh frozen tissue is cross sectioned at 4 mm intervals and immersed in OCT compound, frozen on dry ice, and stored at −80° C. Five micrometer-thick paraffin sections taken from the region of interest are mounted on glass slides and stained with H&E for routine evaluation. For further atheroma plaque characterization, adjacent sections are stained with: Movat's penatchrome for evaluation of elastic tissue and collagen, and phosphotungstic acid (PTAH) for evaluation of matrix proteins. For detection of ELIP loaded with, for example, anti-vascular adhesion molecule-1 (VCAM-1) or anti-ICAM-1 Abs, FITC-conjugated VCAM-1 or ICAM-1 peptides are used as antigens in the immunoassay. In ELIP-targeted stem cell (SC) delivery to atheroma with ultrasound treatment, endothelial cell proliferation, permeability and viability are evaluated in a fixed area and thickness of the endothelium is measured from the internal elastic lamina to the endothelial surface. To detect lipid contents, Oil Red O staining is performed. For atheroma component quantitation, digital images are evaluated. A 3D histologic matrix is made. Using gray level thresholding techniques, atheroma component quantitation and geometric characteristics will be determined. This will be confirmed by estimating the area of each component on the Movat Stain. Additionally, an estimation of adventitial size and inflammatory components will be determined. To assess cavitation injury that leads to in vivo apoptosis, sections are for apoptotic cells by TUNEL staining. Apoptotic cells are TUNEL-positive.

Data Collection and Analysis:

For quantitative evaluation of atheroma lesion formation and extracellular matrix disruption, pathological scores are obtained using computer software and if possible morphometry study performed. The H&E and Mallory's elastin trichrome stains are scored by an independent observer blinded to the treatment condition for evidence of elastin disruption, characteristically seen as complete breaks of the elastic lamina. The number of breaks per high power field will be recorded; the mean of the three section scores is used to quantify elastin disruption for that experimental animal. A mean and standard deviation of the scores for each treatment group are then be compared by ANOVA (SPlus, Insightful). The null hypothesis is rejected at $Pr(F)<0.05$.

Exemplary Histological Findings:

Fluorescence microscopy was performed to evaluate the ability of nitric oxide (NO)-ELIP to alter arterial permeability. A range of particles at different molecular weights were loaded onto rabbit carotid arteries ex vivo using different ultrasound parameters. Substances tested were fluorescently labeled and consisted of different sizes: fluorescein isothiocyanate (FITC)-Dextran [molecular weight (MW)=9600], FITC-bovine serum albumin (BSA) (MW=66,000) and FITC-ELIP (diameter=300 nm). Pretreatment of the arteries with NO-ELIP and ultrasound effectively improved the penetration of all the substances tested in this study.

We pretreated rabbit aortic segments with 100 μg of NO-ELIP before the administration of green fluorescent protein (GFP) labeled stem cells (SC). The arterial segments were then stained with 4', 6-diamidino-2-phenylindole (DAPI, Blue). Pretreatment with NO-ELIP alone did not enhance penetration of SC into the aortic wall. However, when the aortic segments were pretreated with both NO-ELIP and ultrasound treatment, SC were seen in both the endothelial and adventitial layers, indicating both NO-ELIP and ultrasound effect to promote SC penetration into the aortic wall. NO-ELIP were able to deliver NO into cells even in the presence of a potent NO-scavenging agent such as hemoglobin. Pathological examination showed that in porcine carotid arteries in which human type atheroma is developed, application with NO-loaded ELIP inhibited intimal hyperplasia and reduced atheroma size. In contrast, the ELIP with argon gas encapsulation showed no inhibitory effect.

In the aortic sections of ApoE-null mice, ELIP loaded with Rh and anti-ICAM-1 antibodies delivered via the flow of intravascular fluid from an upstream injection could be detected in the aortic wall with ATH lesions. Even after washing the lumen for several minutes with continued flow, these ELIP were successfully targeted to the endothelium (FIG. 4b). The aortic structure and morphology were of high quality. Immunohistochemistry with anti-von Willebrand's Factor (vWF) (factor VIII) Abs revealed intact endothelium and scattered thrombi on the surface of the endothelium (FIG. 4 a). Further analysis of the same or parallel sections demonstrated the presence of Rh-ELIP on the surface of the endothelium or in the subendothelial compartment (FIG. 4 b and c). Morphologic data suggest that Ab-coated Rh-ELIP can adhere and penetrate into the aortic endothelial layer under ultrasound treatment. The importance of these data is that we can prepare and transport specimens for immunohistochemical analysis.

ATH Stabilization by Activation of Soluble Guanylate Cyclase (sGC)

Since activated sGC inhibits migration and SMC proliferation and adenoviruses expressing α1 and β1 sGC subunits enhance the retardation of atheroma by NO donors, to establish the effects of the transfer of the mutant 3β1Cys105 sDNA alone on neointimal growth. ELIP in complex with pcDNA-βCys105 plasmid significantly inhibited the growth of neointima in a balloon injured ATH model of rabbit carotid arteries.

In some embodiments MF-ELIP provide a platform technology for optimization of experimental therapeutic protocols involving concurrent delivery of drugs and genes and to enhance endothelial penetration and survival of stem cells. MF-ELIP to deliver CD34 positive stem cells directly to atheroma with active expression of adhesion proteins. Clearly demonstrating that under the ultrasound enhancement, BF-ELIP can selectively bind peripheral and bone marrow-derived CD34+ cells and provide targeted delivery to vascular endothelium under controlled in vitro conditions. This methodology for stem cell delivery provides a method of improving stem cell therapy for cardiovascular diseases in mammals and humans.

In some embodiments of the invention disclosed herein, a bifunctional or multi-functional echogenic immunoliposome composition or conjugate comprises stem cells derived from porcine adipocytes, an antibody directed against the stem cell antigen CD34, and an antibody directed against the atheroma antigen ICAM-1.

In some embodiments, a bifunctional or multi-functional echogenic immunoliposome composition or conjugate comprises mouse bone marrow stem cells (BMSC), an antibody directed against the stem cell antigen CD34, and an antibody directed against the atheroma antigen ICAM-1.

In some embodiments, a bifunctional or multi-functional echogenic immunoliposome composition or conjugate comprises human mononuclear cells (HMNC), an antibody directed against the stem cell antigen CD34, and an antibody directed against the atheroma antigen ICAM-1.

In some embodiments, a bifunctional or multi-functional echogenic immunoliposome composition or conjugate comprises human mononuclear cells (HMNC), an antibody directed against the stem cell antigen CD146, and an antibody directed against the atheroma antigen ICAM-1.

In some embodiments, a bifunctional or multi-functional echogenic immunoliposome composition or conjugate comprises human coronary fat cells (HCFC), an antibody directed against the stem cell antigen CD34, and an antibody directed against the atheroma antigen ICAM-1.

In some embodiments, a bifunctional or multi-functional echogenic immunoliposome composition or conjugate comprises human coronary fat cells (HCFC), an antibody directed against the stem cell antigen CD146, and an antibody directed against the atheroma antigen ICAM-1.

In some embodiments, a specific multi-functional echogenic immunoliposome composition or conjugate comprises human coronary fat cells (HCFC), an antibody directed against the stem cell antigen CD146, an antibody directed against the atheroma antigen ICAM-1, and a negative or blocking antibody directed against the chemokine receptor CXCR4.

In various embodiments, multi-functional echogenic immunoliposome composition or conjugate comprise any of the stem cells HMNC, HCFC, BMSC, mBMSC and porcine adipocyte-derived stem cells, or any other stem cell bearing one or more stem cell markers. In various embodiments, a multi-functional echogenic immunoliposome composition or conjugate comprises one or more antibodies directed against the stem cell antigenic determinants CD146 or CD34. In various embodiments, a multi-functional echogenic immunoliposome composition or conjugate comprises one or more antibodies directed against one or more of the atheroma antigenic determinants ICAM-1, VEGF, $\alpha_v\beta_3$. In various embodiments, a multi-functional echogenic immunoliposome composition or conjugate comprises one or more negative or blocking antibodies directed against CXCR4 or SDF-1.

In some embodiments, any of the above-described stem cell-bound echogenic immunoliposomes are conjugated to one or more antibodies directed against the stem cell antigenic determinant CD146 or CD34, and are conjugated to one or more antibodies directed against one or more of the atheroma antigenic determinants ICAM-1, VEGF, $\alpha_v\beta_3$, and are also conjugated to one or more antibodies directed against one or more of the atheroma antigenic determinants Tissue Factor, fibrin, VEGF, $\alpha_v\beta_3$. It should be understood that other atheroma and stem cell surface markers could also be similarly employed in further embodiments.

In some embodiments, methods of constructing MF-ELIP loaded with one or more antibodies, drugs and/or desired genes are provided. Upon application of an ultrasound stimulus, these components are released from the echogenic liposome to enhance survival or activity of associated stem cells at the site of a disease tissue which has altered vasculature. The stem-cell bound MF-ELIP is targeted to the disease tissue because the disease tissue expresses unique surface markers (antigens) against which one or more antibodies on the MF-ELIP are directed.

In some embodiments, simultaneous conjugation of liposomes with antibodies selected against specific antigens on monopotent, oligopotent and multipotent stem cells from embryonic or adult tissues or generated by genetic manipulation of adult mature somatic cells and the antigens on the surface of endothelial cells activated under a pathological condition, such as the blood vessels with atherosclerosis or diabetics or a wound with inflammation or tumor. Whereas MF-ELIP are targeted to both stem cell and inflammatory endothelial cell markers in order to facilitate delivery of stem cells to atheroma by "bridging" the two, additional targeting functionalities can be added to facilitate survival and therapeutic utility of the stem cells. For instance, a third antibody could be conjugated to MF-ELIP in order to block counterproductive stem cell functions or a third antibody that binds a marker that is shared by both the stem cells and the target tissue (atheroma) could strengthen the binding of the stem cell-MF-ELIP-target tissue complex.

In some embodiments, a method of identification and/or isolation of the stem cells with MF-ELIP is provided. Stem cells from mammalian embryonic or adult tissues are identified through engagement with MF-ELIP and sorting by gravity precipitation followed by use of a flow cytometer. In certain embodiments, MF-ELIP targeted to both CD34 and ICAM-1 are provided, which are also conjugated to anti-CXCR4, the cell-surface receptor for SDF-1, a chemokine that may cause diversion of the stem cells away from atheroma and to endothelial sites that promote atheroma progression. Successful blockade of the receptor on human coronary adipocyte stem cells and on human peripheral mononuclear cells is assessed by flow cytometry, for example.

In some embodiments, MF-ELIP are loaded with a drug/gene or drugs/genes that can regulate stem cell proliferation, survival and differentiation or that can help improve the microenvironment in which stem cells can better survive and differentiation.

In some embodiments, ultrasound guided delivery of MF-ELIP-tagged stem cells to the vasculatures of diseased tissues, such as atherosclerotic arterial wall is employed.

Echography measurement (i.e., "imaging ultrasound") of tissues with targeted stem cells helps reveal the site of diseased tissues.

In some embodiments, ultrasound is used to enhance migration of MF-ELIP-tagged stem cells into the diseased tissues by passage through the blood vessel wall. In some embodiments, inhibition of inflammation in a wound or atheroma through MF-ELIP-tagged stem cell delivery with ultrasound enhancement of drugs or gene targeting is provided. In some embodiments, anti-apoptotic drug delivery with enhanced MF-ELIP-stem cell function and survival are provided. In some embodiments, therapeutic gene delivery to a disease tissue is accomplished by MF-ELIP-tagged stem cells in which the immunoliposome contains the gene that is desired to be transferred to the tissue.

In certain embodiments, a multi-functional echogenic immunoliposome construct or complex is provided that comprises: (a) a liposome comprising a stem cell enhancing agent and at least one ultrasound reflective material, wherein the liposome is formulated to release the agent upon receiving an ultrasound stimulus; and (b) at least two or more different types of antibodies attached to the liposome, which are capable of recognizing antigenic determinants on the stem cells or endothelium of atheroma. The first type of antibody or antibodies recognizes antigenic determinants of stem cells and is used to link the liposome to stem cells, and the second type of antibody or antibodies capable of reacting with antigenic determinants on a target tissue is used to link the stem cells bearing the antibody-conjugated liposome to the target tissue. The third type of antibody or antibodies capable of recognizing antigenic determinants on both the stem cells and target tissue is used to enforce the engagement and homing of stem cells to the target tissue. In some embodiments, the construct further includes a stem cell bound to the first antibody and having at least a first antigenic determinant thereon.

In certain other embodiments, a method of isolating stem cells that are useful in an above-described method is provided which includes: engaging a population of cells comprising stem cells from a mammalian embryonic or adult tissue with a plurality of multi-functional immunoliposome constructs. Each such construct comprises at least two or more different types of antibodies attached to a liposome, wherein these antibodies are capable of recognizing a cluster of antigenic determinants on the stem cell, to obtain highly selective, enforced binding of the immunoliposomes to the stem cell in a mixture containing unbound cells. This method further includes sorting the mixture by gravity precipitation or aspiration, to separate the stem cells with bound immunoliposomes from the unbound cells; and/or passing the isolated stem cell-bound immunoliposomes thorough a fluorescent activated cell sorter or flow cytometer, to obtain a defined, purified population of stem cells bound to the immunoliposomes.

In certain embodiments, a multi-functional echogenic immunoliposome construct or complex is provided that comprises: (a) a liposome comprising a stem cell enhancing agent and at least one ultrasound reflective material, wherein the liposome is formulated to release the agent upon receiving an ultrasound stimulus, and (b) at least two or more different types of antibodies attached to the liposome, which are capable of recognizing antigenic determinants on the stem cells or endothelium of atheroma. The first type of antibody or antibodies recognizes antigenic determinants of stem cells and is used to link the liposome to stem cells, and the second type of antibody or antibodies capable of reacting with antigenic determinants on a target tissue is used to link the stem cells bearing the antibody-conjugated liposome to the target tissue. The third type of antibody or antibodies capable of recognizing antigenic determinants on both the stem cells and target tissue is used to enforce the engagement and homing of stem cells to the target tissue. In some embodiments, the construct further includes a stem cell bound to the first antibody and having at least a first antigenic determinant thereon.

In certain embodiments, a method of treating a disease tissue in a patient suffering from a pathological condition is provided. The method comprises: (a) delivering to a target tissue comprising the disease tissue a construct comprising: (1) a stem cell having at least a first antigenic determinant; (2) an echogenic liposome comprising a stem cell enhancing agent; and (3) at least a first and second antibody attached to the liposome, wherein the first antibody binds the first antigenic determinant on the stem cell, the second antibody is capable of binding a second antigenic determinant on the target tissue, and wherein the liposome is formulated to release the agent upon receiving an ultrasound stimulus, and the disease tissue expresses at least the second antigenic determinant, to bind the construct to the disease tissue by antibody-antigenic determinant recognition. The method also includes (b) applying the ultrasound stimulus to the resulting tissue-attached construct to release the stem cell enhancing agent from the liposome.

In certain embodiments, the construct used in the method comprises a third antibody that is either capable of recognizing a third antigenic determinant on the target tissue or recognizes a third antigenic determinant on the stem cell. The third antibody is also attached to the liposome, the disease tissue expresses at least the second antigenic determinant, and the construct is attached to the disease tissue by antibody-antigenic determinant recognition between at least the second antibody-second antigenic determinant.

In certain embodiments, a method of isolating stem cells that are useful in an above-described method is provided which includes: engaging a population of cells comprising stem cells from a mammalian embryonic or adult tissue with a plurality of multi-functional immunoliposome constructs. Each such construct comprises at least two or more different types of antibodies attached to a liposome, wherein these antibodies are capable of recognizing a cluster of antigenic determinants on the stem cell, to obtain highly selective, enforced binding of the immunoliposomes to the stem cell in a mixture containing unbound cells. This method further includes sorting the mixture by gravity precipitation, to separate the stem cells with bound immunoliposomes from the unbound cells; and/or passing the isolated stem cell-bound immunoliposomes thorough a flow cytometer, to obtain a defined, purified population of stem cells bound to the immunoliposomes.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments of the invention have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The section headings used herein are for organizational purposes only and are not to be construed as limiting the subject matter described. All documents, or portions of documents, cited in this application, including, but not limited to, patents, patent applications, articles, books, and treatises, are hereby incorporated herein by reference to the extent that they provide procedures or explanation that is supplemental to the this disclosure. In the event that one or more of the incorporated references define a term in a manner that contradicts the definition of that term in this application, this application controls.

What is claimed is:

1. A method of treating atherosclerosis in a patient, wherein said treating comprises:
    delivering to an atherosclerotic lesion:
        (i) a CD34-positive stem cell; and
        (ii) an echogenic liposome comprising:
            (a) at least one ultrasound reflective material; and
            (b) at least a first and second antibody attached to said liposome, wherein said first antibody is an anti-CD34 antibody that binds to the CD34 on the CD34-positive stem cell, wherein said second antibody is an anti-ICAM antibody that localizes said liposome to said atherosclerotic lesion, and wherein said liposome responds to an ultrasound stimulus, thereby localizing said CD34-positive stem cell to said lesion and stabilizing said lesion,
    wherein said liposome is formulated to release a stem cell enhancing agent selected from the group consisting of: antibodies, drugs, genes, and combinations thereof, in response to an ultrasound releasing stimulus.

2. The method of claim 1, wherein said echogenic liposome further comprises a third antibody attached to said liposome, wherein said third antibody recognizes an antigenic determinant on said atherosclerotic lesion or said stem cell, and wherein said antigenic determinant is selected from the group consisting of: CD146, chemokine receptors, CD140, CD144, PDGF receptor, CD133, CD13, CD29, CD44, CD90, sca-1, VEGF receptor 1, c-kit, stem cell growth factors, SDF, TNF alpha and beta, insulin like growth factor-1, clusterin, intercellular adhesion molecule-1 (ICAM-1), vascular cell adhesion molecule-1 (VCAM-1), fibrin, integrins, vascular endothelial growth factors (VEGF, including, but not limited to, species A-D and VEGF-A isoforms 110, 120 or 121, 164 or 165, 188 or 189 and 206), tissue factor, smooth muscle cell myosins and actins, matrix metalloproteinases (MMPs), E-selectin and P-selectin, insulin-like growth factor-1 receptor (IGF-1R), von Willebrand's factor and macrophage markers (for example AM-3K, 7C3, 25F9, 27E10), carboxypeptidase M (CPM), cathepsin K, chitotriosidase, CD14, CD68 (Ki-M7, Y2/131, Y1/82A, EBM11), CD163, CD163 soluble (sCD163), CSF-1R (colony-stimulating factor-1 receptor), ED-1, ED-2, ED-3, EMR1, F4/80, Factor XIII-A, ferritin, HAM-56, Ki-M1P, lysozyme M, MAC-1/MAC-3, Myeloid-related protein (MRP) 14, RFD7/RFD9, RM3/1, scavenger receptors (ScR), CD36, ScR-I/II, chemokine receptors (CXCR4, MCP-1) receptors, CD18, and TNF receptors (R1/R2).

3. The method of claim 2, wherein said antigenic determinant is CXCR4 or SDF-1 receptor.

4. The method of claim 2, wherein said third antibody-antigenic determinant recognition blocks the binding of a marker on said atherosclerotic lesion, wherein blocking of said marker enhances a function selected from the group consisting of: stem cell survival; stimulation of said atherosclerotic lesion to express a factor that increases survival of the stem cell; stimulation of said atherosclerotic lesion to express a factor that increases activity of the stem cell; stimulation of said atherosclerotic lesion to express a factor that increases differentiation of the stem cell; and combinations thereof.

5. The method of claim 1, wherein said stem cell enhancing agent is further selected from the group consisting of: c-kit, clusterin (ApoJ), erythropoietin, tetracycline, statins, caspase inhibitors, losartan potassium, ubiquitin, and combinations thereof.

6. The method of claim 1, wherein said stem cell enhancing agent improves the microenvironment of a lesion-bound construct to enhance stem cell survival and differentiation.

7. The method of claim 1, further comprising:
    delivering said echogenic liposome to said lesion by an ultrasound-guided catheter through a blood vessel;
    measuring by echography to locate said lesion-localized echogenic liposome; and
    visualizing said lesion-localized echogenic liposome, wherein said ultrasound-guided catheter delivery comprises imaging ultrasound.

* * * * *